(12) United States Patent
Black et al.

(10) Patent No.: US 7,273,877 B2
(45) Date of Patent: Sep. 25, 2007

(54) 5-SUBSTITUTED-4-[(SUBSTITUTED PHENYL) AMINO]-2-PYRIDONE DERIVATIVES

(75) Inventors: Shannon Leigh Black, Heidelberg (DE); Michael David Kaufman, Ypsilanti, MI (US); Daniel Fred Ortwine, Saline, MI (US); Mark Stephen Plummer, Dexter, MI (US); John Quin, III, Ann Arbor, MI (US); Gordon William Rewcastle, Auckland (NZ); Aurash B. Shahripour, Ann Arbor, MI (US); Julie Ann Spicer, Auckland (NZ); Christopher Emil Whitehead, Ypsilanti, MI (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 401 days.

(21) Appl. No.: 10/876,100

(22) Filed: Jun. 24, 2004

(65) Prior Publication Data

US 2005/0026964 A1 Feb. 3, 2005

Related U.S. Application Data

(60) Provisional application No. 60/483,307, filed on Jun. 27, 2003, provisional application No. 60/489,603, filed on Jul. 23, 2003.

(51) Int. Cl.
*A61K 31/4439* (2006.01)
*C07D 413/04* (2006.01)
*C07D 213/72* (2006.01)

(52) U.S. Cl. .................. 514/340; 514/349; 546/269.4; 546/297

(58) Field of Classification Search ............. 546/269.1, 546/297, 269.4; 514/340, 349
See application file for complete search history.

(56) References Cited

U.S. PATENT DOCUMENTS 4,166,859 A 9/1979 Stahle

FOREIGN PATENT DOCUMENTS

| DE | 26 30 060 | 1/1978 |
| DE | 27 50 170 | 5/1978 |
| WO | WO99/01421 | 1/1999 |

OTHER PUBLICATIONS

Albert, A., et al., "Triazanaphthalenes. Part II.[1] Covalent Hydration In 1,4,6-triazanaphthalenes," *J. Chem. Soc.*, 1963, 5156-5166.
Berge, S., et al., "Pharmaceutical Salts," *Journal of Pharmaceutical Science*, 1977, 1-19, vol. 66, No. 1.
Bushweller, J., et al., "Sulfoxide Analogues Of Dihydro- And terahydroprephenate As Inhibitors Of Prephenate Dehydratase," *J. Org. Chem.*, 1989, 2404-2409, vol. 54, No. 10.
Cory, E., et al., "Protection Of Hydroxyl Groups As *tert*-Butyldimethysilyl Derivatives," *J. Am. Chem. Soc.*, 1972, 6190-6191, vol. 94.
Dhanak, D., et al., "Synthesis Of [6] (2,4) Pyridinophanes," *J. Chem. Soc., Perkin Trans. 1*, 1987, 2829-2832.
Fey, T., et al., "Improved Methods For Transplanting Split-Heart Neonatal Cardiac Grafts Into The Ear Pinna Of Mice And Rats," *Journal Of. Pharmacological And Toxicological Methods*, 1998, 9-17, vol. 39.
Hargreaves, K., et al., "A New And Sensitive Method For Measuring Thermal Nociception In Cutaneous Hyperalgesia," *Pain*, 1988, 77-88, vol. 32.
Kayser, V., et al., "Local And Remote Modifications Of Nociceptive Sensitivity During Carrageenin-Induced Inflammation In The Rat," *Pain*, 99-107, vol. 28.
Mitsuya, M., et al., "A Potent, Long-Acting, Orally active (2R)-2-[(1R)-3,3-Difluorocyclopentyl]-2-hydroxy-2-phenylacetamide: A Novel Muscarinic $M_3$ Receptor Antagonist With High Selectivity For $M_3$ over $M_2$ Receptors," *J. Med. Chem.*, 2000, 5017-5029, vol. 43.
Schwab, J., et al., "Pro-And Anti-Inflammatory Roles Of Interleukin-1 In Recurrence Of Bacterial Cell Wall-Induced Arthritis In Rats," *Infection And Immunity*, 1991, 4436-4442, vol. 59, No. 12.

Primary Examiner—Zinna N. Davis
(74) Attorney, Agent, or Firm—Brian C. Zielinski; Galina M. Yakovleva

(57) ABSTRACT

The present invention relates to 5-substituted-4-(substituted) phenylamino-2-pyridone derivatives, pharmaceutical compositions and methods of use thereof.

17 Claims, No Drawings

5-SUBSTITUTED-4-[(SUBSTITUTED PHENYL) AMINO]-2-PYRIDONE DERIVATIVES

This application claims priority benefits under 35 U.S.C. § 119(e) of U.S. Provisional application No. 60/483,307, filed 27 Jun. 2003 and U.S. Provisional application No. 60/489,603, filed 23 Jul. 2003.

FIELD OF THE INVENTION

The present invention relates to 5-substituted-4-(substituted)phenyl)amino-2-pyridone derivatives, pharmaceutical compositions and methods of use thereof.

BACKGROUND OF THE INVENTION

MAPK/ERK Kinase ("MEK") enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates the MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinase. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

It has been found that the compounds of the present invention are inhibitors of MEK and are useful in the treatment of a variety of proliferative disease states, such as conditions related to the hyperactivity of MEK, as well as diseases modulated by the MEK cascade.

SUMMARY OF THE INVENTION

The present invention provides a compound of formula

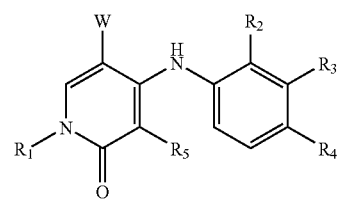

I wherein
W is

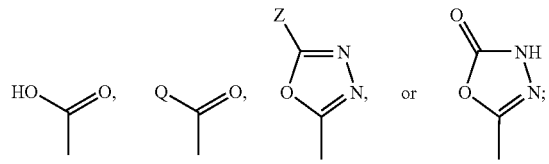

Q is —O—$(CH_2)_k CH_3$, —$NH_2$, —NH[$(CH_2)_k CH_3$], or —NH[O$(CH_2)_k CH_3$], wherein the —$NH_2$ is optionally substituted with between 1 and 2 substituents independently selected from methyl and amino, and the —$(CH_2)_k CH_3$ moieties of the —O—$(CH_2)_k CH_3$, —NH[$(CH_2)_k CH_3$], and —NH[O$(CH_2)_k CH_3$] groups are optionally substituted with between 1 and 3 substituents independently selected from hydroxy, amino, alkyl, cycloalkyl and hydroxyalkyl;

Z is —$NH_2$, —NH[$(CH_2)_k CH_3$], or —NH[O$(CH_2)_k CH_3$], wherein the —$NH_2$ is optionally substituted with between 1 and 2 substituents independently selected from methyl and amino, and the —$(CH_2)_k CH_3$ moieties of the —NH[$(CH_2)_k CH_3$], and —NH[O$(CH_2)_k CH_3$] groups are optionally substituted with between 1 and 3 substituents independently selected from hydroxy and amino;

$R_1$ is hydrogen, $C_{1-6}$ alkyl, $C_{2-4}$ alkenyl or —$(CH_2)_kO(CH_2)_kOCH_3$, wherein the $C_{1-6}$ alkyl is optionally substituted with between 1 and 2 substituents independently selected from hydroxy, —COOH, and cyano;

$R_2$ is hydrogen, chlorine, fluorine or methyl;

$R_3$ is hydrogen, chlorine, fluorine, methyl, or $CF_3$;

$R_4$ is bromine, chlorine, fluorine, iodine, $C_{1-6}$ alkyl, $C_{2-4}$ alkenyl, $C_{2-6}$ alkynyl, $C_{3-6}$ cycloalkyl, —$(CH_2)$—$C_{3-6}$ cycloalkyl, cyano, —O—$(C_{1-4}$ alkyl), —S—$(C_{1-2}$ alkyl), —$SOCH_3$, —$SO_2CH_3$, —$SO_2NR_6R_7$, —C≡C—$(CH_2)_nNH_2$, —C≡C—$(CH_2)_nNHCH_3$, —C≡C—$(CH_2)_nN(CH_3)_2$, —C≡C—$CH_2OCH_3$, —C=C$(CH_2)_nOH$, —C=C—$(CH_2)_nNH_2$, —$CHCHCH_2OCH_3$, —CHCH—$(CH_2)_nNHCH_3$, —CHCH—$(CH_2)_nN(CH_3)_2$, —$(CH_2)_pCO_2R_6$, $C(O)C_{1-3}$ alkyl, $C(O)NHCH_3$, —$(CH_2)_mNH_2$, —$(CH_2)_mNHCH_3$, —$(CH_2)_mN(CH_3)_2$, —$(CH_2)_mOR_8$, —$CH_2S(CH_2)_t(CH_3)$, —$(CH_2)_pCF_3$, —C≡$CCF_3$, —CH=$CHCF_3$, —$CH_2CHCF_2$, —CH=$CF_2$, —$(CF_2)_vCF_3$, —$CH_2(CF_2)_nCF_3$, —$(CH_2)_vCF(CF_3)_2$, —$CH(CF_3)_2$, —$CF_2CF(CF_3)_2$, or —$C(CF_3)_3$, wherein the $C_{1-6}$ alkyl and $C_{2-6}$ alkynyl are optionally substituted with between 1 and 3 substituents independently selected from hydroxy and alkyl; or $R_3$ and $R_4$ can be joined together to form a six-membered aryl ring, five-membered cycloalkyl ring or a five or six-membered heteroaryl ring;

$R_5$ is hydrogen, chlorine, fluorine, or methyl;

$R_6$ and $R_7$ are each independently hydrogen, methyl, or ethyl;

k is 0 to 3;
m is 1 to 4;
n is 1 to 2;
p is 0 to 2;
t is 0 to 1;
v is 1 to 5;

and pharmaceutically acceptable salts, $C_{1-6}$ amides and $C_{1-6}$ esters thereof.

An embodiment of the present invention provide a compound of formula I, as defined above, and pharmaceutically acceptable salts thereof.

Additionally provided by the present invention are compounds having the structure

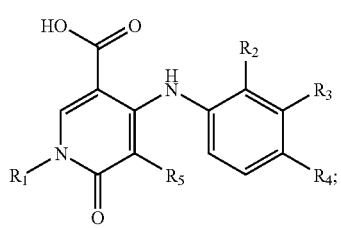

Ia

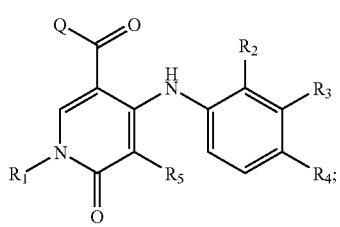

Ib

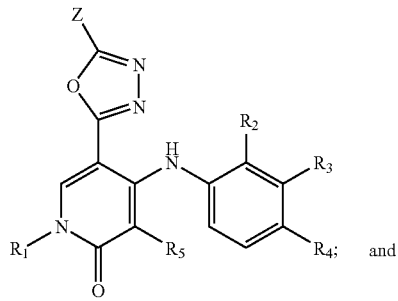

Ic

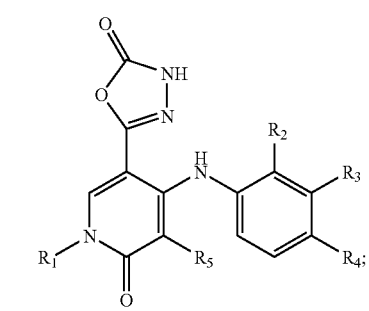

Id wherein Q, $R_1$, $R_2$, $R_3$, $R_4$, and $R_5$ are defined as above.

Another embodiment of the present invention provide a compound of formula I, having the structure

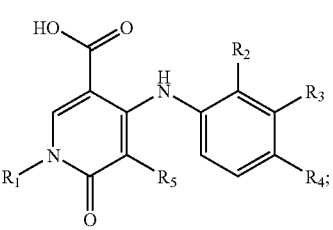

Ia wherein $R_1$, $R_2$, $R_3$, $R_4$, and $R_5$ are defined as above.

Another embodiment of the present invention provide a compound of formula I, having the structure

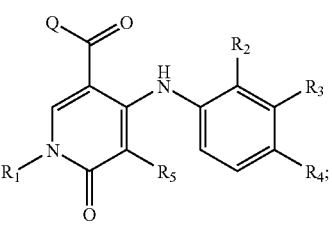

Ib wherein Q, $R_1$, $R_2$, $R_3$, $R_4$, and $R_5$ are defined as above.

Another embodiment of the present invention provide a compound of formula Ib, wherein Q is —$OCH_2CH_3$, —$NH_2$, —$NHCH_3$, —$N(CH_3)_2$, —$NHNH_2$, —$N(H)(CH_2)_3NH_2$, —$N(H)(CH_2)_kOH$, —$N(H)O(CH_2)_2OH$, —$N(H)CH_2CH(OH)CH_2OH$, —$N(H)CH(CH_2OH)_2$, —$N(H)C(CH_2OH)_3$, —$OCH_2C(NH_2)(CH_2OH)_2$, —$N(H)CH(CH_2OH)(CH_3)$, or —$N(H)CH_2CH(CH_3)(OH)$.

Another embodiment of the present invention provide a compound of formula Ib, wherein Q is —NH$_2$ or —NH[O(CH$_2$)$_k$CH$_3$], wherein the —NH[O(CH$_2$)$_k$CH$_3$] is optionally substituted with between 1 and 3 hydroxy substituents.

Another embodiment of the present invention provide a compound of formula I, having the structure

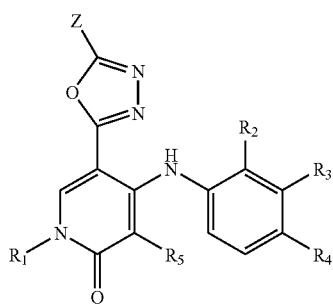

Ic wherein Q, R$_1$, R$_2$, R$_3$, R$_4$, and R$_5$ are defined as above.

Another embodiment of the present invention provide a compound of formula Ic, wherein Q is —N(H)(CH$_2$)$_2$OH, —N(H)CH(CH$_2$OH)$_2$, or —N(H)CH$_2$CH(OH)CH$_2$OH.

Another embodiment of the present invention provide a compound of formula I, having the structure

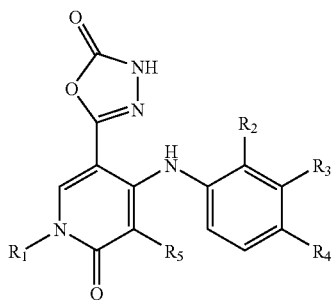

Id wherein R$_1$, R$_2$, R$_3$, R$_4$, and R$_5$ are defined as above.

Another embodiment of the present invention provide a compound of formula I, wherein R$_1$ is hydrogen, C$_{1-3}$ alkyl, —(CH$_2$)$_2$OH, —CH$_2$COOH, —(CH$_2$)$_3$CN, —(CH$_2$)$_2$O(CH$_2$)$_2$OCH$_3$, CH$_2$—CH=CH, CH$_2$CH(OH)CH$_2$OH, (CH$_2$)$_3$OH.

Another embodiment of the present Invention provide a compound of formula I, wherein R$_2$ is hydrogen, chlorine, or fluorine.

Another embodiment of the present invention provide a compound of formula I, wherein R$_3$ is hydrogen, chlorine, methyl, or CF$_3$.

Another embodiment of the present invention provide a compound of formula I, wherein R$_4$ is bromine, chlorine, fluorine, iodine, C$_{1-3}$ alkyl, C$_{2-3}$ alkynyl, cyano, —S—CH$_3$, —SOCH$_3$, —(CF$_2$)$_3$CF$_3$, wherein the C$_{1-3}$ alkyl and C$_{2-3}$ alkynyl are optionally substituted with hydroxy; or R$_3$ and R$_4$ can be joined together to form a five-membered cycloalkyl ring, five-membered heteroaromatic ring, or six-membered aromatic ring.

Another embodiment of the present invention provide a compound of formula I, wherein R$_4$ is iodine, C$_{1-3}$ alkyl, C$_{2-3}$ alkynyl or S—CH$_3$.

Another embodiment of the present invention provide a compound of formula I, wherein R$_4$ is iodine, ethyl, allyl or S—CH$_3$.

Another embodiment of the present invention provide a compound of formula I, wherein R$_5$ is hydrogen.

Another embodiment of the present invention provide a pharmaceutical composition comprising a compound of formula I, and a pharmaceutically acceptable carrier.

Another embodiment of the present invention provide a method of treating a proliferative disease in a patient in need thereof comprising administering a therapeutically effective amount of a compound of formula I.

Another embodiment of the present invention provide a method of treating cancer in a patient in need thereof comprising administering a therapeutically effective amount of a compound of formula I.

Another embodiment of the present invention provide a method of treating restenosis, psoriasis, autoimmune disease, atherosclerosis, rheumatoid arthritis, heart failure, chronic pain, neuropathic pain, or osteoarthritis in a patient in need thereof comprising administering a therapeutically effective amount of a compound of formula I.

Another embodiment of the present invention provide a method of treating cancer in a patient in need thereof comprising administering a therapeutically effective amount of a compound of formula I in combination with radiation therapy or at least one chemotherapeutic agent.

Another embodiment of the present invention provide a compound of formula I which is selected from the group consisting of:

4-(2-Fluoro-4-iodoanilino)-N-(2-hydroxyethoxy)-1-methyl-6-oxo-1,6-dihydro-3-pyridinecarboxamide;

4-[2-Fluoro-4-(3-hydroxy-1-propynyl)anilino]-N-(2-hydroxyethoxy)-1-methyl-6-oxo-1,6-dihydro-3-pyridinecarboxamide;

4-[2-Fluoro-4-(3-hydroxypropyl)anilino]-N-(2-hydroxyethoxy)-1-methyl-6-oxo-1,6-dihydro-3-pyridinecarboxamide;

4-(2-Fluoro-4-iodoanilino)-N-(2-hydroxyethyl)-1-methyl-6-oxo-1,6-dihydro-3-pyridinecarboxamide;

4-(2-Fluoro-4-iodoanilino)-N-(3-hydroxypropyl)-1-methyl-6-oxo-1,6-dihydro-3-pyridinecarboxamide;

4-[2-Fluoro-4-(3-hydroxy-1-propynyl)anilino]-N-(2-hydroxyethyl)-1-methyl-6-oxo-1,6-dihydro-3-pyridinecarboxamide;

4-[2-Fluoro-4-(3-hydroxypropyl)anilino]-N-(2-hydroxyethyl)-1-methyl-6-oxo-1,6-dihydro-3-pyridinecarboxamide;

4-[2-Fluoro-4-(3-hydroxy-1-propynyl)anilino]-N-(3-hydroxypropyl)-1-methyl-6-oxo-1,6-dihydro-3-pyridinecarboxamide;

4-[2-Fluoro-4-(3-hydroxypropyl)anilino]-N-(3-hydroxypropyl)-1-methyl-6-oxo-1,6-dihydro-3-pyridinecarboxamide;

4-(2-Fluoro-4-iodoanilino)-1-methyl-6-oxo-1,6-dihydro-3-pyridinecarboxamide;

4-(2-Fluoro-4-iodoanilino)-N-(2-hydroxyethyl)-6-oxo-1,6-dihydro-3-pyridinecarboxamide;

4-(4-Ethynyl-2-fluoroanilino)-N-(2-hydroxyethyl)-6-oxo-1,6-dihydro-3-pyridinecarboxamide;

4-(4-Ethyl-2-fluoroanilino)-N-(2-hydroxyethyl)-6-oxo-1,6-dihydro-3-pyridinecarboxamide;

4-(2-Fluoro-4-iodoanilino)-N-(3-hydroxypropyl)-6-oxo-1,6-dihydro-3-pyridinecarboxamide;

4-(4-Ethynyl-2-fluoroanilino)-N-(3-hydroxypropyl)-6-oxo-1,6-dihydro-3-pyridinecarboxamide;

4-(4-Ethyl-2-fluoroanilino)-N-(3-hydroxypropyl)-6-oxo-1,6-dihydro-3-pyridinecarboxamide;
4-(4-Ethynyl-2-fluoroanilino)-1-methyl-6-oxo-1,6-dihydro-3-pyridinecarboxamide;
4-(4-Ethyl-2-fluoroanilino)-1-methyl-6-oxo-1,6-dihydro-3-pyridinecarboxamide;
4-(2-Fluoro-4-iodoanilino)-6-oxo-1,6-dihydro-3-pyridinecarboxamide;
4-[2-Fluoro-4-(3-hydroxy-1-propynyl)anilino]-1-methyl-6-oxo-1,6-dihydro-3-pyridinecarboxamide;
4-[2-Fluoro-4-(3-hydroxypropyl)anilino]-1-methyl-6-oxo-1,6-dihydro-3-pyridinecarboxamide;
4-(2-Fluoro-4-iodoanilino)-1-(2-hydroxyethyl)-6-oxo-1,6-dihydro-3-pyridinecarboxamide;
4-(2-Fluoro-4-iodoanilino)-1-(2-hydroxyethyl)-N-(3-hydroxypropyl)-6-oxo-1,6-dihydro-3-pyridinecarboxamide;
(4-(2-Fluoro-4-iodoanilino)-5-{[(3-hydroxypropyl)amino]carbonyl}-2-oxo-1(2H)-pyridinyl)acetic acid;
5-(Aminocarbonyl)-4-(2-fluoro-4-iodoanilino)-2-oxo-1(2H)-pyridinyl)acetic acid;
1-(3-Cyanopropyl)-4-(2-fluoro-4-iodoanilino)-6-oxo-1,6-dihydro-3-pyridinecarboxamide;
1-Ethyl-4-(2-fluoro-4-iodoanilino)-6-oxo-1,6-dihydro-3-pyridinecarboxamide;
4-(2-Fluoro-4-iodoanilino)-6-oxo-1-propyl-1,6-dihydro-3-pyridinecarboxamide;
4-(2-Fluoro-4-iodoanilino)-1-[2-(2-methoxyethoxy)ethyl]-6-oxo-1,6-dihydro-3-pyridinecarboxamide;
1-Allyl-4-(2-fluoro-4-iodoanilino)-6-oxo-1,6-dihydro-3-pyridinecarboxamide;
1-(2,3-Dihydroxypropyl)-4-(2-fluoro-4-iodoanilino)-6-oxo-1,6-dihydro-3-pyridinecarboxamide;
4-(2-Fluoro-4-iodoanilino)-1-(3-hydroxypropyl)-6-oxo-1,6-dihydro-3-pyridinecarboxamide;
4-(2,4-Difluoroanilino)-N-(2-hydroxyethoxy)-1-methyl-6-oxo-1,6-dihydro-3-pyridinecarboxamide;
4-(2,4-Difluoroanilino)-N-(3-hydroxypropyl)-1-methyl-6-oxo-1,6-dihydro-3-pyridinecarboxamide;
4-(2-Fluoro-4-methylanilino)-N-(2-hydroxyethoxy)-1-methyl-6-oxo-1,6-dihydro-3-pyridinecarboxamide;
4-(2-Fluoro-4-methylanilino)-N-(3-hydroxypropyl)-1-methyl-6-oxo-1,6-dihydro-3-pyridinecarboxamide;
4-(2-Fluoro-4-methylanilino)-1-methyl-6-oxo-1,6-dihydro-3-pyridinecarboxamide;
4-(4-Bromo-2-fluoroanilino)-N-(2-hydroxyethoxy)-1-methyl-6-oxo-1,6-dihydro-3-pyridinecarboxamide;
4-(4-Bromo-2-fluoroanilino)-N-(3-hydroxypropyl)-1-methyl-6-oxo-1,6-dihydro-3-pyridinecarboxamide;
4-(4-Bromo-2-fluoroanilino)-1-methyl-6-oxo-1,6-dihydro-3-pyridinecarboxamide;
4-[2-Fluoro-4-(1,1,2,2,3,3,4,4,4-nonafluorobutyl)anilino]-1-methyl-6-oxo-1,6-dihydro-3-pyridinecarboxamide;
N-(3-Hydroxypropyl)-1-methyl-4-(2-naphthylamino)-6-oxo-1,6-dihydro-3-pyridinecarboxamide;
1-Methyl-4-(2-naphthylamino)-6-oxo-1,6-dihydro-3-pyridinecarboxamide;
4-[(1-Chloro-2-naphthyl)amino]-N-(2-hydroxyethoxy)-1-methyl-6-oxo-1,6-dihydro-3-pyridinecarboxamide;
N-(2,3-Dihydroxypropyl)-4-(2-fluoro-4-iodoanilino)-1-methyl-6-oxo-1,6-dihydro-3-pyridinecarboxamide;
4-(2-Fluoro-4-iodoanilino)-N-[2-hydroxy-1-(hydroxymethyl)ethyl]-1-methyl-6-oxo-1,6-dihydro-3-pyridinecarboxamide;
4-(2-Fluoro-4-iodoanilino)-N-[2-hydroxy-1,1-bis(hydroxymethyl)ethyl]-1-methyl-6-oxo-1,6-dihydro-3-pyridinecarboxamide;
2-Amino-3-hydroxy-2-(hydroxymethyl)propyl-4-(2-fluoro-4-iodoanilino)-1-methyl-6-oxo-1,6-dihydro-3-pyridinecarboxylate;
4-(2-Fluoro-4-iodoanilino)-N-(2-hydroxy-1-methylethyl)-1-methyl-6-oxo-1,6-dihydro-3-pyridinecarboxamide;
4-(2-Fluoro-4-iodoanilino)-N-(2-hydroxypropyl)-1-methyl-6-oxo-1,6-dihydro-3-pyridinecarboxamide;
4-(2-Fluoro-4-iodoanilino)-N,1-dimethyl-6-oxo-1,6-dihydro-3-pyridinecarboxamide;
4-(2-Fluoro-4-iodoanilino)-N,N,1-trimethyl-6-oxo-1,6-dihydro-3-pyridinecarboxamide;
N-(3-Aminopropyl)-4-(2-fluoro-4-iodoanilino)-1-methyl-6-oxo-1,6-dihydro-3-pyridinecarboxamide;
4-(4-Cyano-2-fluoroanilino)-1-methyl-6-oxo-1,6-dihydro-3-pyridinecarboxamide;
4-(2-fluoro-4-iodoanilino)-1-methyl-6-oxo-1,6-dihydro-3-pyridinecarboxylic acid;
4-(3,4-Dichloro-phenylamino)-1-methyl-6-oxo-1,6-dihydro-pyridine-3-carboxylic acid amide;
4-(3,4-Dimethyl-phenylamino)-1-methyl-6-oxo-1,6-dihydro-pyridine-3-carboxylic acid ethyl ester;
4-(Indan-5-ylamino)-1-methyl-6-oxo-1,6-dihydro-pyridine-3-carboxylic acid ethyl ester;
1-Methyl-6-oxo-4-(2,3,4-trichloro-phenylamino)-1,6-dihydro-pyridine-3-carboxylic acid ethyl ester;
4-(4-Chloro-3-trifluoromethyl-phenylamino)-1-methyl-6-oxo-1,6-dihydro-pyridine-3-carboxylic acid ethyl ester;
4-(1H-Indol-5-ylamino)-1-methyl-6-oxo-1,6-dihydro-pyridine-3-carboxylic acid ethyl ester;
4-(1H-Indazol-5-ylamino)-1-methyl-6-oxo-1,6-dihydro-pyridine-3-carboxylic acid ethyl ester;
4-(3,4-Dimethyl-phenylamino)-1-methyl-6-oxo-1,6-dihydro-pyridine-3-carboxylic acid;
4-(Indan-5-ylamino)-1-methyl-6-oxo-1,6-dihydro-pyridine-3-carboxylic acid;
1-Methyl-6-oxo-4-(2,3,4-trichloro-phenylamino)-1,6-dihydro-pyridine-3-carboxylic acid;
4-(4-Chloro-3-trifluoromethyl-phenylamino)-1-methyl-6-oxo-1,6-dihydro-pyridine-3-carboxylic acid;
4-(3,4-Dimethyl-phenylamino)-1-methyl-6-oxo-1,6-dihydro-pyridine-3-carboxylic acid amide;
4-(Indan-5-ylamino)-1-methyl-6-oxo-1,6-dihydro-pyridine-3-carboxylic acid amide;
4-(4-Chloro-3-trifluoromethyl-phenylamino)-1-methyl-6-oxo-1,6-dihydro-pyridine-3-carboxylic acid amide;
1-Methyl-6-oxo-4-(2,3,4-trichloro-phenylamino)-1,6-dihydro-pyridine-3-carboxylic acid amide;
4-(2-Fluoro-4-iodo-phenylamino)-1-methyl-6-oxo-1,6-dihydro-pyridine-3-carboxylic acid;
4-(2-Fluoro-4-iodo-phenylamino)-1-methyl-6-oxo-1,6-dihydro-pyridine-3-carboxylic acid amide;
4-(2-Fluoro-4-methyl-phenylamino)-1-methyl-6-oxo-1,6-dihydro-pyridine-3-carboxylic acid ethyl ester;
4-(2-Fluoro-4-iodo-phenylamino)-1-methyl-6-oxo-1,6-dihydro-pyridine-3-carboxylic acid ethyl ester;
4-(2-Fluoro-4-iodo-phenylamino)-1-methyl-6-oxo-1,6-dihydro-pyridine-3-carboxylic acid ethyl ester;
4-(4-Ethynyl-2-fluoro-phenylamino)-1-methyl-6-oxo-1,6-dihydro-pyridine-3-carboxylic acid ethyl ester;
4-(4-Ethynyl-2-fluoro-phenylamino)-1-methyl-6-oxo-1,6-dihydro-pyridine-3-carboxylic acid (2-hydroxyethyl)-amide;

4-(4-Ethynyl-2-fluoro-phenylamino)-1-methyl-6-oxo-1, 6-dihydro-pyridine-3-carboxylic acid (2-hydroxy-1-hydroxymethyl-ethyl)-amide;

4-(4-Ethynyl-2-fluoro-phenylamino)-1-methyl-6-oxo-1, 6-dihydro-pyridine-3-carboxylic acid (2,3-dihydroxy-propyl)-amide;

4-(4-Ethyl-2-fluoro-phenylamino)-1-methyl-6-oxo-1,6-dihydro-pyridine-3-carboxylic acid (2-hydroxy-ethyl)-amide;

4-(4-Ethyl-2-fluoro-phenylamino)-1-methyl-6-oxo-1,6-dihydro-pyridine-3-carboxylic acid (2-hydroxy-1-hydroxymethyl-ethyl)-amide;

4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(4-Ethyl-2-fluoro-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-1-methyl-6-oxo-1,6-dihydro-pyridine-3-carboxylic acid;

4-(2-Fluoro-4-methylsulfanyl-phenylamino)-1-methyl-6-oxo-1,6-dihydro-pyridine-3-carboxylic acid (3-hydroxy-propyl)-amide;

4-(2-Fluoro-4-methylsulfanyl-phenylamino)-1-methyl-6-oxo-1,6-dihydro-pyridine-3-carboxylic acid amide;

4-(2-Fluoro-4-methylsulfanyl-phenylamino)-1-methyl-6-oxo-1,6-dihydro-pyridine-3-carboxylic acid (2-hydroxy-ethyl)-amide;

4-(2-Fluoro-4-methylsulfanyl-phenylamino)-1-methyl-6-oxo-1,6-dihydro-pyridine-3-carboxylic acid (2,3-dihydroxy-propyl)-amide;

4-(2-Fluoro-4-methylsulfanyl-phenylamino)-1-methyl-6-oxo-1,6-dihydro-pyridine-3-carboxylic acid (2-hydroxy-1-hydroxymethyl-ethyl)-amide;

4-(2-Fluoro-4-methylsulfanyl-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-5-[5-(2-hydroxy-1-hydroxymethyl-ethylamino)-[1,3,4]oxadiazol-2-yl]-1-methyl-1H-pyridin-2-one;

5-[5-(2,3-Dihydroxy-propylamino)-[1,3,4]oxadiazol-2-yl]-4-(2-fluoro-4-methylsulfanyl-phenylamino)-1-methyl-1H-pyridin-2-one;

4-(4-Ethynyl-2-fluoro-phenylamino)-5-[5-(2-hydroxy-ethylamino)-[1,3,4]oxadiazol-2-yl]-1-methyl-1H-pyridin-2-one;

4-(4-Ethynyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(2-Fluoro-4-methanesulfinyl-phenylamino)-1-methyl-6-oxo-1,6-dihydro-pyridine-3-carboxylic acid (2-hydroxy-1-hydroxymethyl-ethyl)-amide;

4-(2-Fluoro-4-iodo-phenylamino)-1-methyl-6-oxo-1,6-dihydro-pyridine-3-carboxylic acid hydrazide;

4-(4-Ethynyl-2-fluoro-phenylamino)-1-methyl-6-oxo-1, 6-dihydro-pyridine-3-carboxylic acid;

4-(4-Ethyl-2-fluoro-phenylamino)-1-methyl-6-oxo-1,6-dihydro-pyridine-3-carboxylic acid ethyl ester;

4-(4-Ethyl-2-fluoro-phenylamino)-1-methyl-6-oxo-1,6-dihydro-pyridine-3-carboxylic acid;

4-(2-Fluoro-4-iodo-phenylamino)-1-methyl-5-(5-oxo-4, 5-dihydro-[1,3,4]oxadiazol-2-yl)-1H-pyridin-2-one; or 4-(4-Ethyl-2-fluoro-phenylamino)-1-methyl-6-oxo-1,6-dihydro-pyridine-3-carboxylic acid amide.

The invention also provides the use of a compound of Formula I for the manufacture of a medicament for the treatment of the disease states or diseases provided above.

DETAILED DESCRIPTION OF THE INVENTION

Certain terms are defined below and by their usage throughout this disclosure.

The terms "halogen" or "halo" in the present invention refer to a fluorine, bromine, chlorine, and iodine atom or fluoro, bromo, chloro, and iodo. The terms fluorine and fluoro, for example, are understood to be equivalent herein.

Alkyl groups, such as "$C_{1-6}$ alkyl", include aliphatic chains (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, isobutyl, sec-butyl, t-butyl, pentyl, 2-pentyl, 3-pentyl, isopentyl, neopentyl, (R)-2-methylbutyl, (S)-2-methylbutyl, 3-methylbutyl, 2,3-dimethylpropyl, hexyl, and the like. The term "$C_{1-6}$ alkyl" includes within its definition the terms "$C_{1-4}$ alkyl" and "$C_{1-2}$ alkyl".

The term "alkoxy" as used herein refers to a straight or branched alkyl chain attached to an oxygen atom. The term "$C_{1-8}$ alkoxy" as used herein refers to a straight or branched alkyl chain having from one to eight carbon atoms attached to an oxygen atom. Typical $C_{1-8}$ alkoxy groups include methoxy, ethoxy, propoxy, isopropoxy, butoxy, t-butoxy, pentoxy and the like. The term "$C_{1-8}$ alkoxy" includes within its definition the terms "$C_{1-6}$ alkoxy" and "$C_{1-4}$ alkoxy".

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof. Like alkyl groups, unsaturated groups may be straight chain or branched. Examples of alkenyls and alkynyls include vinyl, allyl, 2-methyl-2-propenyl, cis-2-butenyl, trans-2-butenyl, and acetyl.

Cycloalkyl groups, such as $C_{3-6}$ cycloalkyl, refer to a saturated hydrocarbon ring structure containing from 3 to 6 atoms. Typical $C_{3-6}$ cycloalkyl groups include cyclopropyl, cyclobutyl, cyclopentyl, cyclohexyl, and the like.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl).

The term "heteroaryl", as used herein, unless otherwise indicated, includes monocyclic aromatic heterocycles containing five or six ring members, of which from 1 to 4 can be heteroatoms selected, independently, from N, S and O, and bicyclic aromatic heterocycles containing from eight to twelve ring members, of which from 1 to 4 can be heteroatoms selected, independently, from N, S and O.

Heterocyclic radicals, which include but are not limited to heteroaryls, include: furyl, (is)oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their nonaromatic counterparts. Further examples of heterocyclic radicals include thienyl, piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, octahydrobenzofuranyl, (iso)quinolinyl, naphthyridinyl, benzimidazolyl, and benzoxazolyl.

The present invention includes the hydrates and the pharmaceutically acceptable salts and solvates of the compounds defined by Formula I. The compounds of this invention can possess a sufficiently basic functional group, and accordingly react with any of a number of inorganic and organic acids, to form a pharmaceutically acceptable salt.

The term "pharmaceutically acceptable salt" as used herein, refers to salts of the compounds of Formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 1977, 66:2-19, which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Example of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate, and the like. A preferred pharmaceutically acceptable salt is hydrochloride.

It should be recognized that the particular counterion forming a part of any salt of this inventions is usually not of a critical nature, so long as the salt as a whole is pharmacologically acceptable and as long as the counterion does not contribute undesired qualities to the salt as a whole. It is further understood that such salts may exist as a hydrate.

The enantiomers of compounds of the present invention can be resolved by one of ordinary skill in the art using standard techniques well-known in the art, such as those described by J. Jacques, et al., *Enantiomers, Racemates, and Resolutions*, John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The compounds of Formula I can be prepared by techniques and procedures readily available to one of ordinary skill in the art, for example by following the procedures as set forth in the following Schemes, or analogous variants thereof. These synthetic strategies are further exemplified in examples below. These schemes are not intended to limit the scope of the invention in any way.

As used herein, the following terms have the meanings indicated: "AcOH" refers to acetic acid; "CDI" refers to 1,1'-carbonyldiimidazole; Celite® refers to a filter agent which is acid washed and approximately 95% $SiO_2$; "$CHCl_3$" refers to chloroform; "$CH_2Cl_2$" and "DCM" refer to dichloromethane; "conc." refers to concentrated; "DABCO" refers to 1,4-diazabicyclo[2.2.2]octane; "DIEA" refers to N,N-diisopropylethylamine; "DMA" refers to N,N-dimethylacetamide; "DMF" refers to N,N-dimethylformamide; "DMSO" refers to methyl sulfoxide; "DMT-MM" refers to 4-(4,6-dimethoxy-1,3,5-triazin-2-yl)-4-methylmorpholinium chloride; "EtOAc" refers to ethyl acetate; "EtOH" refers to ethanol; "$Et_2O$" refers to diethyl ether; "FMOC" refers to 9H-fluoren-9-ylmethyl ester; "h" refers to hours; "HCl" refers to hydrochloric acid; "Me" refers to methyl; "MeOH" refers to methanol; "$Me_2SO_4$" refers to dimethyl sulfate; "min" refers to minutes; "NaOH" refers to sodium hydroxide' "$Na_2SO_4$" refers to sodium sulfate; "N-MM" refers to N-methylmorpholine; "Pd/C" refers to palladium on carbon; "PE" refers to petroleum ether which can be substituted with hexanes; "$(Ph_3P)_2PdCl_2$" refers to dichlorobis-(triphenylphosphine)palladium(II); "$(Ph_3P)_4Pd$" refers to tetrakis-(triphenylphosphine)-palladium (0); "PS" refers to polymer—supported; "R.T." refers to room temperature; "sat" refers to saturated; "TEA" refers to triethylamine; "TFA" refers to trifluoroacetic acid; "THF" refers to tetrahydrofuran; "TLC" refers to thin layer chromatography and "TMS" refers to trimethylsilyl. All other terms and substituents, unless otherwise indicated, are previously defined.

The reagents and starting materials are readily available to one of ordinary skill in the art. Schemes 1-5 provide syntheses of the compounds of Formula I.

Scheme 1

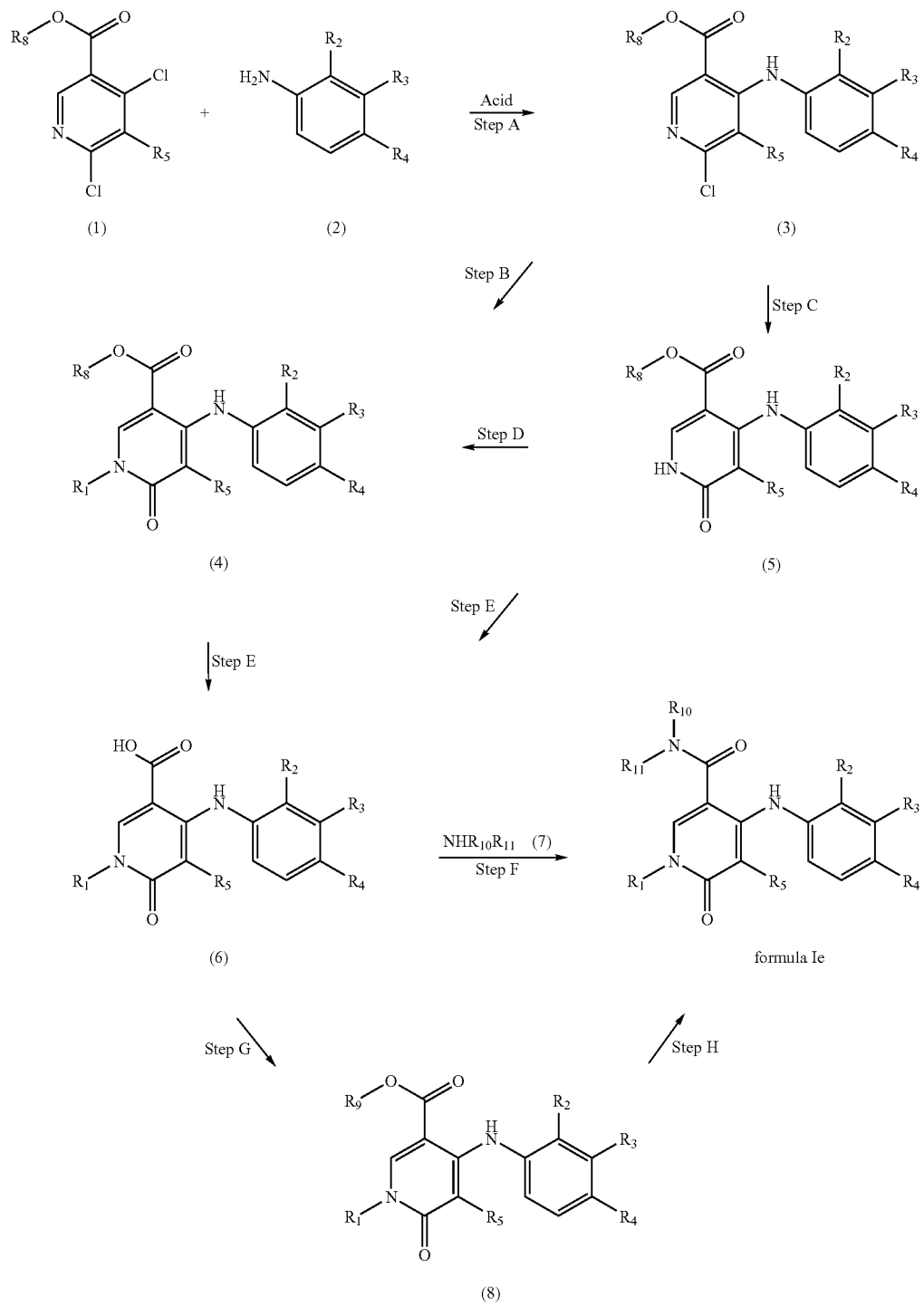

$R_8$ is alkyl or substituted alkyl; $R_9$ is active leaving group such as $C_6F_5$
$R_{10}$ and $R_{11}$ are independently hydrogen, amino, alkyl, substituted alkyl, alkoxy or substituted alkoxy In Scheme 1, Step A, a suitable dichloronicotinic ester (1) is coupled with a suitable aniline (2) to provide a 4-(arylamino)nicotinate (3). For example, the aniline (2) and the dichloronicotinate (1) are dissolved in a suitable organic solvent with an acid catalyst and heated at reflux for several hours. Preferred solvents are polar solvents such as ethanol, and preferred acid catalysts are mineral acids such as concentrated HCl. The reaction is typically complete within about 12 to 36 hours. The product ester (3) is typically isolated by filtration after cooling of the reaction mixture, and further purified, if desired, by standard methods such as chromatography or crystallization.

In Scheme 1, Step B, a 4-(arylamino)nicotinate (3) is reacted with an alkylating agent, such as dimethyl sulfate, to produce an N-alkyl pyridinium salt which is then hydrolyzed, without purification, to the 4-(arylamino)pyridone ester (4). For example, the 4-(arylamino)nicotinate (3) is dissolved in a suitable solvent, such as chloroform, and cooled before the addition of the alkylating agent. The resulting mixture is allowed to warm to room temperature and heated at reflux for several hours. The reaction is typically complete within about 24 hrs. After cooling to room temperature, the mixture is hydrolyzed with, for example, a mixture of triethylamine, acetic acid and ethyl alcohol, and heated at reflux until the reaction is complete. The product ester (4) is typically isolated by filtration, and further purified, if desired, by standard methods such as chromatography or crystallization.

In Scheme 1, Step C, a 4-(arylamino)nicotinate (3) is hydrolyzed with, for example, aqueous acetic acid at reflux to produce a 4-(arylamino)pyridone ester (5), which is typically isolated by filtration, after cooling of the reaction mixture, and further purified, if desired, by standard methods such as chromatography or crystallization.

In Scheme 1, Step D, a 4-(arylamino)pyridone ester (5) is reacted with an alkylating agent in the presence of a base such as NaH to produce an N-alkyl-4-(arylamino)pyridone ester (4), which is typically isolated by filtration, after cooling of the reaction mixture and dilution with water, and further purified, if desired, by standard methods such as chromatography or crystallization.

In Scheme 1, Step E, the N-alkyl-4-(arylamino)pyridone ester (4) or the 4-(arylamino)pyridone ester (5) is hydrolyzed to the carboxylic acid (6) by treatment with a base, such as NaOH or $K_2CO_3$, in a suitable solvent, such as aqueous ethanol.

In Scheme 1, Step F, the compounds of formula Ie are generally obtained by the union of 4-(arylamino)-pyridone acid (6) with amine or alkoxylamine (7) by the action of a peptide coupling agent in the presence of a base, if necessary. Preferred coupling agents include 1,1'-carbonyldiimidazole (CDI), diphenylphoshinic chloride (DPP-Cl), benzotriazol-yl-oxy-tripyrrolidinophosphonium hexafluorophosphate (PyBOP), benzotriazol-1-yloxy-tris(dimethylamino)phosphonium hexafluorophosphate (BOP), N,N'-dicyclohexylcarbodiimide (DCC), 1-ethyl-3-(3-dimethylaminopropyl)carbodiimide hydrochloride (EDCl), or 4-(4,6-dimethoxy-1,3,5-triazin-2-yl)-4-methylmorpholinium chloride (DMT-MM). Preferred bases include diisopropylethylamine, triethylamine, 4-methylmorpholine, or pyridine or a substituted pyridine, for example, 4-dimethylaminopyridine or 2,6-dimethylpyridine. Preferred solvents are polar aprotic solvents such as dichloromethane, tetrahydrofuran, or dimethylformamide, except with DMT-MM where methanol-THF mixtures are preferred. The reactions are generally carried out at a temperature between about −78° C. to about 25° C., and are normally complete within about 1 hour to about 5 days. The product amide can be isolated by removing the solvent, for example by evaporation under reduced pressure, and further purified, if desired, by standard methods such as chromatography, crystallization, or distillation.

It would be understood by one of skill in the art that the substituent at $R_4$ on the diphenylamine (3) can be reduced before the coupling reaction. The reduction is performed on alkene or alkyne derivatives under conditions known in the art, such as through hydrogenation, for example with Pd/C under an atmosphere of hydrogen.

In Scheme 1, Step G, a 4-(arylamino)-pyridone acid (6) is reacted with a active ester, in the presence of a base, if necessary, to produce an activated 4-(arylamino)-pyridone ester (8). Preferred active esters include pentafluorophenyl trifluoroacetate and preferred bases include diisopropylethylamine, triethylamine, 4-methylmorpholine, pyridine or a substituted pyridine, for example, 4-dimethylaminopyridine or 2,6-dimethylpyridine. Preferred solvents are polar aprotic solvents such as dichloromethane, tetrahydrofuran, dimethylformamide, or N,N-dimethylacetamide.

In Scheme 1, Step H, the compounds of formula Ie are generally obtained by the union of 4-(arylamino)-pyridone ester (8) with amine or alkoxylamine (7) in the presence of a base, if necessary. Preferred bases include diisopropylethylamine, triethylamine, 4-methylmorpholine, pyridine or a substituted pyridine, for example, 4-dimethylaminopyridine or 2,6-dimethylpyridine. Preferred solvents are polar aprotic solvents such as dichloromethane, tetrahydrofuran, dimethylformamide, or N,N-dimethylacetamide. The reactions are generally carried out at a temperature between about −78° C. to about 25° C., and are normally complete within about 1 hour to about 5 days. The product amide can be isolated by removing the solvent, for example by evaporation under reduced pressure, and further purified, if desired, by standard methods such as chromatography, crystallization, or distillation.

It would be understood by one of skill in the art that the substituent $R_1$ may be further transformed, such as by oxidation, reduction, deprotection, or hydrogenation.

Scheme 2

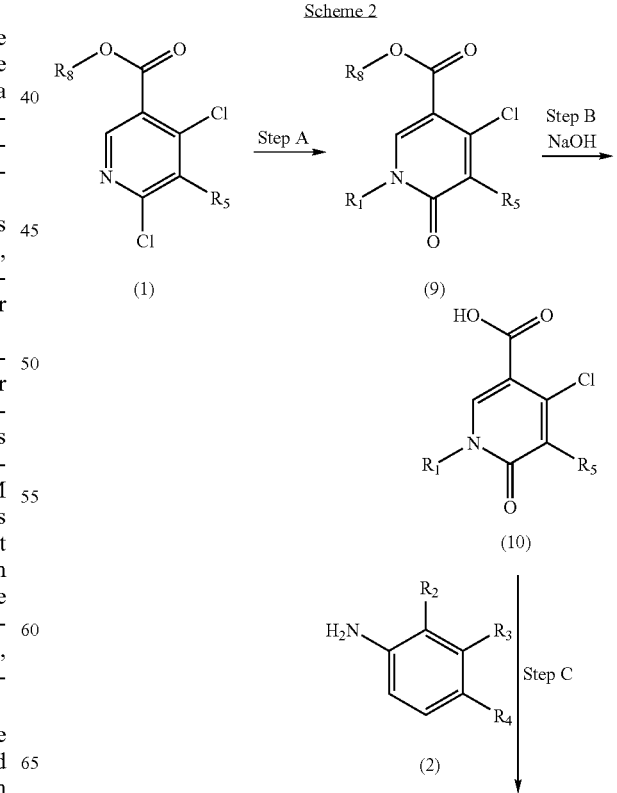

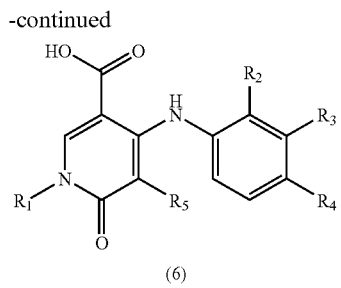

$R_6$ is alkyl or substituted alkyl

In Scheme 2, Step A, a suitable dichloronicotinic ester (1) is reacted with an alkylating agent, for example dimethylsulfate, to produce an N-alkyl pyridinium salt which is then hydrolyzed, without purification, to the 4-chloropyridone ester (9), which is typically isolated by filtration, and further purified, if desired, by standard methods such as chromatography or crystallization. Suitable alkylating agents include alkyl halides, alkyl sulfonates and alkyl sulfates.

In Scheme 2, Step B, the 4-chloropyridone ester (9) is hydrolyzed to the carboxylic acid (10) by treatment with a base such as sodium hydroxide in aqueous tetrahydrofuran, ethanol, or acetonitrile.

In Scheme 2, Step C, the 4-(arylamino)pyridone acid (6) is prepared from the coupling of the 4-chloropyridone acid (10) and a suitable aniline (2) in the presence of a strong base, for example, lithium bis(trimethylsilyl)amide or lithium diisopropylamide, in a polar aprotic solvent such as tetrahydrofuran, acetonitrile or dimethylformamide. For example, the aniline (2) and the 4-chloropyridone acid (10) are dissolved in a suitable organic solvent and cooled to about −78° C. under nitrogen. The suspension is treated with an excess of a suitable base, such as LiHMDS, and allowed to warm to room temperature. The reaction is typically complete within about 2 hours to about 5 days. The resulting pyridone acid (6) can be isolated by removing the solvent, for example by evaporation under reduced pressure or by filtering the precipitated solid through Celite® and washing with a suitable solvent. The pyridone acid (6) can be further purified, if desired, by standard methods such as chromatography, crystallization, or distillation.

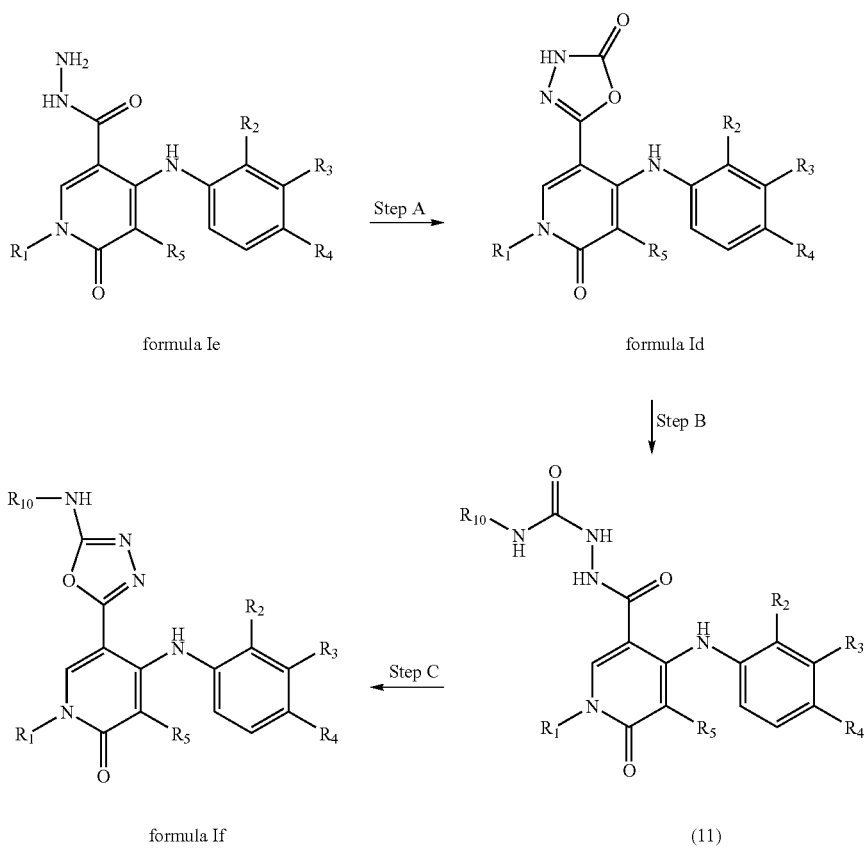

In Scheme 3, Step A, an acyl hydrazide of formula Ie is converted to an oxadiazolinone of formula Id. A preferred reagent is carbonyldiimidazole in polar aprotic solvents such as dimethylformamide.

In Scheme 3, Step B, ureas (11) are obtained by the union of oxadiazolinone (Id) with an alkyl amine or substituted alkylamine. Preferred solvents for this transformation include pyridine, isopropanol and ethanol at temperatures between 80° C. and 120° C. Reactions are generally complete between 1 h and 5 days.

In step C, the urea (11) is subjected to conditions of cyclodehydration to afford oxadiazoles of formula If. Preferred conditions for this transformation are the combination of carbon tetrachloride and triphenyphosphine (or polymer-supported triphenylphoshine) and a base such as triethylamine. Preferred solvents for this transformation include dichloromethane or 1,2-dichloroethane at temperatures between 35° C. and 100° C. During the cyclodehydration step, hydroxyl or amino substituents on the $R_{10}$ alkyl chain may be chemically protected, if necessary, using protecting groups familiar to those skilled in the art. Accordingly, a protection/deprotection sequence, if necessary, is implicit in Step C. For hydroxyl substituents on $R_{10}$, preferred protecting groups include silyl ethers, for example tert-butyldimethylsilyl ethers, triethylsilyl ethers, or triisopropylsilyl ethers. Such silyl ethers are chemically removed using fluoride. Preferred reagents for this deprotection include tetrabutylamonium fluoride or cesium fluoride.

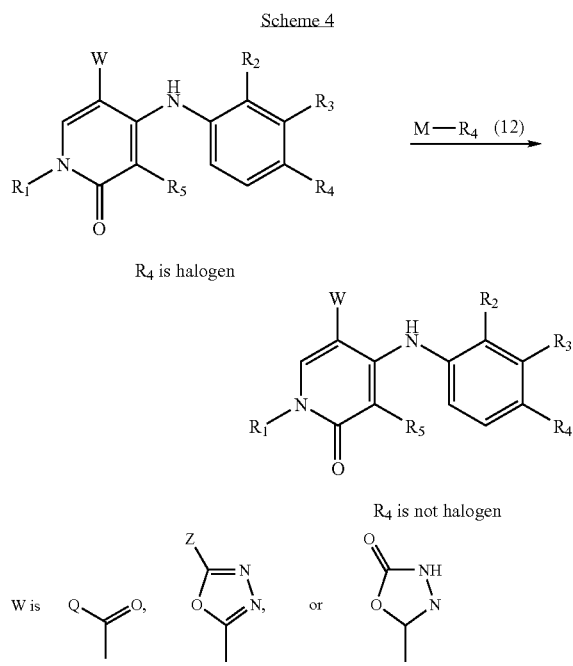

In Scheme 4, the compounds of formula I, wherein $R_4$ is not halogen are prepared from the compounds of formula I wherein $R_4$ is halogen, by transition metal-promoted coupling with reagent M-$R_4$ wherein $R_4$ is non-halogen (12) in a suitable solvent or solvents such as triethylamine, tetrahydrofuran or dimethylformamide. The transition metal-promoted coupling may be carried out with a palladium(0) or palladium (II) coupling agent, such as $(Ph_3P)_4Pd$ or $(Ph_3P)_2PdCl_2$. The entire mixture is stirred from about 2 to 24 hours at room temperature. M is defined as a functional group known to transfer a carbon radical fragment in transition metal-promoted coupling processes. Examples of a suitable M group include trialkylstannyl, trialkylsilyl, trimethylsilyl, zinc, tin, copper, boron, magnesium and lithium.

Examples of a suitable M-$R_4$ reagent (12) when, $R_4$ is $C_{2-4}$ alkenyl is allyltributyltin or tetravinyltin, and when $R_4$ is hydroxy-substituted $C_{2-6}$ alkynyl is propargyl alcohol. Preferred halogens, when $R_4$ is halogen, are bromine and iodine.

The resulting compound of formula I, as well as the protected Formula I compound, can be isolated by removing the solvent, for example by evaporation under reduced pressure, and further purified, if desired, by standard methods such as chromatography, crystallization, or distillation.

It would be understood by one of skill in the art that the substituent $R_4$, when $R_4$ is non-halogen, may be further transformed, such as by oxidation, reduction, deprotection, or hydrogenation.

A compound wherein $R_4$ is $C_{2-4}$ alkenyl may be transformed to a compound wherein $R_4$ is hydroxy-substituted alkyl by treating the double bond of the alkene with ozone and $NaBH_4$. Furthermore, a compound wherein $R_4$ is $C_{2-4}$ alkenyl may be transformed to a compound wherein $R_4$ is alkyl substituted with 2 hydroxy substituents by treating the double bond of the alkene with $OsO_4$.

A compound wherein $R_4$ is an alkene or alkyne derivative may be reduced under conditions known in the art, such as through hydrogenation, such as with Pd/C under an atmosphere of hydrogen. For example, the alkyne derivative is dissolved in a suitable solvent, such as absolute ethanol, in the presence of a metal catalyst, such as palladium on carbon. This mixture is stirred under an atmosphere of hydrogen from about 1 to 24 hours at room temperature to provide the fully saturated derivative. Alternately, the alkyne derivative is partially reduced via hydrogenation to provide the alkene derivative. For example, the alkyne derivative is dissolved in a suitable solvent, such as tetrahydrofuran, in the presence of a catalyst, such as Lindlar catalyst or palladium on carbon and, if desired, a suitable compound which disrupts the actions of the catalyst, such as quinoline or pyridine. This mixture is stirred under an atmosphere of hydrogen from about 1 to 24 hours at room temperature to provide the alkene derivative.

The substituent $R_4$ may also be transformed into a different $R_4$ through standard synthetic procedures known to one of skill in the art.

It would be understood by one of skill in the art that the transformation of $R_4$ as shown in Scheme 4 may be performed at various steps throughout the synthesis of compounds of the present invention, as desired. For example, $R_4$ may be transformed before the coupling of the ester (1) and aniline (2) as shown in Scheme 1, Step A, or before or after the coupling as shown in Scheme 1, Step F.

Further transformations of $R_4$ are shown in Scheme 5 below.

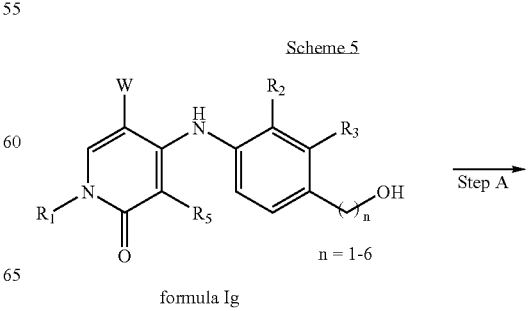

-continued

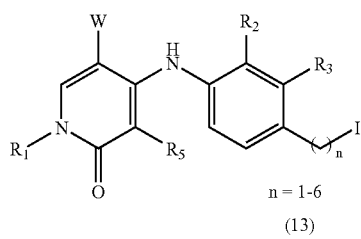

(13)

Step B

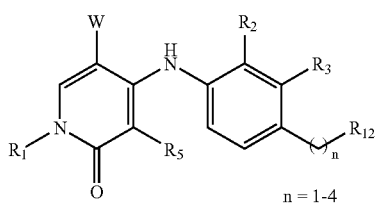

formula Ih $R_{12}$ is $NR_6R_7$ or $OR_6$

In Scheme 5, step A, the compound of formula Ig is dissolved in a suitable solvent such as tetrahydrofuran and reacted with methanesulfonyl chloride to give the intermediate mesylate, then NaI in EtOAc to give the iodide compound (13).

In Scheme 5, step B, the iodide compound (13) is reacted with a suitable amine, such as methylamine or dimethylamine, or a suitable alkoxide to give compounds of formula Ih.

It would also be understood by one of skill in the art that the aniline may be prepared to include the desired $R_4$.

The aniline (2) can be prepared by techniques and procedures readily available to one of ordinary skill in the art and by following the procedures as set forth in the following Schemes, or analogous variants thereof. These Schemes are not intended to limit the scope of the invention in any way.

Scheme 6

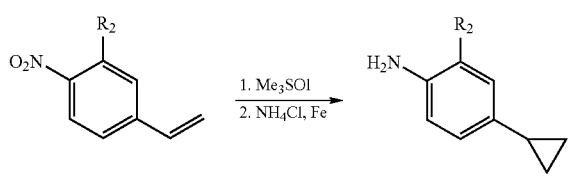

Bull. Soc. Chim. Belg., 95(2), 135-8; 1986

In Scheme 6, a suitably substituted para-nitrostyrene is reacted with dimethyloxosulfonium methylide to form the substituted para-nitrocyclopropylbenzene. Reduction of para-nitrocyclopropylbenzene with iron in the presence of weak acid gives the desired aniline.

Scheme 7

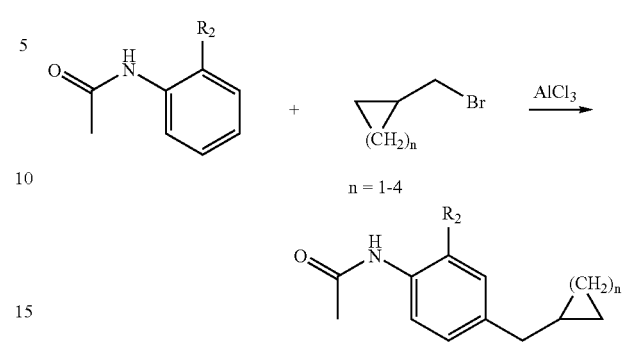

In Scheme 7, the suitable ortho-substituted acetamide is reacted with bromocyclobutane, bromocyclopropane, or bromocyclohexane under typical Friedel-Craft conditions, as known to one of skill in the art, to give the desired para-cycloalkylanilines. The acetamide is deprotected under conditions known to one of skill in the art to provide the desired para-cycloalkylmethylanilines.

Scheme 8

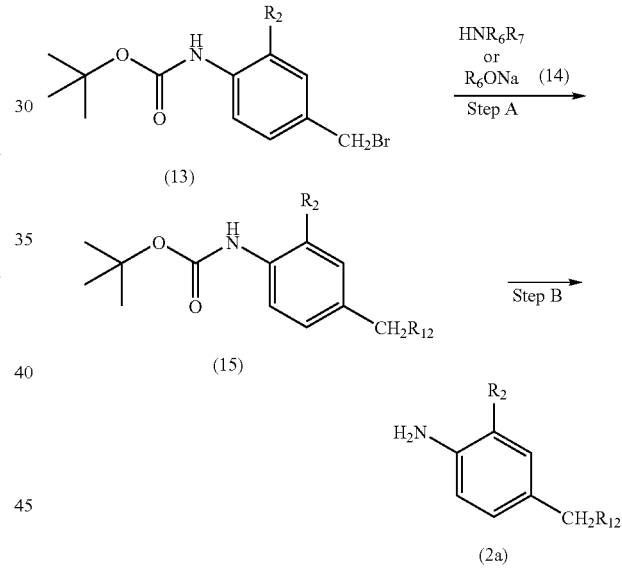

In Scheme 8, Step A, a suitable amine or alkoxide (14) is reacted with a 4-tert-butoxycarbonylamino-3-substituted-benzyl bromide (13), such as 4-tert-butoxycarbonylamino-3-fluorobenzyl bromide (*J. Med. Chem.*, 2000, 43:5017). In Step B, the BOC protecting group of compound of structure (15) is hydrolyzed with, for example, TFA, to provide the desired aniline (2a).

Scheme 9

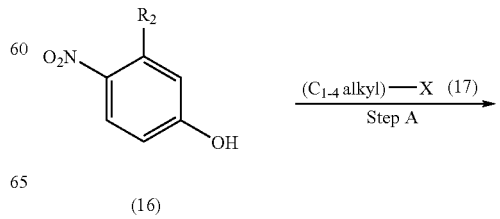

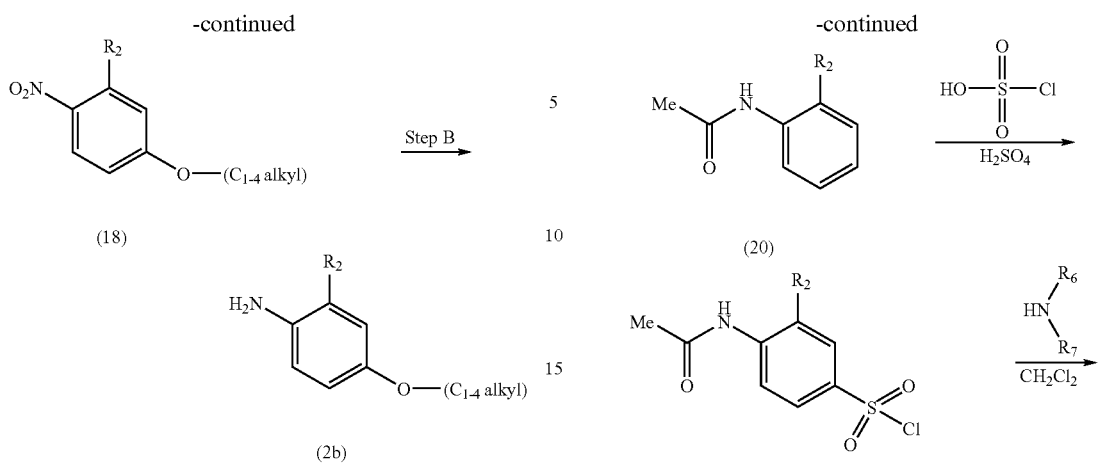

(18)

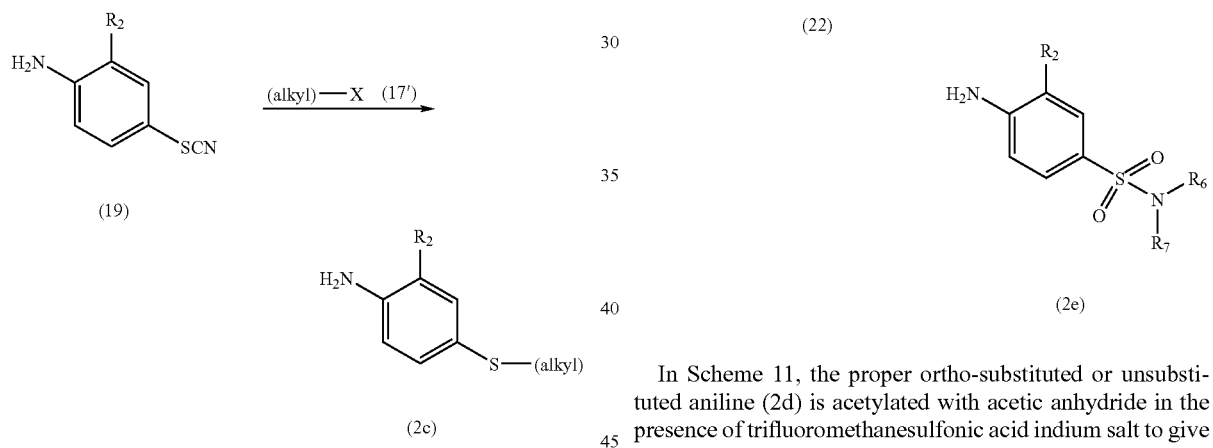

(2b)

In Scheme 9, Step A, a suitable 3-substituted-4-nitrophenol (16), such as 3-fluoro-4-nitrophenol, is alkylated with a compound of structure (17) in the presence of a suitable base to provide a compound of structure (18). In Step B, compound (18) is reduced via hydrogenation in the presence of a metal catalyst, such as palladium on carbon, in an atmosphere of hydrogen to provide the desired aniline (2b).

Scheme 10

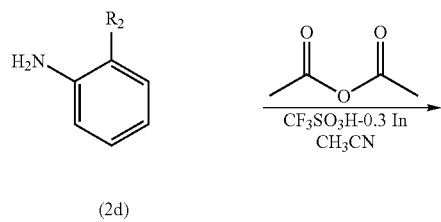

In Scheme 10, a suitable 4-(aminophenyl)thiocyanate (19), is alkylated with a compound of structure (17') in the presence of a suitable nucleophilic base to provide an alkylthio compound of structure (2c). After reaction under standard conditions to form the diphenylamine (3), wherein $R_4$ is —S-(alkyl), as in Scheme 1 above, this compound is then oxidized to the corresponding sulfonyl compound, also generally, the diphenylamine (3), wherein $R_4$ is —SO$_2$-(alkyl).

Scheme 11

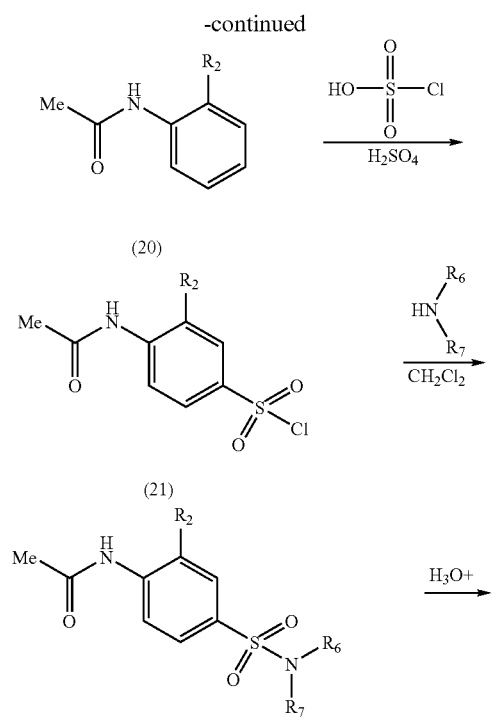

Synlett, (11), 1743-1744; 1999

In Scheme 11, the proper ortho-substituted or unsubstituted aniline (2d) is acetylated with acetic anhydride in the presence of trifluoromethanesulfonic acid indium salt to give the protected aniline (20). Chlorosulfonation in the typical manner, as known in the art, gives the sulfonyl chloride derivative (21) which is reacted with an excess of a suitable amine in a solvent such as dichloromethane or dichloroethane to give the protected para-aminobenzenesulfonamide (22). Acid-mediated deprotection in the appropriate solvent gives the desired aniline (2e).

Alternatively, the desired aniline (2e) wherein $R_2$ is methyl, fluorine or chlorine, using compound (21) as the starting material can be prepared. Where $R_2$ is fluorine, the sulfonyl chloride derivative (21) is a compound known in the literature (German Patent DE 2630060, 1978). Similarly, where $R_2$ is methyl, the sulfonyl chloride derivative (21) is also known in the literature (German Patent, DE 2750170, 1978). Finally, the sulfonyl chloride derivative (21) where $R_2$ is chlorine is commercially available.

In addition to the procedure described in Scheme 11, one of ordinary skill in the art would appreciate that there are numerous ways of acetylating anilines. For example, heating the aniline and acetic anhydride together in a suitable solvent, such as acetic acid, would achieve the same result.

Compounds of the present invention include, but are not limited to the following compounds:

4-(2-Fluoro-4-iodoanilino)-N-(2-hydroxyethoxy)-1-methyl-6-oxo-1,6-dihydro-3-pyridinecarboxamide;

4-[2-Fluoro-4-(3-hydroxy-1-propynyl)anilino]-N-(2-hydroxyethoxy)-1-methyl-6-oxo-1,6-dihydro-3-pyridinecarboxamide;

4-[2-Fluoro-4-(3-hydroxypropyl)anilino]-N-(2-hydroxyethoxy)-1-methyl-6-oxo-1,6-dihydro-3-pyridinecarboxamide;

4-(2-Fluoro-4-iodoanilino)-N-(2-hydroxyethyl)-1-methyl-6-oxo-1,6-dihydro-3-pyridinecarboxamide;

4-(2-Fluoro-4-iodoanilino)-N-(3-hydroxypropyl)-1-methyl-6-oxo-1,6-dihydro-3-pyridinecarboxamide;

4-[2-Fluoro-4-(3-hydroxy-1-propynyl)anilino]-N-(2-hydroxyethyl)-1-methyl-6-oxo-1,6-dihydro-3-pyridinecarboxamide;

4-[2-Fluoro-4-(3-hydroxypropyl)anilino]-N-(2-hydroxyethyl)-1-methyl-6-oxo-1,6-dihydro-3-pyridinecarboxamide;

4-[2-Fluoro-4-(3-hydroxy-1-propynyl)anilino]-N-(3-hydroxypropyl)-1-methyl-6-oxo-1,6-dihydro-3-pyridinecarboxamide;

4-[2-Fluoro-4-(3-hydroxypropyl)anilino]-N-(3-hydroxypropyl)-1-methyl-6-oxo-1,6-dihydro-3-pyridinecarboxamide;

4-(2-Fluoro-4-iodoanilino)-1-methyl-6-oxo-1,6-dihydro-3-pyridinecarboxamide;

4-(2-Fluoro-4-iodoanilino)-N-(2-hydroxyethyl)-6-oxo-1,6-dihydro-3-pyridinecarboxamide;

4-(4-Ethynyl-2-fluoroanilino)-N-(2-hydroxyethyl)-6-oxo-1,6-dihydro-3-pyridinecarboxamide;

4-(4-Ethyl-2-fluoroanilino)-N-(2-hydroxyethyl)-6-oxo-1,6-dihydro-3-pyridinecarboxamide;

4-(2-Fluoro-4-iodoanilino)-N-(3-hydroxypropyl)-6-oxo-1,6-dihydro-3-pyridinecarboxamide;

4-(4-Ethynyl-2-fluoroanilino)-N-(3-hydroxypropyl)-6-oxo-1,6-dihydro-3-pyridinecarboxamide;

4-(4-Ethyl-2-fluoroanilino)-N-(3-hydroxypropyl)-6-oxo-1,6-dihydro-3-pyridinecarboxamide;

4-(4-Ethynyl-2-fluoroanilino)-1-methyl-6-oxo-1,6-dihydro-3-pyridinecarboxamide;

4-(4-Ethyl-2-fluoroanilino)-1-methyl-6-oxo-1,6-dihydro-3-pyridinecarboxamide;

4-(2-Fluoro-4-iodoanilino)-6-oxo-1,6-dihydro-3-pyridinecarboxamide;

4-[2-Fluoro-4-(3-hydroxy-1-propynyl)anilino]-1-methyl-6-oxo-1,6-dihydro-3-pyridinecarboxamide;

4-[2-Fluoro-4-(3-hydroxypropyl)anilino]-1-methyl-6-oxo-1,6-dihydro-3-pyridinecarboxamide;

4-(2-Fluoro-4-iodoanilino)-1-(2-hydroxyethyl)-6-oxo-1,6-dihydro-3-pyridinecarboxamide;

4-(2-Fluoro-4-iodoanilino)-1-(2-hydroxyethyl)-N-(3-hydroxypropyl)-6-oxo-1,6-dihydro-3-pyridinecarboxamide;

(4-(2-Fluoro-4-iodoanilino)-5-{[(3-hydroxypropyl)amino]carbonyl}-2-oxo-1(2H)-pyridinyl)acetic acid;

5-(Aminocarbonyl)-4-(2-fluoro-4-iodoanilino)-2-oxo-1(2H)-pyridinyl)acetic acid;

1-(3-Cyanopropyl)-4-(2-fluoro-4-iodoanilino)-6-oxo-1,6-dihydro-3-pyridinecarboxamide;

1-Ethyl-4-(2-fluoro-4-iodoanilino)-6-oxo-1,6-dihydro-3-pyridinecarboxamide;

4-(2-Fluoro-4-iodoanilino)-6-oxo-1-propyl-1,6-dihydro-3-pyridinecarboxamide;

4-(2-Fluoro-4-iodoanilino)-1-[2-(2-methoxyethoxy)ethyl]-6-oxo-1,6-dihydro-3-pyridinecarboxamide;

1-Allyl-4-(2-fluoro-4-iodoanilino)-6-oxo-1,6-dihydro-3-pyridinecarboxamide;

1-(2,3-Dihydroxypropyl)-4-(2-fluoro-4-iodoanilino)-6-oxo-1,6-dihydro-3-pyridinecarboxamide;

4-(2-Fluoro-4-iodoanilino)-1-(3-hydroxypropyl)-6-oxo-1,6-dihydro-3-pyridinecarboxamide;

4-(2,4-Difluoroanilino)-N-(2-hydroxyethoxy)-1-methyl-6-oxo-1,6-dihydro-3-pyridinecarboxamide;

4-(2,4-Difluoroanilino)-N-(3-hydroxypropyl)-1-methyl-6-oxo-1,6-dihydro-3-pyridinecarboxamide;

4-(2-Fluoro-4-methylanilino)-N-(2-hydroxyethoxy)-1-methyl-6-oxo-1,6-dihydro-3-pyridinecarboxamide;

4-(2-Fluoro-4-methylanilino)-N-(3-hydroxypropyl)-1-methyl-6-oxo-1,6-dihydro-3-pyridinecarboxamide;

4-(2-Fluoro-4-methylanilino)-1-methyl-6-oxo-1,6-dihydro-3-pyridinecarboxamide;

4-(4-Bromo-2-fluoroanilino)-N-(2-hydroxyethoxy)-1-methyl-6-oxo-1,6-dihydro-3-pyridinecarboxamide;

4-(4-Bromo-2-fluoroanilino)-N-(3-hydroxypropyl)-1-methyl-6-oxo-1,6-dihydro-3-pyridinecarboxamide;

4-(4-Bromo-2-fluoroanilino)-1-methyl-6-oxo-1,6-dihydro-3-pyridinecarboxamide;

4-[2-Fluoro-4-(1,1,2,2,3,3,4,4,4-nonafluorobutyl)anilino]-1-methyl-6-oxo-1,6-dihydro-3-pyridinecarboxamide;

N-(3-Hydroxypropyl)-1-methyl-4-(2-naphthylamino)-6-oxo-1,6-dihydro-3-pyridinecarboxamide;

1-Methyl-4-(2-naphthylamino)-6-oxo-1,6-dihydro-3-pyridinecarboxamide;

4-[(1-Chloro-2-naphthyl)amino]-N-(2-hydroxyethoxy)-1-methyl-6-oxo-1,6-dihydro-3-pyridinecarboxamide;

N-(2,3-Dihydroxypropyl)-4-(2-fluoro-4-iodoanilino)-1-methyl-6-oxo-1,6-dihydro-3-pyridinecarboxamide;

4-(2-Fluoro-4-iodoanilino)-N-[2-hydroxy-1-(hydroxymethyl)ethyl]-1-methyl-6-oxo-1,6-dihydro-3-pyridinecarboxamide;

4-(2-Fluoro-4-iodoanilino)-N-[2-hydroxy-1,1-bis(hydroxymethyl)ethyl]-1-methyl-6-oxo-1,6-dihydro-3-pyridinecarboxamide;

2-Amino-3-hydroxy-2-(hydroxymethyl)propyl-4-(2-fluoro-4-iodoanilino)-1-methyl-6-oxo-1,6-dihydro-3-pyridinecarboxylate;

4-(2-Fluoro-4-iodoanilino)-N-(2-hydroxy-1-methylethyl)-1-methyl-6-oxo-1,6-dihydro-3-pyridinecarboxamide;

4-(2-Fluoro-4-iodoanilino)-N-(2-hydroxypropyl)-1-methyl-6-oxo-1,6-dihydro-3-pyridinecarboxamide;

4-(2-Fluoro-4-iodoanilino)-N,1-dimethyl-6-oxo-1,6-dihydro-3-pyridinecarboxamide;

4-(2-Fluoro-4-iodoanilino)-N,N,1-trimethyl-6-oxo-1,6-dihydro-3-pyridinecarboxamide;

N-(3-Aminopropyl)-4-(2-fluoro-4-iodoanilino)-1-methyl-6-oxo-1,6-dihydro-3-pyridinecarboxamide;

4-(4-Cyano-2-fluoroanilino)-1-methyl-6-oxo-1,6-dihydro-3-pyridinecarboxamide;

4-(2-fluoro-4-iodoanilino)-1-methyl-6-oxo-1,6-dihydro-3-pyridinecarboxylic acid;

4-(3,4-Dichloro-phenylamino)-1-methyl-6-oxo-1,6-dihydro-pyridine-3-carboxylic acid amide;

4-(3,4-Dimethyl-phenylamino)-1-methyl-6-oxo-1,6-dihydro-pyridine-3-carboxylic acid ethyl ester;

4-(Indan-5-ylamino)-1-methyl-6-oxo-1,6-dihydro-pyridine-3-carboxylic acid ethyl ester;

1-Methyl-6-oxo-4-(2,3,4-trichloro-phenylamino)-1,6-dihydro-pyridine-3-carboxylic acid ethyl ester;

4-(4-Chloro-3-trifluoromethyl-phenylamino)-1-methyl-6-oxo-1,6-dihydro-pyridine-3-carboxylic acid ethyl ester;

4-(1H-Indol-5-ylamino)-1-methyl-6-oxo-1,6-dihydro-pyridine-3-carboxylic acid ethyl ester;

4-(1H-Indazol-5-ylamino)-1-methyl-6-oxo-1,6-dihydro-pyridine-3-carboxylic acid ethyl ester;

4-(3,4-Dimethyl-phenylamino)-1-methyl-6-oxo-1,6-dihydro-pyridine-3-carboxylic acid;

4-(Indan-5-ylamino)-1-methyl-6-oxo-1,6-dihydro-pyridine-3-carboxylic acid;

1-Methyl-6-oxo-4-(2,3,4-trichloro-phenylamino)-1,6-dihydro-pyridine-3-carboxylic acid;

4-(4-Chloro-3-trifluoromethyl-phenylamino)-1-methyl-6-oxo-1,6-dihydro-pyridine-3-carboxylic acid;

4-(3,4-Dimethyl-phenylamino)-1-methyl-6-oxo-1,6-dihydro-pyridine-3-carboxylic acid amide;

4-(Indan-5-ylamino)-1-methyl-6-oxo-1,6-dihydro-pyridine-3-carboxylic acid amide;

4-(4-Chloro-3-trifluoromethyl-phenylamino)-1-methyl-6-oxo-1,6-dihydro-pyridine-3-carboxylic acid amide;

1-Methyl-6-oxo-4-(2,3,4-trichloro-phenylamino)-1,6-dihydro-pyridine-3-carboxylic acid amide;

4-(2-Fluoro-4-iodo-phenylamino)-1-methyl-6-oxo-1,6-dihydro-pyridine-3-carboxylic acid;

4-(2-Fluoro-4-iodo-phenylamino)-1-methyl-6-oxo-1,6-dihydro-pyridine-3-carboxylic acid amide;

4-(2-Fluoro-4-methyl-phenylamino)-1-methyl-6-oxo-1,6-dihydro-pyridine-3-carboxylic acid ethyl ester;

4-(2-Fluoro-4-iodo-phenylamino)-1-methyl-6-oxo-1,6-dihydro-pyridine-3-carboxylic acid ethyl ester;

4-(2-Fluoro-4-iodo-phenylamino)-1-methyl-6-oxo-1,6-dihydro-pyridine-3-carboxylic acid ethyl ester;

4-(4-Ethynyl-2-fluoro-phenylamino)-1-methyl-6-oxo-1,6-dihydro-pyridine-3-carboxylic acid ethyl ester;

4-(4-Ethynyl-2-fluoro-phenylamino)-1-methyl-6-oxo-1,6-dihydro-pyridine-3-carboxylic acid (2-hydroxy-ethyl)-amide;

4-(4-Ethynyl-2-fluoro-phenylamino)-1-methyl-6-oxo-1,6-dihydro-pyridine-3-carboxylic acid (2-hydroxy-1-hydroxymethyl-ethyl)-amide;

4-(4-Ethynyl-2-fluoro-phenylamino)-1-methyl-6-oxo-1,6-dihydro-pyridine-3-carboxylic acid (2,3-dihydroxy-propyl)-amide;

4-(4-Ethyl-2-fluoro-phenylamino)-1-methyl-6-oxo-1,6-dihydro-pyridine-3-carboxylic acid (2-hydroxy-ethyl)-amide;

4-(4-Ethyl-2-fluoro-phenylamino)-1-methyl-6-oxo-1,6-dihydro-pyridine-3-carboxylic acid (2-hydroxy-1-hydroxymethyl-ethyl)-amide;

4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(4-Ethyl-2-fluoro-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-1-methyl-6-oxo-1,6-dihydro-pyridine-3-carboxylic acid;

4-(2-Fluoro-4-methylsulfanyl-phenylamino)-1-methyl-6-oxo-1,6-dihydro-pyridine-3-carboxylic acid (3-hydroxy-propyl)-amide;

4-(2-Fluoro-4-methylsulfanyl-phenylamino)-1-methyl-6-oxo-1,6-dihydro-pyridine-3-carboxylic acid amide;

4-(2-Fluoro-4-methylsulfanyl-phenylamino)-1-methyl-6-oxo-1,6-dihydro-pyridine-3-carboxylic acid (2-hydroxy-ethyl)-amide;

4-(2-Fluoro-4-methylsulfanyl-phenylamino)-1-methyl-6-oxo-1,6-dihydro-pyridine-3-carboxylic acid (2,3-dihydroxy-propyl)-amide;

4-(2-Fluoro-4-methylsulfanyl-phenylamino)-1-methyl-6-oxo-1,6-dihydro-pyridine-3-carboxylic acid (2-hydroxy-1-hydroxymethyl-ethyl)-amide;

4-(2-Fluoro-4-methylsulfanyl-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-5-[5-(2-hydroxy-1-hydroxymethyl-ethylamino)-[1,3,4]oxadiazol-2-yl]-1-methyl-1H-pyridin-2-one;

5-[5-(2,3-Dihydroxy-propylamino)-[1,3,4]oxadiazol-2-yl]-4-(2-fluoro-4-methylsulfanyl-phenylamino)-1-methyl-1H-pyridin-2-one;

4-(4-Ethynyl-2-fluoro-phenylamino)-5-[5-(2-hydroxy-ethylamino)-[1,3,4]oxadiazol-2-yl]-1-methyl-1H-pyridin-2-one;

4-(4-Ethynyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(2-Fluoro-4-methanesulfinyl-phenylamino)-1-methyl-6-oxo-1,6-dihydro-pyridine-3-carboxylic acid (2-hydroxy-1-hydroxymethyl-ethyl)-amide;

4-(2-Fluoro-4-iodo-phenylamino)-1-methyl-6-oxo-1,6-dihydro-pyridine-3-carboxylic acid hydrazide;

4-(4-Ethynyl-2-fluoro-phenylamino)-1-methyl-6-oxo-1,6-dihydro-pyridine-3-carboxylic acid;

4-(4-Ethyl-2-fluoro-phenylamino)-1-methyl-6-oxo-1,6-dihydro-pyridine-3-carboxylic acid ethyl ester;

4-(4-Ethyl-2-fluoro-phenylamino)-1-methyl-6-oxo-1,6-dihydro-pyridine-3-carboxylic acid;

4-(2-Fluoro-4-iodo-phenylamino)-1-methyl-5-(5-oxo-4,5-dihydro-[1,3,4]oxadiazol-2-yl)-1H-pyridin-2-one; and 4-(4-Ethyl-2-fluoro-phenylamino)-1-methyl-6-oxo-1,6-dihydro-pyridine-3-carboxylic acid amide.

As used herein, the term "patient" refers to any warm-blooded animal such as, but not limited to, a human, horse, dog, guinea pig, or mouse. Preferably, the patient is human.

The term "treating" for purposes of the present invention refers to treatment, prophylaxis or prevention, amelioration or elimination of a named condition once the condition has been established.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ for one or more of the above-named enzymes.

The disclosed compositions are useful as both prophylactic and therapeutic treatments for diseases or conditions related to the hyperactivity of MEK, as well as diseases or conditions modulated by the MEK cascade. Examples include, but are not limited to, stroke, septic shock, heart failure, osteoarthritis, rheumatoid arthritis, organ transplant rejection, and a variety of tumors such as ovarian, lung, pancreatic, brain, prostatic, and colorectal.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include brain, breast, lung, such as non-small cell lung, ovarian, pancreatic, prostate, renal, colorectal, cervical, acute leukemia, and gastric cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, Alzheimer's disease, and chronic or neuropathic pain. Compounds of the invention are also useful as antiviral agents for treating viral infections such as HIV, hepatitis (B) virus (HBV), human papilloma virus (HPV), cytomegalovirus (CMV), and Epstein-Barr virus (EBV). These methods include the step of administering to a patient in need of such treatment, or suffering from such a disease or condition, a therapeutically effective amount of a disclosed compound of formula I or pharmaceutical composition thereof.

The term "chronic pain" for purposes of the present invention includes, but is not limited to, neuropathic pain, idiopathic pain, and pain associated with chronic alcoholism, vitamin deficiency, uremia, or hypothyroidism. Chronic pain is associated with numerous conditions including, but not limited to, inflammation, arthritis, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine.

The chemotherapy or radiation therapy may be administered before, concurrently, or after the administration of a disclosed compound according to the needs of the patient.

Those skilled in the art will be able to determine, according to known methods, the appropriate therapeutically-effective amount or dosage of a compound of the present invention to administer to a patient, taking into account factors such as age, weight, general health, the compound administered, the route of administration, the type of pain or condition requiring treatment, and the presence of other medications. In general, an effective amount or a therapeutically-effective amount will be between about 0.1 and about 1000 mg/kg per day, preferably between about 1 and about 300 mg/kg body weight, and daily dosages will be between about 10 and about 5000 mg for an adult subject of normal weight. Commercially available capsules or other formulations (such as liquids and film-coated tablets) of 100, 200, 300, or 400 mg can be administered according to the disclosed methods.

The compounds of the present invention are preferably formulated prior to administration. Therefore, another aspect of the present invention is a pharmaceutical composition comprising a compound of Formula I and a pharmaceutically acceptable carrier. In making the compositions of the present invention, the active ingredient, such as a compound of Formula I, will usually be mixed with a carrier, or diluted by a carrier or enclosed within a carrier. Dosage unit forms or pharmaceutical compositions include tablets, capsules, pills, powders, granules, aqueous and nonaqueous oral solutions and suspensions, and parenteral solutions packaged in containers adapted for subdivision into individual doses.

Dosage unit forms can be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accceperators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

The following examples represent typical syntheses of the compounds of the present invention as described generally above. These examples are illustrative only and are not intended to limit the invention in any way. The reagents and starting materials are readily available to one of ordinary skill in the art.

EXAMPLE 1

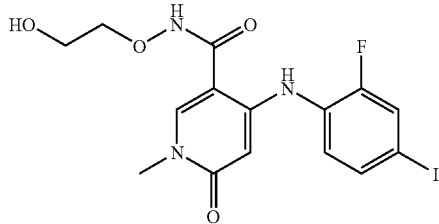

4-(2-Fluoro-4-iodoanilino)-N-(2-hydroxyethoxy)-1-methyl-6-oxo-1,6-dihydro-3-pyridinecarboxamide

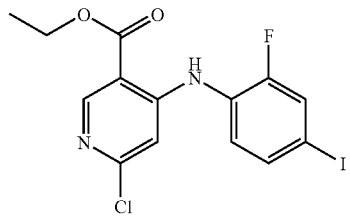

Step A: Preparation of ethyl 6-chloro-4-(2-fluoro-4-iodoanilino)nicotinate

Ethyl 4,6-dichloronicotinate [prepared according to the literature procedure of *J. Chem. Soc.* 5163 (1963)] (4.00 g, 18.2 mmol) and 2-fluoro-4-iodoaniline (4.30 g, 18.2 mmol) were dissolved in EtOH (80 mL), to which was added conc. HCl (6 drops). This mixture was heated, in an oil bath at 90° C., for 15 h. The solution was allowed to cool, then refrigerated whereupon the desired product crystallised out of solution as fine needles. The product was isolated by filtration and washed with 10% Et$_2$O/hexanes to give ethyl 6-chloro-4-(2-fluoro-4-iodoanilino)nicotinate as white needles (3.79 g, 50%), m.p. (EtOAc/n-hexane) 162-164° C. $^1$H NMR [(CD$_3$)$_2$SO, 400 MHz] δ 9.62 (s, 1H), 8.69 (s, 1H), 7.82 (dd, J=9.9, 1.9 Hz, 1H), 7.61-7.66 (m, 1H), 7.33 (t, J=8.5 Hz, 1H), 6.67 (d, J=1.8 Hz, 1H), 4.37 (q, J=7.1 Hz, 2H), 1.35 (t, J=7.1 Hz, 3H). Anal. Calcd for C$_{14}$H$_{11}$ClFIN$_2$O$_2$: C, 40.0; H, 2.6; N, 6.7. Found: C, 40.3; H, 2.2; N, 6.7.

Alternate Step A: Preparation of ethyl 6-chloro-4-(2-fluoro-4-iodoanilino)nicotinate Ethyl 4,6-dichloronicotinate (18.60 g, 84.40 mmol) and 2-fluoro-4-iodoaniline (20.0 g, 84.40 mmol) were dissolved in EtOH (80 mL), to which was added conc. HCl (6 drops). This mixture was heated, in an oil bath at 90° C., for 24 h. The solvent was evaporated under reduced pressure. The residue was partitioned between water (100 mL) and EtOAc (400 mL). The organic layer was washed sequentially with saturated NaHCO$_3$ and saturated NaCl, dried over MgSO$_4$, filtered, and concentrated in vacuo. The residue was purified on SiO$_2$ using flash chromatography (eluent:5-10% EtOAc/Hexanes) to afford ethyl 6-chloro-4-(2-fluoro-4-iodoanilino) nicotinate as an off white solid (22.0 g, 62%). $^1$H NMR [(CD$_3$)$_2$SO, 400 MHz] δ 9.62 (s, 1H), 8.69 (s, 1H), 7.82 (dd, J=9.9, 1.9 Hz, 1H), 7.61-7.66 (m, 1H), 7.33 (t, J=8.5 Hz, 1H), 6.67 (d, J=1.8 Hz, 1H), 4.37 (q, J=7.1 Hz, 2H), 1.35 (t, J=7.1 Hz, 3H). Anal. Calcd for C$_{14}$H$_{11}$ClFIN$_2$O$_2$: C, 39.98; H, 2.64; N, 6.66. Found: C, 40.4; H, 2.38; N, 6.59.

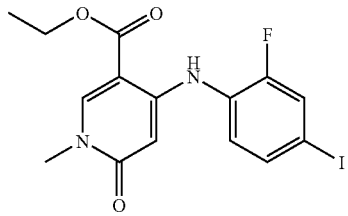

Step B: Preparation of ethyl 4-(2-fluoro-4-iodoanilino)-1-methyl-6-oxo-1,6-dihydro-3-pyridinecarboxylate Ethyl 6-chloro-4-(2-fluoro-4-iodoanilino)nicotinate (200 mg, 0.48 mmol) was dissolved in CHCl$_3$ (5 mL) and the solution cooled (ice/water). Dimethyl sulfate (0.27 mL, 2.86 mmol) was added, the solution allowed to warm to R.T., then heated at reflux for 20 h. The reaction mixture was allowed to cool to R.T., then a mixture of triethylamine (1.41 mL), acetic acid (0.94 mL) and EtOH (0.94 mL) was added and the reaction heated at reflux for a further 2 h. After cooling, water (10 mL) was added and the mixture was partitioned between EtOAc (100 mL) and water (50 mL). The EtOAc layer was washed with further water (50 mL) and brine (50 mL), then dried (Na$_2$SO$_4$). The solvent was removed under reduced pressure and the resulting residue purified by chromatography on silica gel (50% EtOAc/hexanes as eluant), giving ethyl 4-(2-fluoro-4-iodoanilino)-1-methyl-6-oxo-1,6-dihydro-3-pyridinecarboxylate as a white solid (143 mg, 72%), m.p. (EtOAc/n-hexane) 169-170° C. $^1$H NMR [(CD$_3$)$_2$SO, 400 MHz] δ 9.31 (s, 1H), 8.54 (s, 1H), 7.77 (dd, J=10.1, 1.9 Hz, 1H), 7.60 (br dd, J=8.3, 1.0 Hz, 1H), 7.30 (t, J=8.5 Hz, 1H), 5.46 (s, 1H), 4.30 (q, J=7.1 Hz, 2H), 3.43 (s, 3H), 1.32 (t, J=7.1 Hz, 3H). Anal. Calcd for C$_{15}$H$_{14}$FIN$_2$O$_3$: C, 43.3; H, 3.4; N, 6.7. Found: C, 43.7; H, 3.1; N, 7.0.

Alternate Step B:

4-(2-Fluoro-4-iodo-phenylamino)-1-methyl-6-oxo-1,6-dihydro-pyridine-3-carboxylic acid ethyl ester 6-Chloro-4-(2-fluoro-4-iodo-phenylamino)-nicotinic acid ethyl ester (15.0 g, 35.70 mmol) was dissolved in CHCl$_3$ (100 mL) and the solution cooled (ice/water). Dimethyl sulfate (20.25 mL, 214.0 mmol) was added, the solution allowed to warm to room temperature then heated at reflux for 20 h. The reaction mixture was allowed to cool to room temperature, then a mixture of triethylamine (60.0 mL), acetic acid (20.0 mL) and EtOH (20.0 mL) added and the reaction heated at reflux for a further 2 h. After cooling, water (50 mL) was added and the mixture was partitioned between EtOAc (400 mL) and water (100 mL). The EtOAc layer was washed with further water (100 mL) and brine (100 mL), then dried (MgSO$_4$). The solvent was removed under reduced pressure and the resulting residue purified by chromatography on silica gel (5% MeOH/CH$_2$Cl$_2$ as eluant), giving ethyl 4-(2-fluoro-4-iodoanilino)-1-methyl-6-oxo-1,6-dihydro-3-pyridinecarboxylate as a white solid (10.48 g, 70%). $^1$H NMR [(CD$_3$)$_2$SO, 400 MHz] δ 9.31 (s, 1H), 8.54 (s, 1H), 7.77 (dd, J=10.1, 1.9 Hz, 1H), 7.60 (br dd, J=8.3, 1.0 Hz, 1H), 7.30 (t, J=8.5 Hz, 1H), 5.46 (s, 1H), 4.30 (q, J=7.1 Hz, 2H), 3.43 (s, 3H), 1.32 (t, J=7.1 Hz, 3H). Anal. Calcd for C$_{15}$H$_{14}$FIN$_2$O$_3$: C, 43.29; H, 3.39; N, 6.73. Found: C, 43.69; H, 3.26; N, 6.69.

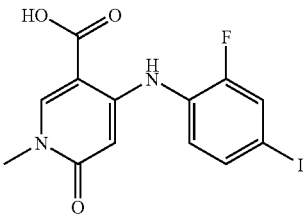

Step C: Preparation of 4-(2-fluoro-4-iodoanilino)-1-methyl-6-oxo-1,6-dihydro-3-pyridinecarboxylic acid Ethyl 4-(2-fluoro-4-iodoanilino)-1-methyl-6-oxo-1,6-dihydro-3-pyridinecarboxylate (140 mg, 0.34 mmol) was suspended in EtOH (10 mL), to which was added 1 M NaOH (10 mL). This mixture was stirred at R.T. for 15 h., then diluted with 1 M HCl (50 mL) and the resulting precipitate extracted into EtOAc (2×50 mL). The combined EtOAc fractions were dried (Na$_2$SO$_4$) and the solvent removed under reduced pressure to afford 4-(2-fluoro-4-iodoanilino)-1-methyl-6-oxo-1,6-dihydro-3-pyridinecarboxylic acid as a white solid (132 mg, 100%), m.p. (acetone/MeOH) 254-257° C. $^1$H NMR [(CD$_3$)$_2$SO, 400 MHz] δ 13.30 (v br s, 1H), 9.66 (s, 1H), 8.52 (s, 1H), 7.76 (dd, J=10.1, 1.9 Hz, 1H), 7.59 (ddd, J=8.4, 1.7, 0.8 Hz, 1H), 7.31 (t, J=8.5 Hz, 1H), 5.49 (d, J=0.7 Hz, 1H), 3.41 (s, 3H). Anal. Calcd for C$_{13}$H$_{10}$FIN$_2$O$_3$: C, 40.2; H, 2.6; N, 7.2. Found: C, 40.5; H, 2.3; N, 7.3.

Alternate Step C:

4-(2-Fluoro-4-iodo-phenylamino)-1-methyl-6-oxo-1,6-dihydro-pyridine-3-carboxylic acid 4-(2-Fluoro-4-iodo-phenylamino)-1-methyl-6-oxo-1,6-dihydro-pyridine-3-carboxylic acid ethyl ester was dissolved in EtOH (100 mL) and treated with NaOH (2.60 g, 72.0 mmol). This mixture was stirred at 70° C. for 20 hours. The mixture was cooled to room temperature and solvent was removed under reduced pressure. The residue was acidified with 1N HCl then the resulting precipitate was filtered and washed with water. The solid was dried under high vacuum pump to afford 4-(2-Fluoro-4-iodo-phenylamino)-1-methyl-6-oxo-1,6-dihydro-pyridine-3-carboxylic acid as a white solid (9.0 g, 96%). $^1$H NMR [(CD$_3$)$_2$SO, 400 MHz] δ 13.27(v br s, 1H), 9.60 (s, 1H), 8.49 (s, 1H), 7.74 (dd, J=10.1, 1.9 Hz, 1H), 7.59 (dd, J=8.4, 1.7, 0.8 Hz, 1H), 7.29 (dd, J=8.5 Hz, 1H), 5.48 (dd, J=0.7 Hz, 1H), 3.38 (s, 3H). (APCI$^+$) calcd for C$_{13}$H$_{10}$FIN$_2$O$_3$ 388.13 (M−1), found 386.9.

Step D: Preparation of 4-(2-fluoro-4-iodoanilino)-N-(2-hydroxyethoxy)-1-methyl-6-oxo-1,6-dihydro-3-pyridinecarboxamide To a mixture of 4-(2-fluoro-4-iodoanilino)-1-methyl-6-oxo-1,6-dihydro-3-pyridinecarboxylic acid (130 mg, 0.34 mmol) and 2-(aminooxy)ethanol [prepared by the literature procedure: Dhanak, D.; Reese, C. B., *J. Chem. Soc.*, Perkin Trans. 1, 1987; 2829] (52 mg, 0.67 mmol) in MeOH/THF (1:1, 20 mL) was added DMT-MM (187 mg, 0.67 mmol) and the mixture stirred at R.T. for 15 h. The reaction solvent was removed under reduced pressure and the oily residue partitioned between water (100 mL) and EtOAc (100 mL). The EtOAc fraction was then washed with water (2×100 mL) and brine (100 mL), dried ($Na_2SO_4$) and the solvent removed under reduced pressure. This afforded a cream solid which was purified by recrystallisation from EtOAc/MeOH to give 4-(2-fluoro-4-iodoanilino)-N-(2-hydroxyethoxy)-1-methyl-6-oxo-1,6-dihydro-3-pyridinecarboxamide as a white, crystalline solid (83 mg, 55%), m.p. (EtOAc/MeOH) 148-151° C. $^1$H NMR [($CD_3)_2SO$, 400 MHz] δ 11.65 (v br s, 1H), 9.48 (br s, 1H), 8.13 (s, 1H), 7.74 (dd, J=10.2, 1.8 Hz, 1H), 7.58 (br d, J=8.6 Hz, 1H), 7.28 (t, J=8.5 Hz, 1H), 5.55 (s, 1H), 4.76 (v br s, 1H), 3.90 (t, J=4.9 Hz, 2H), 3.61 (t, J=4.9 Hz, 2H), 3.36 (s, 3H). Anal. Calcd for $C_{15}H_{15}FIN_3O_4$: C, 40.3; H, 3.4; N, 9.4. Found: C, 40.6; H, 3.6; N, 9.1.

EXAMPLE 2

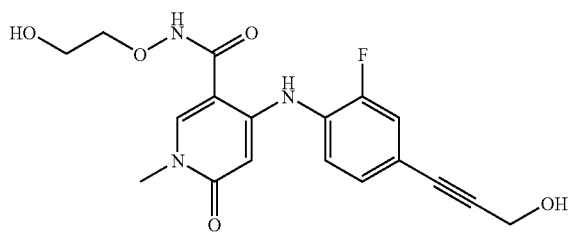

4-[2-Fluoro-4-(3-hydroxy-1-propynyl)anilino]-N-(2-hydroxyethoxy)-1-methyl-6-oxo-1,6-dihydro-3-pyridinecarboxamide 4-(2-Fluoro-4-iodoanilino)-N-(2-hydroxyethoxy)-1-methyl-6-oxo-1,6-dihydro-3-pyridinecarboxamide (330 mg, 0.74 mmol), CuI (3 mg, 0.01 mmol) and $(Ph_3P)_2PdCl_2$ (104 mg, 0.01 mmol) were dissolved dry THF (2 mL) in a flask which was then flushed with nitrogen. A solution of propargyl alcohol (47 mg, 0.81 mmol) in TEA (2 mL) was added to the reaction, which was stirred at R.T. for 15 h. The solvent was removed under reduced pressure, then the residue purified by chromatography on silica gel (10% MeOH/$CH_2Cl_2$ as eluant), giving 4-[2-fluoro-4-(3-hydroxy-1-propynyl)anilino]-N-(2-hydroxyethoxy)-1-methyl-6-oxo-1,6-dihydro-3-pyridinecarboxamide as a viscous, transparent oil (44%). $^1$H NMR [($CD_3)_2SO$, 400 MHz] δ 11.50 (v br s, 1H), 9.60 (s, 1H), 8.16 (s, 1H), 7.49 (t, J=8.3 Hz, 1H), 7.40 (dd, J=10.1, 1.9 Hz, 1H), 7.28 (dd, J=8.3, 1.4 Hz, 1H), 5.67 (s, 1H), 5.37 (t, J=5.1 Hz, 1H), 4.73 (br s, 1H), 4.30 (d, J=4.8 Hz, 2H), 3.91 (t, J=4.8 Hz, 2H), 3.62 (br t, J=4.8 Hz, 2H), 3.36 (s, 3H). LCMS (APCI$^+$) calcd for $C_{18}H_{19}N_3O_5F$ 376 (MH$^+$), found 376.

EXAMPLE 3

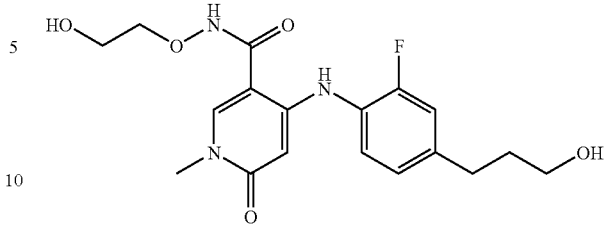

4-[2-Fluoro-4-(3-hydroxypropyl)anilino]-N-(2-hydroxyethoxy)-1-methyl-6-oxo-1,6-dihydro-3-pyridinecarboxamide 4-[2-Fluoro-4-(3-hydroxy-1-propynyl)anilino]-N-(2-hydroxyethoxy)-1-methyl-6-oxo-1,6-dihydro-3-pyridinecarboxamide (122 mg, 0.33 mmol) was dissolved in MeOH (20 mL), 5% Pd/C (20 mg) added, then the mixture stirred under an atmosphere of hydrogen (60 psi) for 15 h. at R.T. The Pd/C was removed by filtration through Celite® and all solvent removed under reduced pressure to yield crude yellow oil that was purified by chromatography on silica gel (10% MeOH/$CH_2Cl_2$ as eluant). 4-[2-Fluoro-4-(3-hydroxypropyl)anilino]-N-(2-hydroxyethoxy)-1-methyl-6-oxo-1, 6-dihydro-3-pyridinecarboxamide was isolated as a pale yellow foam (63%). $^1$H NMR [($CD_3)_2SO$, 400 MHz] δ 11.60 (v br s, 1H), 9.29 (br s, 1H), 8.13 (s, 1H), 7.33 (t, J=8.3 Hz, 1H), 7.18 (d, J=11.7 Hz, 1H), 7.07 (d, J=7.9 Hz, 1H), 5.40 (s, 1H), 4.77 (br s, 1H), 4.49 (t, J=5.1 Hz, 1H), 3.91 (t, J=3.9 Hz, 2H), 3.62 (t, J=4.8 Hz, 2H), 3.41 (q, J=5.9 Hz, 2H), 3.36 (s, 3H), 2.62 (t, J=7.6 Hz, 2H), 1.74 (pentet, J=7.0 Hz, 2H). HRMS (EI$^+$) calcd for $C_{18}H_{23}N_3O_5F$ 380.1622 (M$^+$), found 380.1623.

EXAMPLE 4

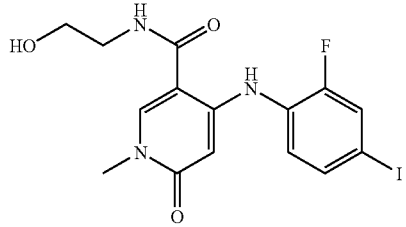

4-(2-Fluoro-4-iodoanilino)-N-(2-hydroxyethyl)-1-methyl-6-oxo-1,6-dihydro-3-pyridinecarboxamide

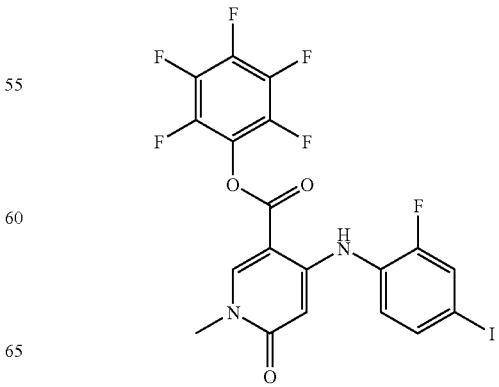

Step A: Preparation of 2,3,4,5,6-Pentafluorophenyl 4-(2-fluoro-4-iodoanilino)-1-methyl-6-oxo-1,6-dihydro-3-pyridinecarboxylate 4-(2-Fluoro-4-iodoanilino)-1-methyl-6-oxo-1,6-dihydro-3-pyridinecarboxylic acid (894 mg, 2.30 mmol) and pyridine (909 mg, 11.5 mmol) were dissolved in DMA (15 mL). To this mixture was added pentafluorophenyl trifluoroacetate (3.22 g, 11.5 mmol) then the solution was allowed to stir at R.T. for 2 h. The DMA solution was diluted with EtOAc (150 mL), which was washed sequentially with 1 M HCl (2×100 mL), water (100 mL), sat. NaHCO$_3$ (2×100 mL), and brine (100 mL). The EtOAc fraction was then dried (Na$_2$SO$_4$) and the solvent removed under reduced pressure to yield a viscous oil which was purified by column chromatography on silica gel (50% EtOAc/PE as eluant). This afforded 2,3,4,5,6-pentafluorophenyl-4-(2-fluoro-4-iodoanilino)-1-methyl-6-oxo-1,6-dihydro-3-pyridinecarboxylate as a cream foam (1.22 g, 96%) which was used directly in subsequent steps. $^1$H NMR [(CD$_3$)$_2$SO, 400 MHz] δ 9.03 (s, 1H), 8.70 (s, 1H), 7.79 (dd, J=10.1, 1.9 Hz, 1H), 7.62 (br dd, J=8.4, 1.0 Hz, 1H), 7.29 (t, J=8.4 Hz, 1H), 5.36 (d, J=1.6 Hz, 1H), 3.45 (s, 3H). LCMS (APCI$^+$) calcd for C$_{19}$H$_9$F$_6$N$_2$O$_3$ 555 (MH$^+$), found 555.

Step B: Preparation of 4-(2-fluoro-4-iodoanilino)-N-(2-hydroxyethyl)-1-methyl-6-oxo-1,6-dihydro-3-pyridinecarboxamide 2,3,4,5,6-Pentafluorophenyl-4-(2-fluoro-4-iodoanilino)-1-methyl-6-oxo-1,6-dihydro-3-pyridinecarboxylate (600 mg, 1.08 mmol) was dissolved in THF (15 mL) to which was added DIEA (697 mg, 5.40 mmol), followed by 2-aminoethanol (132 mg, 2.17 mmol). This mixture was stirred at R.T. for 2 h., then the reaction solvent removed under reduced pressure and the resulting white solid suspended in Et$_2$O. The solid was collected by filtration, then recrystallised from EtOAc/MeOH to give 4-(2-fluoro-4-iodoanilino)-N-(2-hydroxyethyl)-1-methyl-6-oxo-1,6-dihydro-3-pyridinecarboxamide (394 mg, 85%) as a white solid, m.p. (EtOAc/MeOH) 205-208° C. $^1$H NMR [(CD$_3$)$_2$SO, 400 MHz] δ 10.10 (s, 1H), 8.43 (br s, 1H), 8.28 (s, 1H), 7.72 (dd, J=10.2, 1.8 Hz, 1H), 7.56 (br d, J=8.5 Hz, 1H), 7.28 (t, J=8.5 Hz, 1H), 5.58 (s, 1H), 4.76 (br t, J=5.2 Hz, 1H), 3.50 (q, J=5.8 Hz, 2H), 3.36 (s, 3H), 3.32-3.26 (m, 2H). Anal. Calcd for C$_{15}$H$_{15}$FIN$_3$O$_3$: C, 41.8; H, 3.5; N, 9.8. Found: C, 4.19; H, 3.2; N, 9.7.

EXAMPLE 5

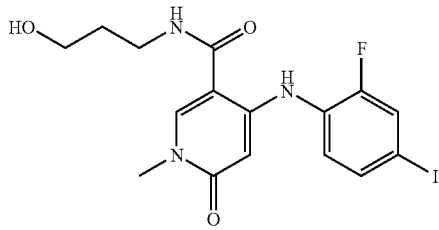

4-(2-Fluoro-4-iodoanilino)-N-(3-hydroxypropyl)-1-methyl-6-oxo-1,6-dihydro-3-pyridinecarboxamide 2,3,4,5,6-Pentafluorophenyl-4-(2-fluoro-4-iodoanilino)-1-methyl-6-oxo-1,6-dihydro-3-pyridinecarboxylate was reacted with 3-aminopropanol in THF in the presence of DIEA as for example 4, step B. The reaction solvent was removed under reduced pressure and the resulting oil purified by chromatography on silica gel (50% acetone/CH$_2$Cl$_2$) to give 4-(2-fluoro-4-iodoanilino)-N-(3-hydroxypropyl)-1-methyl-6-oxo-1,6-dihydro-3-pyridinecarboxamide as a white solid (95%), m.p. (Et$_2$O) 81-86° C. $^1$H NMR [(CD$_3$)$_2$SO, 400 MHz] δ 10.11 (s, 1H), 8.40 (br s, 1H), 8.24 (s, 1H), 7.74 (d, J=9.7 Hz, 1H), 7.58 (d, J=8.2 Hz, 1H), 7.29 (t, J=8.5 Hz, 1H), 5.59 (s, 1H), 4.48 (t, J=5.1 Hz, 1H), 3.48 (q, J=5.7 Hz, 2H), 3.37 (s, 3H), 3.30-3.24 (m, 2H), 1.67 (pentet, J=6.7 Hz, 2H). Anal. Calcd for C$_{16}$H$_{17}$FIN$_3$O$_3$.0.5H$_2$O: C, 42.3; H, 4.0; N, 9.3. Found: C, 42.2; H, 3.8; N, 9.1.

EXAMPLE 6

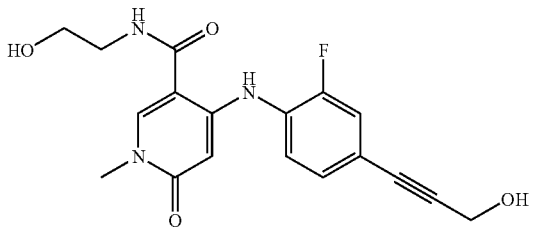

4-[2-Fluoro-4-(3-hydroxy-1-propynyl)anilino]-N-(2-hydroxyethyl)-1-methyl-6-oxo-1,6-dihydro-3-pyridinecarboxamide 4-(2-Fluoro-4-iodoanilino)-N-(2-hydroxyethyl)-1-methyl-6-oxo-1,6-dihydro-3-pyridinecarboxamide was reacted with propargyl alcohol in the presence of CuI, (Ph$_3$P)$_2$PdCl$_2$ and TEA in THF/DMF (1:1) as for example 2. The residue resulting from removal of the reaction solvents under reduced pressure was purified by column chromatography on silica gel (10% MeOH/CH$_2$Cl$_2$ as eluant) to give 4-[2-fluoro-4-(3-hydroxy-1-propynyl)anilino]-N-(2-hydroxyethyl)-1-methyl-6-oxo-1,6-dihydro-3-pyridinecarboxamide as a cream solid (79%). $^1$H NMR [(CD$_3$)$_2$SO, 400 MHz] δ 10.26 (s, 1H), 8.44 (t, J=5.4 Hz, 1H), 8.30 (s, 1H), 7.48 (t, J=8.4 Hz, 1H), 7.38 (dd, J=11.6, 1.8 Hz, 1H), 7.27 (dd, J=8.3, 1.4 Hz, 1H), 5.70 (s, 1H), 5.35 (t, J=5.9 Hz, 1H), 4.76 (t, J=5.7 Hz, 1H), 4.30 (d, J=6.0 Hz, 2H), 3.50 (q, J=5.8 Hz, 2H), 3.38 (s, 3H), 3.31-3.26 (m, 2H). LCMS (APCI$^+$) calcd for C$_{18}$H$_{18}$FN$_3$O$_4$ 360 (MH$^+$), found 360.

EXAMPLE 7

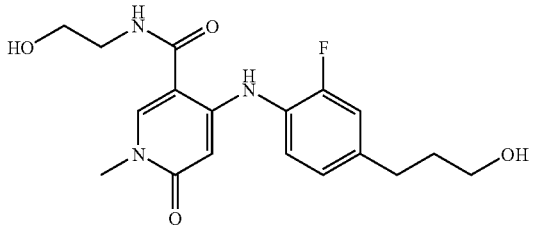

4-[2-Fluoro-4-(3-hydroxypropyl)anilino]-N-(2-hydroxyethyl)-1-methyl-6-oxo-1,6-dihydro-3-pyridinecarboxamide 4-[2-Fluoro-4-(3-hydroxy-1-propynyl)anilino]-N-(2-hydroxyethyl)-1-methyl-6-oxo-1,6-dihydro-3-pyridinecarboxamide was hydrogenated in MeOH in the presence of 5% Pd/C as for example 3. Purification of the crude oil was carried out by column chromatography on silica gel (5%

MeOH/CH$_2$Cl$_2$ as eluant) to give 4-[2-fluoro-4-(3-hydroxypropyl)anilino]-N-(2-hydroxyethyl)-1-methyl-6-oxo-1,6-dihydro-3-pyridinecarboxamide as a white solid (92%), m.p. (CH$_2$Cl$_2$/MeOH) 177-179° C. $^1$H NMR [(CD$_3$)$_2$SO, 400 MHz] δ 9.88 (s, 1H), 8.40 (br t, J=5.2 Hz, 1H), 8.26 (s, 1H), 7.33 (t, J=8.4 Hz, 1H), 7.17 (dd, J=11.8, 1.4 Hz, 1H), 7.06 (dd, J=8.2, 1.2 Hz, 1H), 5.42 (d, J=0.8 Hz, 1H), 4.78 (t, J=5.5 Hz, 1H), 4.49 (t, J=5.1 Hz, 1H), 3.50 (q, J=5.8 Hz, 2H), 3.41 (q, J=6.0 Hz, 2H), 3.35 (s, 3H), 3.31-3.25 (m, 2H), 2.63 (t, J=7.6 Hz, 2H), 1.72 (pentet, J=6.5 Hz, 2H). Anal. Calcd for C$_{18}$H$_{22}$FN$_3$O$_4$: C, 59.5; H, 6.1; N, 11.6. Found: C, 59.3; H, 6.3; N, 11.5.

EXAMPLE 8

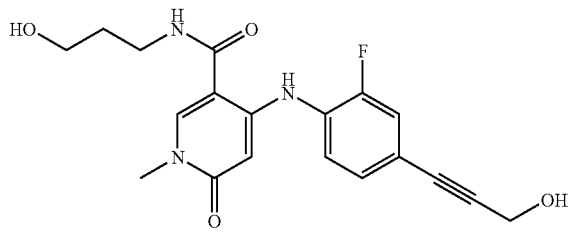

4-[2-Fluoro-4-(3-hydroxy-1-propynyl)anilino]-N-(3-hydroxypropyl)-1-methyl-6-oxo-1,6-dihydro-3-pyridinecarboxamide 4-(2-Fluoro-4-iodoanilino)-N-(3-hydroxypropyl)-1-methyl-6-oxo-1,6-dihydro-3-pyridinecarboxamide was reacted with propargyl alcohol in the presence of CuI, (Ph$_3$P)$_2$PdCl$_2$ and TEA in THF/DMF (1:1) as for example 2. The residue resulting from removal of the reaction solvents under reduced pressure was purified by column chromatography on silica gel (10% MeOH/CH$_2$Cl$_2$ as eluant) to give 4-[2-fluoro-4-(3-hydroxy-1-propynyl)anilino]-N-(3-hydroxypropyl)-1-methyl-6-oxo-1,6-dihydro-3-pyridinecarboxamide as a cream solid (89%). $^1$H NMR [(CD$_3$)$_2$SO, 400 MHz] δ 10.27 (s, 1H), 8.40 (t, J=5.4 Hz, 1H), 8.25 (s, 1H), 7.48 (t, J=8.5 Hz, 1H), 7.39 (dd, J=11.6, 1.8 Hz, 1H), 7.27 (dd, J=8.3, 1.4 Hz, 1H), 5.70 (s, 1H), 5.34 (t, J=6.1 Hz, 1H), 4.47 (t, J=5.1 Hz, 1H), 4.30 (d, J=6.0 Hz, 2H), 3.46 (q, J=5.9 Hz, 2H), 3.38 (s, 3H), 3.27 (q, J=6.5 Hz, 2H), 1.66 (pentet, J=6.7 Hz, 2H). LCMS (APCI$^+$) calcd for C$_{19}$H$_{21}$FN$_3$O$_4$ 374 (MH$^+$), found 374.

EXAMPLE 9

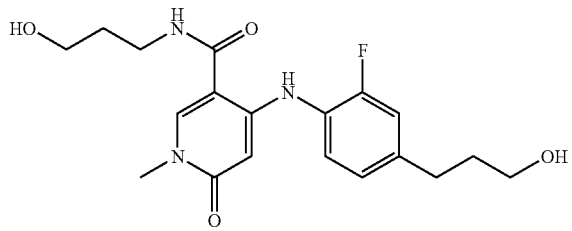

4-[2-Fluoro-4-(3-hydroxypropyl)anilino]-N-(3-hydroxypropyl)-1-methyl-6-oxo-1,6-dihydro-3-pyridinecarboxamide 4-[2-Fluoro-4-(3-hydroxy-1-propynyl)anilino]-N-(3-hydroxypropyl)-1-methyl-6-oxo-1,6-dihydro-3-pyridinecarboxamide was hydrogenated in MeOH in the presence of 5% Pd/C for example 3. Purification of the crude oil was carried out by column chromatography on silica gel (5% MeOH/CH$_2$Cl$_2$ as eluant) to give 4-[2-fluoro-4-(3-hydroxypropyl)anilino]-N-(3-hydroxypropyl)-1-methyl-6-oxo-1,6-dihydro-3-pyridinecarboxamide as a white solid (92%), m.p. (CH$_2$Cl$_2$/MeOH) 161-164° C. $^1$H NMR [(CD$_3$)$_2$SO, 400 MHz] δ 9.88 (s, 1H), 8.36 (t, J=5.4 Hz, 1H), 8.21 (s, 1H), 7.33 (t, J=8.3 Hz, 1H), 7.17 (dd, J=11.9, 1.7 Hz, 1H), 7.06 (dd, J=8.1, 1.4 Hz, 1H), 5.42 (d, J=0.9 Hz, 1H), 4.48 (t, J=5.0 Hz, 1H), 4.09 (q, J=5.2 Hz, 1H), 3.47 (q, J=5.9 Hz, 2H), 3.41 (q, J=6.0 Hz, 2H), 3.35 (s, 3H), 3.26 (q, J=6.6 Hz, 2H), 2.62 (t, J=7.7 Hz, 2H), 1.75-1.62 (m, 4H). Anal. Calcd for C$_{19}$H$_{24}$FN$_3$O$_4$.0.5H$_2$O; C, 59.1; H, 6.5; N, 10.9. Found: C, 59.3; H, 6.4; N, 10.9.

EXAMPLE 10

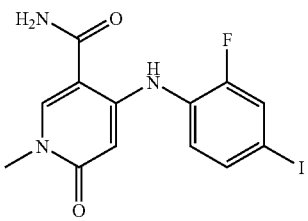

4-(2-Fluoro-4-iodoanilino)-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid recrystallised from EtOAc/MeOH to afford 4-(2-fluoro-4-iodoanilino)-1-methyl-6-oxo-1,6-dihydro-3-pyridinecarboxamide as white crystals (84%), m.p. (EtOAc/MeOH) 283-285° C. $^1$H NMR [(CD$_3$)$_2$SO, 400 MHz] δ 10.40 (s, 1H), 8.34 (s, 1H), 7.88 (br s, 1H), 7.74 (dd, J=9.9, 1.9 Hz, 1H), 7.57 (br d, J=7.8 Hz, 1H), 7.46 (br s, 1H), 7.30 (t, J=8.5 Hz, 1H), 5.56 (d, J=0.7 Hz, 1H), 3.36 (s, 3H). Anal. Calcd for C$_{13}$H$_{11}$FIN$_3$O$_2$: C, 40.3; H, 2.9; N, 10.9. Found: C, 40.6; H, 2.7; N, 10.9.

EXAMPLE 11

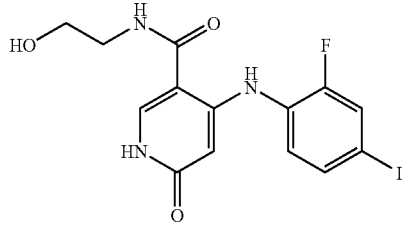

4-(2-Fluoro-4-iodoanilino)-N-(2-hydroxyethyl)-6-oxo-1,6-dihydro-3-pyridinecarboxamide

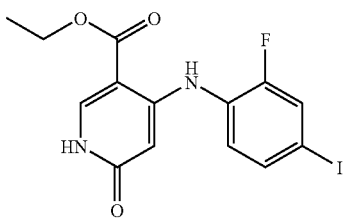

Step A: Preparation of ethyl 4-(2-fluoro-4-iodoanilino)-6-oxo-1,6-dihydro-3-pyridinecarboxylate Ethyl 6-chloro-4-(2-fluoro-4-iodoanilino)nicotinate (2.03 g, 4.83 mmol) was dissolved in acetic acid (75 mL), to which was added water (25 mL). This solution was heated at reflux for 14 h. The mixture was allowed to cool, then refrigerated, and a cream solid crystallised out. This material was isolated by filtration, washed well with water and hexanes, then dried to afford ethyl 4-(2-fluoro-4-iodoanilino)-6-oxo-1,6-dihydro-3-pyridinecarboxylate as a white solid (1.14 g, 59%), m.p. (acetone/MeOH) 262-264° C. $^1$H NMR [(CD$_3$)$_2$SO, 400 MHz] δ 11.59 (br s, 1H), 9.32 (s, 1H), 8.10 (s, 1H), 7.77 (dd, J=10.1, 1.9 Hz, 1H), 7.61 (ddd, J=8.4, 2.0, 0.8 Hz, 1H), 5.38 (d, J=1.3 Hz, 1H), 7.26-7.33 (m, 1H), 4.27 (q, J=7.1 Hz, 2H), 1.30 (t, J=7.1 Hz, 3H). Anal. Calcd for C$_{14}$H$_{12}$FIN$_2$O$_3$: C, 41.8; H, 3.0; N, 7.0. Found: C, 41.9; H, 2.8; N, 7.0.

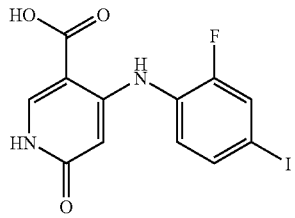

Step B: Preparation of 4-(2-fluoro-4-iodoanilino)-6-oxo-1,6-dihydro-3-pyridinecarboxylic acid Ethyl 4-(2-fluoro-4-iodoanilino)-6-oxo-1,6-dihydro-3-pyridinecarboxylate was dissolved in EtOH and treated with 1 M NaOH, as for example 1, step C, to hydrolyse the ester to give 4-(2-fluoro-4-iodoanilino)-6-oxo-1,6-dihydro-3-pyridinecarboxylic acid as a white solid (99%), used directly in the next step. $^1$H NMR [(CD$_3$)$_2$SO, 400 MHz] δ 13.30 (v br s, 1H), 11.44 (br s, 1H), 9.75 (br s, 1H), 8.06 (s, 1H), 7.76 (dd, J=10.2, 1.9 Hz, 1H), 7.59 (ddd, J=8.3, 1.9, 0.9 Hz, 1H), 7.32 (t, J=8.4 Hz, 1H), 5.40 (d, J=1.1 Hz, 1H). LCMS (APCI$^+$) calcd for C$_{12}$H$_9$FIN$_2$O$_3$ 375 (MH$^+$), found 375.

Step C: Preparation of 4-(2-fluoro-4-iodoanilino)-N-(2-hydroxyethyl)-6-oxo-1,6-dihydro-3-pyridinecarboxamide 4-(2-Fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with 2-aminoethanol in the presence of DIEA as for example 4, step B. All solvent was removed from the reaction mixture under reduced pressure, and the resulting solid recrystallised from acetone/MeOH to give 4-(2-fluoro-4-iodoanilino)-N-(2-hydroxyethyl)-6-oxo-1,6-dihydro-3-pyridinecarboxamide as a white solid (74%), m.p. (acetone/MeOH) 254-256° C. $^1$H NMR [(CD$_3$)$_2$SO, 400 MHz] δ 11.38 (br s, 1H), 10.24 (br s, 1H), 8.51 (br s, 1H), 7.96 (s, 1H), 7.73 (dd, J=10.1, 1.8 Hz, 1H), 7.57 (dd, J=8.4, 0.9 Hz, 1H), 7.28 (t, J=8.5 Hz, 1H), 5.48 (s, 1H), 4.75 (br s, 1H), 3.48 (br s, 2H), 3.26 (br q, J=5.7 Hz, 2H). Anal. Calcd for C$_{14}$H$_{13}$FIN$_3$O$_3$.0.5H$_2$O: C, 39.5; H, 3.3; N, 9.9. Found: C, 39.7; H, 3.2; N, 9.8.

EXAMPLE 12

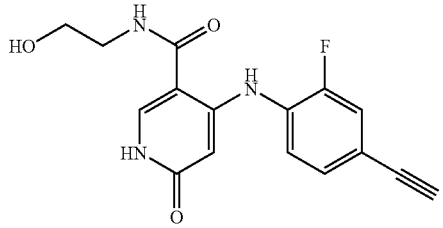

4-(4-Ethynyl-2-fluoroanilino)-N-(2-hydroxyethyl)-6-oxo-1,6-dihydro-3-pyridinecarboxamide

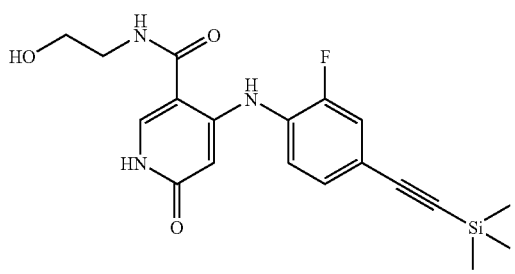

Step A: Preparation of 4-{2-fluoro-4-[(trimethylsilyl)ethynyl]anilino}-N-(2-hydroxyethyl)-6-oxo-1,6-dihydro-3-pyridinecarboxamide 4-(2-Fluoro-4-iodoanilino)-N-(2-hydroxyethyl)-6-oxo-1,6-dihydro-3-pyridinecarboxamide was reacted with TMS-acetylene in the presence of CuI, (Ph$_3$P)$_2$PdCl$_2$ and TEA in THF/DMF (1:1) as for example 2. The residue resulting from removal of the reaction solvents under reduced pressure was purified by column chromatography on silica gel (10% MeOH/CH$_2$Cl$_2$ as eluant) to give 4-{2-fluoro-4-[(trimethylsilyl)ethynyl]anilino}-N-(2-hydroxyethyl)-6-oxo-1,6-dihydro-3-pyridinecarboxamide as an off-white solid (72%), used directly in the next step. $^1$H NMR [(CD$_3$)$_2$SO, 400 MHz] δ 11.45 (br s, 1H), 10.45 (s, 1H), 8.50 (t, J=5.4 Hz, 1H), 7.96 (s, 1H), 7.48 (t, J=8.4 Hz, 1H), 7.42 (dd, J=11.5, 1.8 Hz, 1H), 7.30 (dd, J=8.3, 1.4 Hz, 1H), 5.65 (s, 1H), 4.71 (t, J=5.7 Hz, 1H), 3.49 (q, J=5.9 Hz, 2H), 3.29-3.24 (m, 2H), 0.24 (s, 9H). HRMS (FAB$^+$) calcd C$_{19}$H$_{23}$FN$_3$O$_3$Si (MH$^+$) 388.1493, found 388.1488.

Step B: Preparation of 4-(4-ethynyl-2-fluoroanilino)-N-(2-hydroxyethyl)-6-oxo-1,6-dihydro-3-pyridinecarboxamide 4-{2-Fluoro-4-[(trimethylsilyl)ethynyl]anilino}-N-(2-hydroxyethyl)-6-oxo-1,6-dihydro-3-pyridinecarboxamide (195 mg, 0.50 mmol) was dissolved/suspended in a mixture of MeOH (30 mL) and THF (20 mL) to which was added solid K$_2$CO$_3$ (139 mg, 1.01 mmol). This mixture was stirred for 48 h. at R.T. All solvent was then removed under reduced pressure, the residue taken up into EtOAc containing 10% MeOH (100 mL), and this solution washed with water (2×100 mL) and brine (100 mL). The combined aqueous fractions were back-extracted with EtOAc (2×100 mL). All EtOAc fractions were combined and dried with Na$_2$SO$_4$, the solvent removed under reduced pressure and the residue purified by column chromatography on silica gel (5% MeOH/CH$_2$Cl$_2$ as eluant). This gave 4-(4-ethynyl-2-fluoroanilino)-N-(2-hydroxyethyl)-6-oxo-1,6-dihydro-3-pyridinecarboxamide as a white solid (152 mg, 96%), m.p. (acetone/MeOH) 265-273° C. $^1$H NMR [(CD$_3$)$_2$SO, 400 MHz] δ 11.44 (br s, 1H), 10.41 (s, 1H), 8.49 (br t, J=5.1 Hz, 1H), 7.97 (s, 1H), 7.50 (t, J=8.5 Hz, 1H), 7.45 (dd, J=11.5, 1.8 Hz, 1H), 7.33 (dd, J=8.3, 1.4 Hz, 1H), 5.62 (s, 1H), 4.72 (t, J=5.7 Hz, 1H), 4.24 (s, 1H), 3.50 (q, J=5.8 Hz, 2H), 3.31-3.23 (m, 2H). Anal. Calcd for C$_{16}$H$_{14}$FN$_3$O$_3$: C, 61.0; H, 4.5; N, 13.3. Found: C, 61.1; H, 4.3; N, 13.3.

EXAMPLE 13

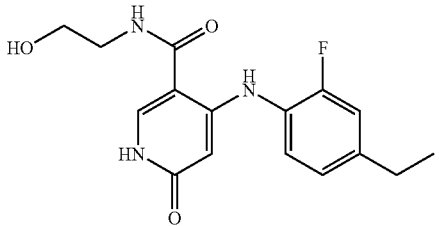

4-(4-Ethyl-2-fluoroanilino-N-(2-hydroxyethyl)-6-oxo-1,6-dihydro-3-pyridinecarboxamide 4-(4-Ethynyl-2-fluoroanilino)-N-(2-hydroxyethyl)-6-oxo-1,6-dihydro-3-pyridinecarboxamide was hydrogenated in MeOH/THF in the presence of 5% Pd/C as for example 3. Purification of the crude oil was carried out by column chromatography on silica gel (10% MeOH/CH$_2$Cl$_2$ as eluant) to give 4-(4-ethyl-2-fluoroanilino)-N-(2-hydroxyethyl)-6-oxo-1,6-dihydro-3-pyridinecarboxamide as a white solid (100%), m.p. (EtOAc/MeOH) 256-258° C. $^1$H NMR [(CD$_3$)$_2$SO, 400 MHz] δ 11.29 (br s, 1H), 10.00 (s, 1H), 8.43 (t, J=5.2 Hz, 1H), 7.93 (s, 1H), 7.33 (t, J=8.4 Hz, 1H), 7.19 (dd, J=11.9, 1.5 Hz, 1H), 7.08 (dd, J=8.2, 1.5 Hz, 1H), 5.32 (s, 1H), 4.71 (t, J=5.7 Hz, 1H), 3.49 (q, J=5.9 Hz, 2H), 3.29-3.24 (m, 2H), 2.62 (q, J=7.6 Hz, 2H), 1.21 (t, J=7.6 Hz, 3H). Anal. Calcd for C$_{16}$H$_{18}$FN$_3$O$_3$: C, 60.2; H, 5.7; N, 13.2. Found: C, 60.2; H, 5.7; N, 13.4.

EXAMPLE 14

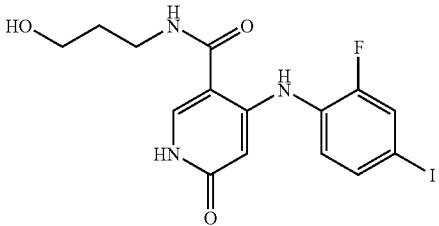

4-(2-Fluoro-4-iodoanilino)-N-(3-hydroxypropyl)-6-oxo-1,6-dihydro-3-pyridinecarboxamide 4-(2-Fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with 3-aminopropanol in the presence of DIEA as for example 4, step B. All solvent was removed from the reaction mixture under reduced pressure, and the resulting residue purified by column chromatography on silica gel (10% MeOH/CH$_2$Cl$_2$) to give 4-(2-fluoro-4-iodoanilino)-N-(3-hydroxypropyl)-6-oxo-1,6-dihydro-3-pyridinecarboxamide as a crystalline white solid (89%), m.p. (EtOAc) 253-255° C. $^1$H NMR [(CD$_3$)$_2$SO, 400 MHz] δ 11.39 (br s, 1H), 10.26 (br s, 1H), 8.47 (br s, 1H), 7.92 (s, 1H), 7.74 (dd, J=10.2, 1.7 Hz, 1H), 7.57 (dd, J=8.5, 0.8 Hz, 1H), 7.28 (t, J=8.5 Hz, 1H), 5.49 (s, 1H), 4.46 (br s, 1H), 3.48-3.41 (m, 2H), 3.24 (q, J=6.4 Hz, 2H), 1.64 (pentet, J=6.7 Hz, 2H). Anal. Calcd for C$_{15}$H$_{15}$FIN$_3$O$_3$: C, 41.8; H, 3.5; N, 9.8. Found: C, 41.6; H, 3.2; N, 9.5.

EXAMPLE 15

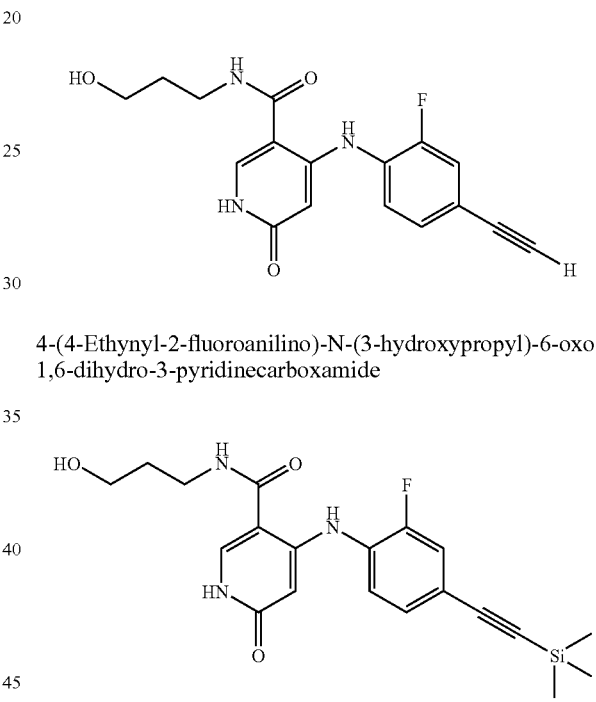

4-(4-Ethynyl-2-fluoroanilino)-N-(3-hydroxypropyl)-6-oxo-1,6-dihydro-3-pyridinecarboxamide Step A: Preparation of 4-{2-Fluoro-4-[(trimethylsilyl)ethynyl]anilino}-N-(3-hydroxypropyl)-6-oxo-1,6-dihydro-3-pyridinecarboxamide 4-(2-Fluoro-4-iodoanilino)-N-(3-hydroxypropyl)-6-oxo-1,6-dihydro-3-pyridinecarboxamide was reacted with TMS-acetylene in the presence of CuI, (Ph$_3$P)$_2$PdCl$_2$ and TEA in THF/DMF (1:1) as for example 2. The residue resulting from removal of the reaction solvents under reduced pressure was purified by column chromatography on silica gel (10% MeOH/CH$_2$Cl$_2$ as eluant) to give 4-{2-fluoro-4-[(trimethylsilyl)ethynyl]anilino}-N-(3-hydroxypropyl)-6-oxo-1,6-dihydro-3-pyridinecarboxamide as an off-white solid (94%), used directly in the next step. $^1$H NMR [(CD$_3$)$_2$SO, 400 MHz] δ 11.48 (br s, 1H), 10.50 (s, 1H), 8.49 (t, J=5.4 Hz, 1H), 7.93 (s, 1H), 7.49 (t, J=8.5 Hz, 1H), 7.43 (dd, J=11.5, 1.8 Hz, 1H), 7.30 (dd, J=8.3, 1.5 Hz, 1H), 5.66 (s, 1H), 4.46 (t, J=5.1 Hz, 1H), 3.45 (q, J=5.9 Hz, 2H), 3.25 (q, J=6.5 Hz, 2H), 1.65 (pentet, J=6.7 Hz, 2H), 0.23 (s, 9H). HRMS (FAB$^+$) calcd C$_{20}$H$_{25}$FN$_3$O$_3$Si (MH$^+$) 402.1649, found 402.1649.

Step B: Preparation of 4-(4-ethynyl-2-fluoroanilino)-N-(3-hydroxypropyl)-6-oxo-1,6-dihydro-3-pyridinecarboxamide 4-{2-Fluoro-4-[(trimethylsilyl)ethynyl]anilino}-N-(3-hydroxypropyl)-6-oxo-1,6-dihydro-3-pyridinecarboxamide was reacted with K₂CO₃ in MeOH/THF as for example 12, step B. The resulting crude product was purified by column chromatography on silica gel (10% MeOH/CH₂Cl₂ as eluant) to give 4-(4-ethynyl-2-fluoroanilino)-N-(3-hydroxypropyl)-6-oxo-1,6-dihydro-3-pyridinecarboxamide as a pale yellow solid (68%), m.p. (EtOAc/MeOH) 249-252° C. $^1$H NMR [(CD₃)₂SO, 400 MHz] δ 11.42 (br s, 1H), 10.44 (s, 1H), 8.46 (s, 1H), 7.93 (s, 1H), 7.49 (t, J=8.5 Hz, 1H), 7.45 (dd, J=11.4, 1.9 Hz, 1H), 7.33 (dd, J=8.3, 1.3 Hz, 1H), 5.63 (s, 1H), 4.43 (t, J=5.2 Hz, 1H), 4.23 (s, 1H), 3.46 (q, J=5.9 Hz, 2H), 3.31-3.22 (m, 2H), 1.66 (pentet, J=6.7 Hz, 2H). Anal. Calcd for C₁₇H₁₆FN₃O₃: C, 62.0; H, 4.9; N, 12.8. Found: C, 62.0; H, 5.2; N, 12.8.

EXAMPLE 16

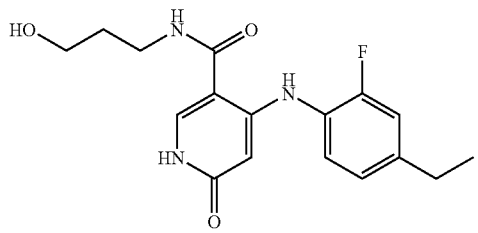

4-(4-Ethyl-2-fluoroanilino)-N-(3-hydroxypropyl)-6-oxo-1,6-dihydro-3-pyridinecarboxamide 4-(4-Ethynyl-2-fluoroanilino)-N-(3-hydroxypropyl)-6-oxo-1,6-dihydro-3-pyridinecarboxamide was hydrogenated in MeOH/THF in the presence of 5% Pd/C as for example 3. Purification of the crude oil was carried out by column chromatography on silica gel (10% MeOH/CH₂Cl₂ as eluant) to give 4-(4-ethyl-2-fluoroanilino)-N-(3-hydroxypropyl)-6-oxo-1,6-dihydro-3-pyridinecarboxamide as a white solid (91%), m.p. (EtOAc) 231-233° C. $^1$H NMR [(CD₃)₂SO, 400 MHz] δ 11.28 (br s, 1H), 10.02 (s, 1H), 8.41 (t, J=5.1 Hz, 1H), 7.90 (s, 1H), 7.32 (t, J=8.3 Hz, 1H), 7.19 (dd, J=11.9, 1.8 Hz, 1H), 7.08 (d, J=8.2 Hz, 1H), 5.33 (s, 1H), 4.44 (t, J=5.1 Hz, 1H), 3.46 (q, J=5.2 Hz, 2H), 3.30-3.22 (m, 2H), 2.62 (q, J=7.6 Hz, 2H), 1.66 (pentet, J=6.7 Hz, 2H), 1.21 (t, J=7.6 Hz, 3H). Anal. Calcd for C₁₇H₂₀FN₃O₃: C, 61.1; H, 6.1; N, 12.6. Found: C, 61.3; H, 5.9; N, 12.7.

EXAMPLE 17

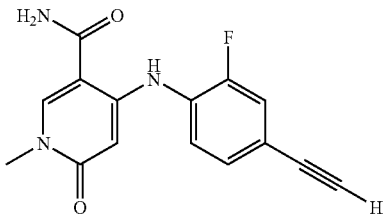

4-(4-Ethynyl-2-fluoroanilino)-1-methyl-6-oxo-1,6-dihydro-3-pyridinecarboxamide

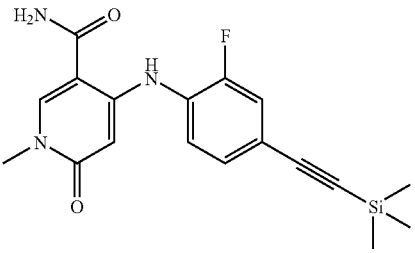

Step A: Preparation of 4-{2-fluoro-4-[(trimethylsilyl)ethynyl]anilino}-1-methyl-6-oxo-1,6-dihydro-3-pyridinecarboxamide 4-(2-Fluoro-4-iodoanilino)-1-methyl-6-oxo-1,6-dihydro-3-pyridinecarboxamide was reacted with TMS-acetylene in the presence of CuI, (Ph₃P)₂PdCl₂ and TEA in THF/DMF (1:1) as for example 2. The residue resulting from removal of the reaction solvents under reduced pressure was purified by column chromatography on silica gel (10% MeOH/CH₂Cl₂ as eluant) to give 4-{2-fluoro-4-[(trimethylsilyl)ethynyl]anilino}-1-methyl-6-oxo-1,6-dihydro-3-pyridinecarboxamide as a pale yellow solid (100%), used directly in the next step. $^1$H NMR [(CD₃)₂SO, 400 MHz] δ 10.66 (s, 1H), 8.38 (s, 1H), 7.92 (br s, 1H), 7.50 (t, J=8.5 Hz, 1H), 7.48 (br s, 1H), 7.42 (dd, J=11.5, 1.8 Hz, 1H), 7.30 (dd, J=8.3, 1.4 Hz, 1H), 5.73 (s, 1H), 3.38 (s, 3H), 0.23 (s, 9H). HRMS (EI⁺) calcd C₁₈H₂₀FN₃O₂Si (M⁺) 357.1309, found 357.1308.

Step B: Preparation of 4-(4-ethynyl-2-fluoroanilino)-1-methyl-6-oxo-1,6-dihydro-3-pyridinecarboxamide 4-{2-Fluoro-4-[(trimethylsilyl)ethynyl]anilino}-1-methyl-6-oxo-1,6-dihydro-3-pyridinecarboxamide was reacted with K₂CO₃ in MeOH/THF as for example 12, step B. The resulting crude product was purified by column chromatography on silica gel (50% acetone/CH₂Cl₂ as eluant) to give 4-(4-ethynyl-2-fluoroanilino)-1-methyl-6-oxo-1,6-dihydro-3-pyridinecarboxamide as a pale yellow-orange solid (73%), m.p. (CH₂Cl₂/MeOH) 269-272° C. $^1$H NMR [(CD₃)₂SO, 400 MHz] δ 10.60 (s, 1H), 8.37 (s, 1H), 7.91 (br s, 1H), 7.51 (t, J=8.4 Hz, 1H), 7.48 (br s, 1H), 7.46 (dd, J=11.4, 1.7 Hz, 1H), 7.33 (dd, J=8.3, 0.9 Hz, 1H), 5.71 (s, 1H), 4.25 (s, 1H), 3.37 (s, 3H). Anal. Calcd for C₁₅H₁₂FN₃O₂.0.25H₂O: C, 62.2; H, 4.4; N, 14.5. Found: C, 62.6; H, 4.1; N, 14.6.

EXAMPLE 18

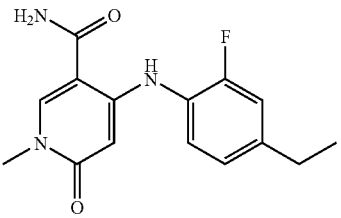

4-(4-Ethyl-2-fluoroanilino)-1-methyl-6-oxo-1,6-dihydro-3-pyridinecarboxamide 4-(4-Ethynyl-2-fluoroanilino)-1-methyl-6-oxo-1,6-dihydro-3-pyridinecarboxamide was hydrogenated in MeOH/THF in the presence of 5% Pd/C as for example 3. Purification of the crude oil was carried out by column chromatography on silica gel (50% acetone/CH₂Cl₂ as eluant) to give 4-(4-ethyl-2-fluoroanilino)-1-methyl-6-oxo-1,6-dihydro-3-pyridinecarboxamide as a cream solid (82%), m.p. (EtOAc) 268-272° C. ¹H NMR [(CD₃)₂SO, 400 MHz] δ 10.14 (s, 1H), 8.32 (s, 1H), 7.84 (br s, 1H), 7.43 (br s, 1H), 7.33 (t, J=8.4 Hz, 1H), 7.19 (dd, J=11.1, 1.7 Hz, 1H), 7.08 (dd, J=8.2, 1.5 Hz, 1H), 5.39 (d, J=1.1 Hz, 1H), 3.36 (s, 3H), 2.62 (q, J=7.6 Hz, 2H), 1.19 (t, J=7.6 Hz, 3H). Anal. Calcd for C₁₅H₁₆FN₃O₂: C, 62.3; H, 5.6; N, 14.5. Found: C, 62.5; H, 5.4; N, 14.8.

EXAMPLE 19

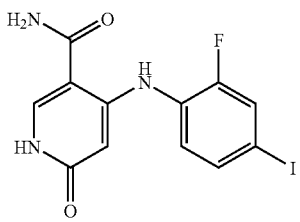

4-(2-Fluoro-4-iodoanilino)-6-oxo-1,6-dihydro-3-pyridinecarboxamide 4-(2-Fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH₃ solution in THF for example 4, step B. All solvent was removed under reduced pressure and the resulting solid recrystallised from EtOAc/MeOH to afford 4-(2-fluoro-4-iodoanilino)-6-oxo-1,6-dihydro-3-pyridinecarboxamide as cream needles (87%), m.p. (CH₂Cl₂/MeOH) 320-325° C. ¹H NMR [(CD₃)₂SO, 400 MHz] δ 11.42 (s, 1H), 10.53 (s, 1H), 8.01 (s, 1H), 7.96 (br s, 1H), 7.73 (dd, J=10.1 Hz, 1H), 7.57 (br d, J=8.4 Hz, 1H), 7.41 (br s, 1H), 7.29 (t, J=8.5 Hz, 1H), 5.47 (s, 1H). Anal. Calcd for C₁₂H₉FIN₃O₂: C, 38.6; H, 2.4; N, 11.3. Found: C, 38.9; H, 2.3; N, 11.3.

EXAMPLE 20

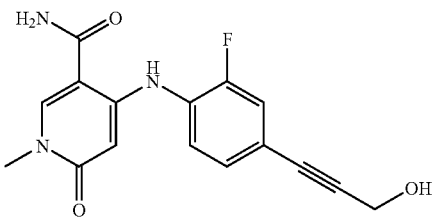

4-[2-Fluoro-4-(3-hydroxy-1-propynyl)anilino}-1-methyl-6-oxo-1,6-dihydro-3-pyridinecarboxamide 4-(2-Fluoro-4-iodoanilino)-1-methyl-6-oxo-1,6-dihydro-3-pyridinecarboxamide was reacted with propargyl alcohol in the presence of CuI, (Ph₃P)₂PdCl₂ and TEA in DMF as for example 2. The residue resulting from removal of the reaction solvents under reduced pressure was purified by column chromatography on silica gel (5% MeOH/CH₂Cl₂ as eluant) to give 4-[2-fluoro-4-(3-hydroxy-1-propynyl)anilino]-1-methyl-6-oxo-1,6-dihydro-3-pyridinecarboxamide as an off-white solid (89%). ¹H NMR [(CD₃)₂SO, 400 MHz] δ 10.57 (s, 1 H), 8.35 (s, 1H), 7.90 (br s, 1H), 7.50 (t, J=8.5 Hz, 1H), 7.48 (br s, 1H), 7.39 (dd, J=11.4, 1.8 Hz, 1H), 7.28 (dd, J=8.3, 1.5 Hz, 1H), 5.69 (s, 1H), 5.36 (t, J=6.0 Hz, 1H), 4.30 (d, J=5.9 Hz, 2H), 3.37 (s, 3H). LCMS (APCI⁺) calcd for C₁₆H₁₅FN₃O₃ 316 (MH⁺), found 316.

EXAMPLE 21

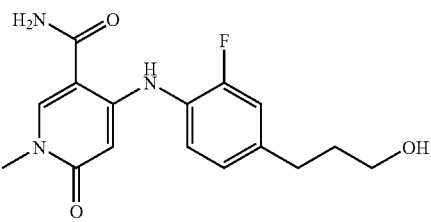

4-[2-Fluoro-4-(3-hydroxypropyl)anilino}-1-methyl-6-oxo-1,6-dihydro-3-pyridinecarboxamide 4-[2-Fluoro-4-(3-hydroxy-1-propynyl)anilino]-1-methyl-6-oxo-1,6-dihydro-3-pyridinecarboxamide was hydrogenated in MeOH/THF in the presence of 5% Pd/C as for example 3. Purification of the crude oil was carried out by column chromatography on silica gel (5% MeOH/CH₂Cl₂ as eluant) to give 4-[2-fluoro-4-(3-hydroxypropyl)anilino]-1-methyl-6-oxo-1,6-dihydro-3-pyridinecarboxamide as a crystalline cream solid (90%), m.p. (EtOAc/MeOH) 214-216° C. ¹H NMR [(CD₃)₂SO, 400 MHz] δ 10.15 (s, 1H), 8.32 (s, 1H), 7.85 (br s, 1H), 7.43 (br s, 1H), 7.33 (t, J=8.3 Hz, 1H), 7.17 (dd, J=11.8, 1.7 Hz, 1H), 7.07 (dd, J=8.2, 1.6 Hz, 1H), 5.40 (s, 1H), 4.50 (t, J=5.1 Hz, 1H), 3.41 (q, J=6.0 Hz, 2H), 3.36 (s, 3H), 2.63 (t, J=7.7 Hz, 2H), 1.76-1.69 (m, 2H). Anal. Calcd for C₁₆H₁₈FN₃O₃: C, 60.2; H, 5.7; N, 13.2. Found: C, 60.5; H, 5.8; N, 13.3.

EXAMPLE 22

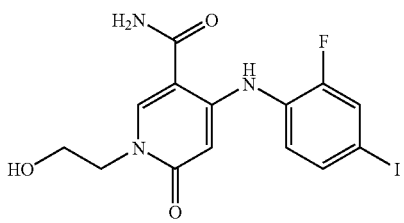

4-(2-Fluoro-4-iodoanilino)-1-(2-hydroxyethyl)-6-oxo-1,6-dihydro-3-pyridinecarboxamide Step A: Preparation of ethyl 4-(2-fluoro-4-iodoanilino)-6-oxo-1-[2-(tetrahydro-2H-pyran-2-yloxy)ethyl]-1,6-dihydro-3-pyridinecarboxylate

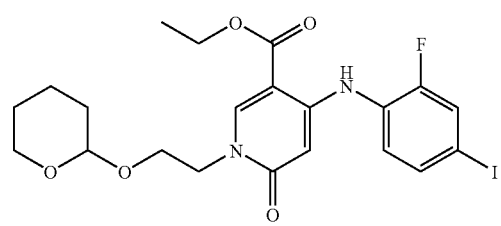

2-Iodoethanol was protected as the tetrahydropyranyl ether according to a literature method [*J. Org. Chem.*, 54(10), 2407 (1989)]. Ethyl 4-(2-fluoro-4-iodoanilino)-6-oxo-1,6-dihydro-3-pyridinecarboxylate (383 mg, 0.95 mmol) was dissolved/suspended in dry DMF (15 mL) and the solution cooled (ice/water). NaH (42 mg, 1.05 mmol) was added, the flask placed under nitrogen, and the resulting mixture allowed to warm and stirred at R.T. for 2 h. A solution of the protected iodide (1.22 g, 4.77 mmol) in dry DMF (5 mL) was added as a single portion and the entire mixture stirred at R.T. for 15 h. Water (100 mL) was added and the resulting aqueous suspension extracted with EtOAc (3×50 mL). The combined EtOAc fractions were then washed with water (2×50 mL) and brine (50 mL), then dried (Na$_2$SO$_4$). The solvent was removed under reduced pressure to afford an oil which was purified by chromatography on silica gel (50% EtOAc/hexanes as eluant). Ethyl 4-(2-fluoro-4-iodoanilino)-6-oxo-1-[2-(tetrahydro-2H-pyran-2-yloxy)ethyl]-1,6-dihydro-3-pyridinecarboxylate was isolated as a transparent oil which gave a waxy solid over time (249 mg, 49%), this material was used directly in the next step. $^1$H NMR [(CD$_3$)$_2$SO, 400 MHz] δ 9.31 (s, 1H), 8.49 (s, 1H), 7.78 (dd, J=10.2, 1.9 Hz, 1H), 7.61 (br d, J=8.6 Hz, 1H), 7.31 (t, J=7.5 Hz, 1H), 5.45 (s, 1H), 4.59 (br s, 1H), 4.30 (q, J=7.0 Hz, 2H), 4.11 (t, J=5.0 Hz, 2H), 3.75 (pentet, J=5.5 Hz, 1H), 3.61-3.49 (m, 2H), 3.40-3.32 (m, 1H), 1.74-1.33 (m, 6H), 1.30 (t, J=7.1 Hz, 3H). HRMS (EI$^+$) calcd C$_{21}$H$_{24}$FIN$_2$O$_5$ (M$^+$) 530.0714, found 530.0704.

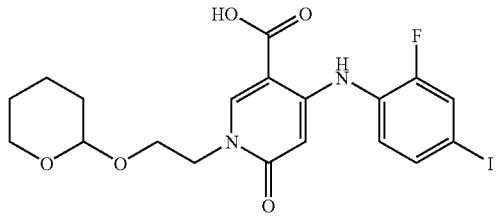

Step B: Preparation of 4-(2-fluoro-4-iodoanilino)-6-oxo-1-[2-(tetrahydro-2H-pyran-2-yloxy)ethyl]-1,6-dihydro-3-pyridinecarboxylic acid Ethyl 4-(2-fluoro-4-iodoanilino)-6-oxo-1-[2-(tetrahydro-2H-pyran-2-yloxy)ethyl]-1,6-dihydro-3-pyridinecarboxylate was dissolved in EtOH and treated with 1 M NaOH, as for example 1, step C, to hydrolyse the ester to give 4-(2-fluoro-4-iodoanilino)-6-oxo-1-[2-(tetrahydro-2H-pyran-2-yloxy)ethyl]-1,6-dihydro-3-pyridinecarboxylic acid as a pale yellow solid (88%), used directly in the next step. $^1$H NMR [(CD$_3$)$_2$SO, 400 MHz] δ 13.33 (v br s, 1H), 9.67 (br s, 1H), 8.46 (s, 1H), 7.77 (dd, J=10.0, 1.8 Hz, 1H), 7.60 (dd, J=8.3, 0.9 Hz, 1H), 7.32 (t, J=8.5 Hz, 1H), 5.50 (s, 1H), 4.60-4.56 (m, 1H), 4.12-4.06 (m, 2H), 3.79-3.71 (m, 1H), 3.60-3.35 (m, 3H), 1.75-1.27 (m, 6H). LCMS (APCI$^-$) calcd for C$_{19}$H$_{19}$FIN$_2$O$_5$ 501 (MH$^+$), found 501.

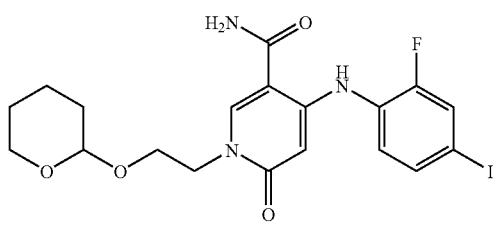

Step C: Preparation of 4-(2-fluoro-4-iodoanilino)-6-oxo-1-[2-(tetrahydro-2H-pyran-2-yloxy)ethyl]-1,6-dihydro-3-pyridinecarboxamide 4-(2-Fluoro-4-iodoanilino)-6-oxo-1-[2-(tetrahydro-2H-pyran-2-yloxy)ethyl]-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (5% MeOH/CH$_2$Cl$_2$ as eluant) to afford 4-(2-fluoro-4-iodoanilino)-6-oxo-1-[2-(tetrahydro-2H-pyran-2-yloxy)ethyl]-1,6-dihydro-3-pyridinecarboxamide as an oily cream solid (76%), used directly in the next step. $^1$H NMR [(CD$_3$)$_2$SO, 400 MHz] δ 10.49 (s, 1H), 8.34 (s, 1H), 7.93 (br s, 1H), 7.74 (dd, J=10.2, 1.8 Hz, 1H), 7.57 (dd, J=8.7, 1.0 Hz, 1H), 7.48 (br s, 1H), 7.30 (t, J=8.6 Hz, 1H), 5.55 (s, 1H), 4.58-4.52 (m, 1H), 4.04-3.91 (m, 2H), 3.82-3.75 (m, 1H), 3.63-3.35 (m, 3H), 1.73-1.26 (m, 6H). HRMS (EI$^+$) calcd C$_{19}$H$_{21}$FIN$_3$O$_4$ (M$^+$) 501.0561, found 501.0564.

Step D: Preparation of 4-(2-fluoro-4-iodoanilino)-1-(2-hydroxyethyl)-6-oxo-1,6-dihydro-3-pyridinecarboxamide 4-(2-Fluoro-4-iodoanilino)-6-oxo-1-[2-(tetrahydro-2H-pyran-2-yloxy)ethyl]-1,6-dihydro-3-pyridinecarboxamide (118 mg, 0.24 mmol) was dissolved in EtOH (8 mL), to which was added 1 M HCl (2 mL). This mixture was stirred at R.T. for 2 h., then diluted with water (80 mL). The resulting solution was extracted with EtOAc (3×40 mL), then the combined EtOAc fractions washed with water (2×50 mL) and brine (50 mL), then dried (Na$_2$SO$_4$). Removal of the solvent under reduced pressure afforded 4-(2-fluoro-4-iodoanilino)-1-(2-hydroxyethyl)-6-oxo-1,6-dihydro-3-pyridinecarboxamide as a white solid (95 mg, 97%), m.p. (EtOAc/MeOH) 212-215° C. $^1$H NMR [(CD$_3$)$_2$SO, 400 MHz] δ 10.45 (s, 1H), 8.27 (s, 1H), 7.94 (br s, 1H), 7.74 (dd, J=10.1, 1.7 Hz, 1H), 7.57 (br d, J=8.6 Hz, 1H), 7.48 (br s, 1H), 7.29 (t, J=8.5 Hz, 1H), 5.55 (s, 1H), 4.93 (t, J=5.3 Hz, 1H), 3.85 (t, J=5.5 Hz, 2H), 3.60 (q, J=5.4 Hz, 2H). Anal. Calcd for C$_{14}$H$_{13}$FIN$_3$O$_3$: C, 40.3; H, 3.1; N, 10.1. Found: C, 40.4; H, 2.9; N, 9.8.

EXAMPLE 23

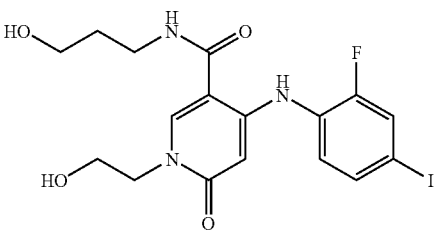

4-(2-Fluoro-4-iodoanilino)-1-(2-hydroxyethyl)-N-(3-hydroxypropyl)-6-oxo-1,6-dihydro-3-pyridinecarboxamide

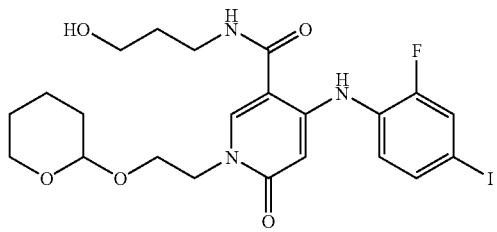

Step A: Preparation of 4-(2-fluoro-4-iodoanilino)-N-(3-hydroxypropyl)-6-oxo-1-[2-(tetrahydro-2H-pyran-2-yloxy)ethyl]-1,6-dihydro-3-pyridinecarboxamide 4-(2-Fluoro-4-iodoanilino)-6-oxo-1-[2-(tetrahydro-2H-pyran-2-yloxy)ethyl]-1,6-dihydro-3-pyridinecarboxylic acid was reacted with pentafluorophenyl trifluoroacetate in the presence of pyridine in THF as for example 4, step A, to afford the corresponding pentafluorophenyl ester. The crude ester was then reacted directly with 3-aminopropanol in THF in the presence of DIEA as for example 4, step B. The reaction solvent was removed under reduced pressure and the resulting oil purified by chromatography on silica gel (5% MeOH/CH$_2$Cl$_2$) to give 4-(2-fluoro-4-iodoanilino)-N-(3-hydroxypropyl)-6-oxo-1-[2-(tetrahydro-2H-pyran-2-yloxy)ethyl]-1,6-dihydro-3-pyridinecarboxamide as a clear oil (83%), used directly in the next step. $^1$H NMR [(CD$_3$)$_2$SO, 400 MHz] δ 10.23 (s, 1H), 8.43 (t, J=5.5 Hz, 1H), 8.25 (s, 1H), 7.74 (dd, J=10.2, 1.9 Hz, 1H), 7.57 (dd, J=8.3, 1.0 Hz, 1H), 7.30 (t, J=8.5 Hz, 1H), 5.57 (s, 1H), 4.59-4.55 (m, 1H), 4.48 (t, J=5.1 Hz, 1H), 4.05-3.93 (m, 2H), 3.82-3.74 (m, 1H), 3.64-3.52 (m, 2H), 3.46 (q, J=5.9 Hz, 2H), 3.43-3.24 (m, 3H), 1.70-1.32 (m, 8H). HRMS (EI$^+$) calcd C$_{22}$H$_{27}$FIN$_3$O$_5$ (M$^+$) 559.0980, found 559.0996.

Step B: Preparation of 4-(2-fluoro-4-iodoanilino)-1-(2-hydroxyethyl)-N-(3-hydroxypropyl)-6-oxo-1,6-dihydro-3-pyridinecarboxamide 4-(2-Fluoro-4-iodoanilino)-N-(3-hydroxypropyl)-6-oxo-1-[2-(tetrahydro-2H-pyran-2-yloxy)ethyl]-1,6-dihydro-3-pyridinecarboxamide was dissolved in EtOH and treated with 1 M HCl, as for example 22, step D, deprotecting the tetrahydropyranyl ether to give 4-(2-fluoro-4-iodoanilino)-1-(2-hydroxyethyl)-N-(3-hydroxypropyl)-6-oxo-1,6-dihydro-3-pyridinecarboxamide as a white solid which was recrystallised from EtOAc/MeOH (97%), m.p. (EtOAc/MeOH) 174-176° C. $^1$H NMR [(CD$_3$)$_2$SO, 400 MHz] δ 10.18 (s, 1H), 8.43 (t, J=5.4 Hz, 1H), 8.17 (s, 1H), 7.74 (dd, J=10.2, 1.8 Hz, 1H), 7.57 (br d, J=8.4 Hz, 1H), 7.28 (t, J=8.5 Hz, 1H), 5.57 (s, 1H), 4.93 (t, J=5.4 Hz, 1H), 4.50 (t, J=5.1 Hz, 1H), 3.86 (t, J=5.6 Hz, 2H), 3.60 (q, J=5.5 Hz, 2H), 3.46 (q, J=5.7 Hz, 2H), 3.31-3.23 (m, 2H), 1.66 (pentet, J=6.7 Hz, 2H). Anal. Calcd for C$_{17}$H$_{19}$FIN$_3$O$_4$: C, 43.0; H, 4.0; N, 8.8. Found: C, 43.3; H, 3.8; N, 8.9.

EXAMPLE 24

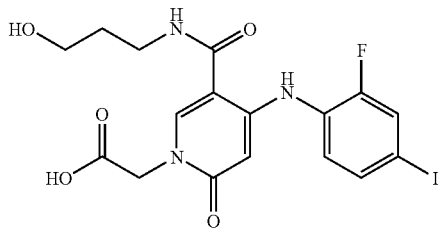

(4-(2-Fluoro-4-iodoanilino)-5-{[(3-hydroxypropyl)amino]carbonyl}-2-oxo-1(2H)-pyridinyl)acetic acid

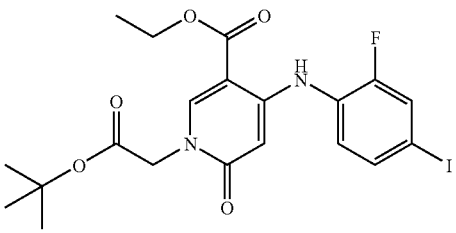

Step A: Preparation of ethyl 1-(2-tert-butoxy-2-oxoethyl)-4-(2-fluoro-4-iodoanilino)-6-oxo-1,6-dihydro-3-pyridinecarboxylate Ethyl 4-(2-fluoro-4-iodoanilino)-6-oxo-1,6-dihydro-3-pyridinecarboxylate was reacted with NaH and t-butylbromoacetate in DMF under the same conditions as for example 22, step A to give a crude solid which was purified by column chromatography on silica gel (1% MeOH/CH$_2$Cl$_2$ as eluant). Ethyl 1-(2-tert-butoxy-2-oxoethyl)-4-(2-fluoro-4-iodoanilino)-6-oxo-1,6-dihydro-3-pyridinecarboxylate was isolated as a white solid (72%), m.p. (EtOAc/hexanes) 149-151° C. $^1$H NMR [(CD$_3$)$_2$SO, 400 MHz] δ 9.34 (s, 1H), 8.57 (s, 1H), 7.78 (dd, J=10.0, 1.9 Hz, 1H), 7.61 (dd, J=8.4, 1.0 Hz, 1H), 7.31 (t, J=8.5 Hz, 1H), 5.43 (d, J=1.2 Hz, 1H), 4.62 (s, 2H), 4.31 (q, J=7.1 Hz, 2H), 1.42 (s, 9H), 1.33 (t, J=7.1 Hz, 3H). Anal Calcd for C$_{20}$H$_{22}$FIN$_2$O$_5$: C, 46.5; H, 4.3; N, 5.4. Found: C, 46.7; H, 4.2; N, 5.5.

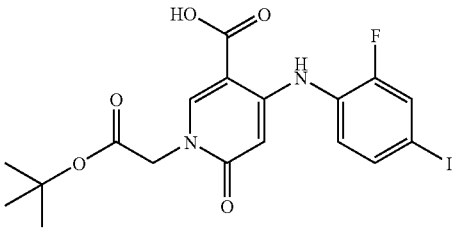

Step B: Preparation of 1-(2-tert-butoxy-2-oxoethyl)-4-(2-fluoro-4-iodoanilino)-6-oxo-1,6-dihydro-3-pyridinecarboxylic acid Ethyl 1-(2-tert-butoxy-2-oxoethyl)-4-(2-fluoro-4-iodoanilino)-6-oxo-1,6-dihydro-3-pyridinecarboxylate (510 mg, 0.99 mmol) was suspended in EtOH (120 mL), to which was added 1 M K$_2$CO$_3$ (80 mL). This mixture was stirred at R.T. for 15 h., then diluted with 1 M HCl (100 mL) and the resulting precipitate extracted into EtOAc (3×100 mL). The combined EtOAc fractions were washed with water (3×100 mL), brine (100 mL) and dried (Na$_2$SO$_4$). The solvent was then removed under reduced pressure to afford a crude solid which was purified by column chromatography on silica gel (5% MeOH/CH$_2$Cl$_2$ as eluant) to give 1-(2-tert-butoxy-2-oxoethyl)-4-(2-fluoro-4-iodoanilino)-6-oxo-1,6-dihydro-3-pyridinecarboxylic acid as a white solid (64%), used directly in the next step. $^1$H NMR [(CD$_3$)$_2$SO, 400 MHz] δ 11.03 (v br s, 1H), 8.33 (s, 1H), 7.71 (dd, J=10.2, 1.9 Hz, 1H), 7.55 (dd, J=8.4, 1.0 Hz, 1H), 7.29 (t, J=8.3 Hz, 1H), 5.49 (s, 1H), 4.55 (s, 2H), 1.39 (s, 9H). HRMS (EI$^+$) calcd C$_{18}$H$_{18}$FIN$_2$O$_5$ (M$^+$) 488.0245, found 488.0247.

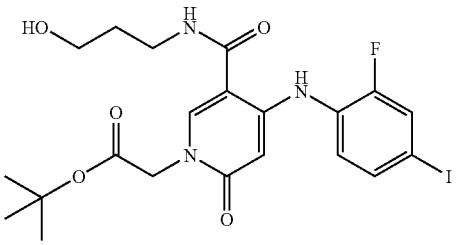

Step C: Preparation of tert-butyl (4-(2-fluoro-4-iodoanilino)-5-{[(3-hydroxypropyl)amino]carbonyl}-2-oxo-1(2H)-pyridinyl)acetate 1-(2-tert-Butoxy-2-oxoethyl)-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester. The crude ester was then reacted directly with 3-aminopropanol in THF in the presence of DIEA as for example 4, step B. The reaction solvent was removed under reduced pressure and the resulting oil purified by chromatography on silica gel (50% acetone/$CH_2Cl_2$ as eluant) to give tert-butyl(4-(2-fluoro-4-iodoanilino)-5-{[(3-hydroxypropyl)amino]carbonyl}-1(2H)-pyridinyl)acetate as a white foam (92%), used directly in the next step. $^1$H NMR [($CD_3$)$_2$SO, 400 MHz] δ 10.09 (s, 1H), 8.39 (t, J=5.5 Hz, 1H), 8.19 (s, 1H), 7.75 (dd, J=10.4, 1.9 Hz, 1H), 7.58 (br d, J=8.4 Hz, 1H), 7.29 (t, J=8.5 Hz, 1H), 5.55 (s, 1H), 4.50-4.43 (m, 3H), 3.47 (q, J=5.9 Hz, 2H), 3.25 (t, J=7.1 Hz, 2 H—by $D_2O$ exchange), 1.67 (pentet, J=6.7 Hz, 2H), 1.42 (s, 9H). HRMS (EI$^+$) calcd $C_{21}H_{25}FIN_3O_5$ (M$^+$) 545.0823, found 545.0825.

Step D: Preparation of (4-(2-fluoro-4-iodoanilino)-5-{[(3-hydroxypropyl)amino]carbonyl}-2-oxo-1(2H)-pyridinyl) acetic acid tert-Butyl (4-(2-fluoro-4-iodoanilino)-5-{[(3-hydroxypropyl)amino]carbonyl}-2-oxo-1(2H)-pyridinyl)acetate was dissolved in EtOH and treated with 1 M NaOH, as for example 1, step C, to hydrolyse the t-butyl ester to give (4-(2-fluoro-4-iodoanilino)-5-{[(3-hydroxypropyl)amino] carbonyl}2-oxo-1(2H)-pyridinyl)acetic acid as a white solid (86%), m.p. (EtOAc/MeOH) 199-202° C. $^1$H NMR [(CD$_3$)$_2$SO, 400 MHz] δ 10.12 (s, 1H), 8.39 (t, J=5.3 Hz, 1H), 8.22 (s, 1H), 7.74 (dd, J=10.2, 1.9 Hz, 1H), 7.57 (br d, J=8.4 Hz, 1H), 7.28 (t, J=8.5 Hz, 1H), 5.54 (s, 1H), 4.53-4.42 (m, 3H), 3.45 (t, J=6.3 Hz, 2 H—by $D_2O$ exchange), 3.24 (t, J=7.0 Hz, 2 H—by $D_2O$ exchange), 1.66 (pentet, J=6.6 Hz, 2H). HRMS (FAB$^+$) calcd $C_{17}H_{18}FIN_3O_5$ (MH$^+$) 490.0275, found 490.0279.

EXAMPLE 25

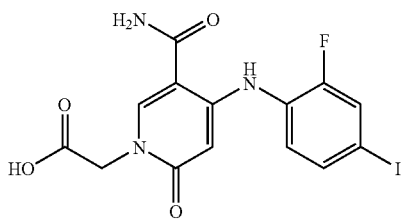

5-(Aminocarbonyl)-4-(2-fluoro-4-iodoanilino)-2-oxo-1(2H)-pyridinyl)acetic acid

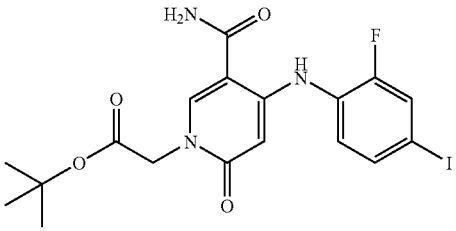

Step A: Preparation of tert-butyl (5-(aminocarbonyl)-4-(2-fluoro-4-iodoanilino)-2-oxo-1(2H)-pyridinyl)acetate 1-(2-tert-Butoxy-2-oxoethyl)-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (50% acetone/$CH_2Cl_2$ as eluant) to afford tert-butyl (5-(aminocarbonyl)-4-(2-fluoro-4-iodoanilino)-2-oxo-1(2H)-pyridinyl)acetate as a white solid (93%), used directly in the next step. $^1$H NMR [(CD$_3$)$_2$SO, 400 MHz] δ 10.40 (s, 1H), 8.30 (s, 1H), 7.80 (br s, 1H), 7.74 (dd, J=10.2, 1.9 Hz, 1H), 7.58 (br d, J=8.4 Hz, 1H), 7.54 (br s, 1H), 7.30 (t, J=8.5 Hz, 1H), 5.53 (d, J=0.8 Hz, 1H), 4.46 (s, 2H), 1.43 (s, 9H). HRMS (FAB$^+$) calcd $C_{18}H_{20}FIN_3O_4$ (MH$^+$) 488.0483, found 488.0471.

Step B: Preparation of (5-(aminocarbonyl)-4-(2-fluoro-4-iodoanilino)-2-oxo-1(2H)-pyridinyl)acetic acid tert-Butyl (5-(aminocarbonyl)-4-(2-fluoro-4-iodoanilino)-2-oxo-1(2H)-pyridinyl)acetate (225 mg, 0.46 mmol) was dissolved in a mixture of $CH_2Cl_2$ (10 mL) and trifluoroacetic acid (10 mL) and stirred at R.T. for 2 h. All solvent was evaporated under a stream of nitrogen and the resulting oil was redissolved in MeOH (10 mL) to which was added sat. NaHCO$_3$ (10 mL). This mixture was stirred at R.T for 1 h. then 1 M HCl (50 mL) added and the resulting white precipitate collected by filtration. Purification was carried out by recrystallisation from EtOAc/MeOH to afford (5-(aminocarbonyl)-4-(2-fluoro-4-iodoanilino)-2-oxo-1(2H)-pyridinyl)acetic acid as a white solid (76 mg, 38%), m.p. (EtOAc/MeOH) 296-300° C. $^1$H NMR [(CD$_3$)$_2$SO, 400 MHz] δ 13.10 (v br s, 1H), 10.42 (s, 1H), 8.32 (s, 1H), 7.86 (br s, 1H), 7.75 (dd, J=10.2, 1.9 Hz, 1H), 7.58 (dd, J=8.4, 0.8 Hz, 1H), 7.52 (br s, 1H), 7.30 (t, J=8.5 Hz, 1H), 5.53 (d, J=1.0 Hz, 1H), 4.49 (s, 2H). Anal. Calcd for $C_{14}H_{11}FIN_3O_4$·0.5$H_2O$: C, 38.2; H, 2.7; N, 9.5. Found: C, 38.0; H, 2.4; N, 9.1.

EXAMPLE 26

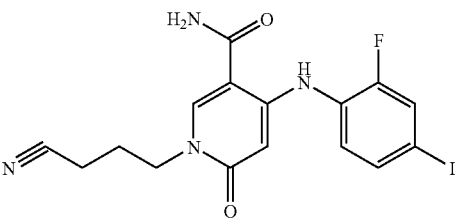

1-(3-Cyanopropyl)-4-(2-fluoro-4-iodoanilino)-6-oxo-1,6-dihydro-3-pyridinecarboxamide

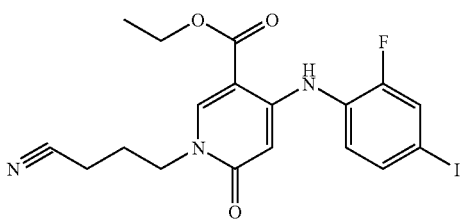

Step A: Preparation of ethyl 1-(3-cyanopropyl)-4-(2-fluoro-4-iodoanilino)-6-oxo-1,6-dihydro-3-pyridinecarboxylate Ethyl 4-(2-fluoro-4-iodoanilino)-6-oxo-1,6-dihydro-3-pyridinecarboxylate was reacted with NaH and 4-bromobutyronitrile in DMF under the same conditions as for example 22, step A to give a crude solid which was purified by column chromatography on silica gel (50% EtOAc/hexanes as eluant). Ethyl 1-(3-cyanopropyl)-4-(2-fluoro-4-iodoanilino)-6-oxo-1,6-dihydro-3-pyridinecarboxylate was isolated as a white solid (67%), m.p. (EtOAc) 157-159° C. $^1$H NMR [(CD$_3$)$_2$SO, 400 MHz] δ 9.30 (s, 1H), 8.51 (s, 1H), 7.77 (dd, J=10.1, 1.9 Hz, 1H), 7.61 (br d, J=8.4 Hz, 1H), 7.30 (t, J=8.5 Hz, 1H), 5.46 (s, 1H), 4.31 (q, J=7.1 Hz, 2H), 3.96 (t, J=7.2 Hz, 2H), 2.53 (t, J=7.2 Hz, 2H), 1.93 (pentet, J=7.2 Hz, 2H), 1.33 (t, J=7.1 Hz, 3H). Anal. Calcd for C$_{18}$H$_{17}$FIN$_3$O$_3$: C, 46.1; H, 3.7; N, 9.0. Found: C, 46.4; H, 3.6; N, 8.9.

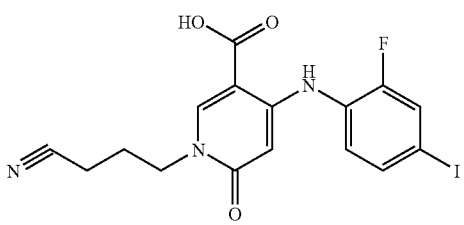

Step B: Preparation of 1-(3-cyanopropyl)-4-(2-fluoro-4-iodoanilino)-6-oxo-1,6-dihydro-3-pyridinecarboxylic acid Ethyl 1-(3-cyanopropyl)-4-(2-fluoro-4-iodoanilino)-6-oxo-1,6-dihydro-3-pyridinecarboxylate was dissolved in EtOH and treated with 1 M NaOH, as for example 1, step C, to hydrolyse the ester to give 1-(3-cyanopropyl)-4-(2-fluoro-4-iodoanilino)-6-oxo-1,6-dihydro-3-pyridinecarboxylic acid as a white solid (100%), used directly in the next step. $^1$H NMR [(CD$_3$)$_2$SO, 400 MHz] δ 13.10 (v br s, 1H), 9.72 (br s, 1H), 8.48 (s, 1H), 7.76 (dd, J=10.1, 1.9 Hz, 1H), 7.60 (dd, J=8.4, 0.9 Hz, 1H), 7.30 (t, J=8.5 Hz, 1H), 5.49 (s, 1H), 3.95 (t, J=7.1 Hz, 2H), 2.52 (t, J=7.2 Hz, 2H), 1.93 (pentet, J=7.2 Hz, 2H). HRMS (FAB$^+$) calcd C$_{16}$H$_{14}$FIN$_3$O$_3$ (MH$^+$) 442.0064, found 442.0060.

Step C: Preparation of 1-(3-cyanopropyl)-4-(2-fluoro-4-iodoanilino)-6-oxo-1,6-dihydro-3-pyridinecarboxamide 1-(3-Cyanopropyl)-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (5% MeOH/CH$_2$Cl$_2$ as eluant) to afford 1-(3-cyanopropyl)-4-(2-fluoro-4-iodoanilino)-6-oxo-1,6-dihydro-3-pyridinecarboxamide as a white solid (70%), m.p. (EtOAc) 146-150° C. $^1$H NMR [(CD$_3$)$_2$SO, 400 MHz] δ 10.36 (s, 1H), 8.28 (s, 1H), 7.91 (br s, 1H), 7.73 (dd, J=10.2, 1.9 Hz, 1H), 7.57 (ddd, J=8.4, 1.9, 0.9 Hz, 1H), 7.48 (br s, 1H), 7.29 (t, J=8.5 Hz, 1H), 5.56 (d, J=0.9 Hz, 1H), 3.87 (t, J=7.2 Hz, 2H), 2.55 (t, J=7.2 Hz, 2H), 1.96 (pentet, J=7.2 Hz, 2H). Anal. Calcd for C$_{16}$H$_{14}$FIN$_4$O$_2$: C, 43.7; H, 3.2; N, 12.7. Found: C, 44.2; H, 3.1; N, 12.5

EXAMPLE 27

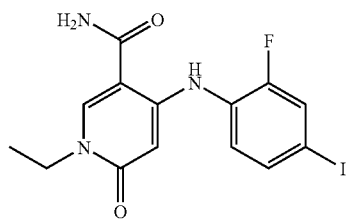

1-Ethyl-4-(2-fluoro-4-iodoanilino)-6-oxo-1,6-dihydro-3-pyridinecarboxamide

Step A: Preparation of ethyl 1-ethyl-4-(2-fluoro-4-iodoanilino)-6-oxo-1,6-dihydro-3-pyridinecarboxylate Ethyl 4-(2-fluoro-4-iodoanilino)-6-oxo-1,6-dihydro-3-pyridinecarboxylate was reacted with NaH and iodoethane in DMF under the same conditions as for example 22, step A to give a crude solid which was purified by column chromatography on silica gel (50% EtOAc/hexanes as eluant). Ethyl 1-ethyl-4-(2-fluoro-4-iodoanilino)-6-oxo-1,6-dihydro-3-pyridinecarboxylate was isolated as white needles (61%), m.p. (EtOAc/hexanes) 138-142° C. $^1$H NMR [(CD$_3$)$_2$SO, 400 MHz] δ 9.29 (s, 1H), 8.52 (s, 1H), 7.77 (dd, J=10.1, 1.9 Hz, 1H), 7.60 (ddd, J=8.4, 2.0, 0.8 Hz, 1H), 7.31 (t, J=8.5 Hz, 1H), 5.45 (s, 1H), 4.30 (q, J=7.1 Hz, 2H), 3.93 (q, J=7.1 Hz, 2H), 1.33 (t, J=7.1 Hz, 3H), 1.20 (t, J=7.1 Hz, 3H). Anal. Calcd for C$_{16}$H$_{16}$FIN$_2$O$_3$: C, 44.7; H, 3.8; N, 6.5. Found: C, 45.0; H, 3.6; N, 6.4.

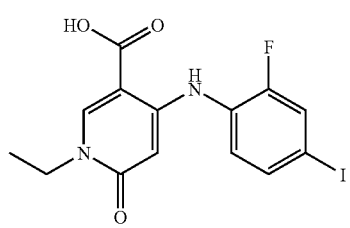

Step B: Preparation of 1-ethyl-4-(2-fluoro-4-iodoanilino)-6-oxo-1,6-dihydro-3-pyridinecarboxylic acid Ethyl 1-ethyl-4-(2-fluoro-4-iodoanilino)-6-oxo-1,6-dihydro-3-pyridinecarboxylate was dissolved in EtOH and treated with 1 M NaOH, as for example 1, step C, to hydrolyse the ester to give 1-ethyl-4-(2-fluoro-4-iodoanilino)-6-oxo-1,6-dihydro-3-pyridinecarboxylic acid as a white solid (100%), used directly in the next step. $^1$H NMR [(CD$_3$)$_2$SO, 400 MHz] δ 13.13 (v br s, 1H), 9.66 (br s, 1H), 8.49 (s, 1H), 7.75 (dd, J=10.1, 1.9 Hz, 1H), 7.59 (ddd, J=8.4, 2.0, 0.9 Hz, 1H), 7.31 (t, J=8.5 Hz, 1H), 5.49 (s, 1H), 3.91 (q, J=7.1 Hz, 2H), 1.19 (t, J=7.1 Hz, 3H). HRMS (EI$^+$) calcd C$_{14}$H$_{12}$FIN$_2$O$_3$ (M$^+$) 401.9877, found 401.9872.

Step C: Preparation of 1-ethyl-4-(2-fluoro-4-iodoanilino)-6-oxo-1,6-dihydro-3-pyridinecarboxamide 1-Ethyl-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (5% MeOH/CH$_2$Cl$_2$ as eluant) to afford 1-ethyl-4-(2-fluoro-4-iodoanilino)-6-oxo-1,6-dihydro-3-pyridinecarboxamide as a white solid (84%), m.p. (EtOAc) 260-262° C. $^1$H NMR [(CD$_3$)$_2$SO, 400 MHz] δ 10.38 (s, 1H), 8.31 (s, 1H), 7.90 (br s, 1H), 7.73 (dd, J=10.2, 1.9 Hz, 1H), 7.57 (ddd, J=8.4, 1.9, 0.9 Hz, 1H), 7.46 (br s, 1H), 7.29 (t, J=8.5 Hz, 1H), 5.55 (d, J=0.9 Hz, 1H), 3.83 (q, J=7.1 Hz, 2H), 1.23 (t, J=7.1 Hz, 3H). Anal. Calcd for C$_{14}$H$_{13}$FIN$_3$O$_2$: C, 41.9; H, 3.3; N, 10.5. Found: C, 42.4; H, 3.4; N, 10.5.

EXAMPLE 28

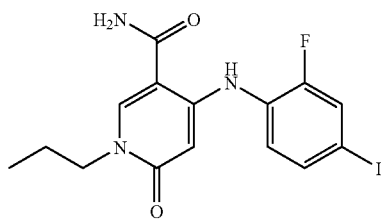

4-(2-Fluoro-4-iodoanilino)-6-oxo-1-propyl-1,6-dihydro-3-pyridinecarboxamide

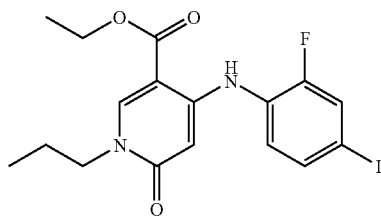

Step A: Preparation of ethyl 4-(2-fluoro-4-iodoanilino)-6-oxo-1-propyl-1,6-dihydro-3-pyridinecarboxylate Ethyl 4-(2-fluoro-4-iodoanilino)-6-oxo-1,6-dihydro-3-pyridinecarboxylate was reacted with NaH and bromopropane in DMF under the same conditions as for example 22, step A to give a crude solid which was purified by column chromatography on silica gel (50% EtOAc/hexanes as eluant). Ethyl 4-(2-fluoro-4-iodoanilino)-6-oxo-1-propyl-1,6-dihydro-3-pyridinecarboxylate was isolated as a white solid (54%), m.p. (EtOAc/hexanes) 147-150° C. $^1$H NMR [(CD$_3$)$_2$SO, 400 MHz] δ 9.29 (s, 1H), 8.50 (s, 1H), 7.76 (dd, J=10.1, 1.9 Hz, 1H), 7.60 (ddd, J=8.4, 2.0, 0.8 Hz, 1H), 7.31 (t, J=8.5 Hz, 1H), 5.46 (d, J=1.3 Hz, 1H), 4.30 (q, J=7.1 Hz, 2H), 3.85 (t, J=7.3 Hz, 2H), 1.62 (sextet, J=7.3 Hz, 2H), 1.33 (t, J=7.1 Hz, 3H), 0.85 (t, J=7.4 Hz, 3H). Anal. Calcd for C$_{17}$H$_{18}$FIN$_2$O$_3$: C, 46.0; H, 4.1; N, 6.3. Found: C, 45.8; H, 3.9; N, 6.0.

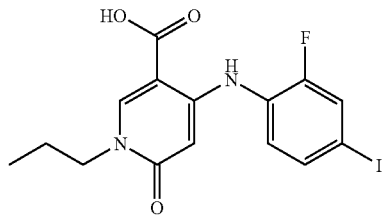

Step B: Preparation of 4-(2-fluoro-4-iodoanilino)-6-oxo-1-propyl-1,6-dihydro-3-pyridinecarboxylic acid Ethyl 4-(2-fluoro-4-iodoanilino)-6-oxo-1-propyl-1,6-dihydro-3-pyridinecarboxylate was dissolved in EtOH and treated with 1 M NaOH, as for example 1, step C, to hydrolyse the ester to give 4-(2-fluoro-4-iodoanilino)-6-oxo-1-propyl-1,6-dihydro-3-pyridinecarboxylic acid as a white solid (100%), used directly in the next step. $^1$H NMR [(CD$_3$)$_2$SO, 400 MHz] δ 13.13 (v br s, 1H), 9.70 (br s, 1H), 8.46 (s, 1H), 7.75 (dd, J=10.1, 1.9 Hz, 1H), 7.59 (ddd, J=8.4, 2.0, 0.8 Hz, 1H), 7.33 (t, J=8.5 Hz, 1H), 5.49 (s, 1H), 3.84 (t, J=7.2 Hz, 2H), 1.61 (sextet, J=7.4 Hz, 2H), 0.85 (t, J=7.4 Hz, 3H). HRMS (EI$^+$) calcd C$_{15}$H$_{14}$FIN$_2$O$_3$ (M$^+$) 416.0033, found 416.0036.

Step C: Preparation of 4-(2-fluoro-4-iodoanilino)-6-oxo-1-propyl-1,6-dihydro-3-pyridinecarboxamide 4-(2-Fluoro-4-iodoanilino)-6-oxo-1-propyl-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (5% MeOH/CH$_2$Cl$_2$ as eluant) to afford 4-(2-fluoro-4-iodoanilino)-6-oxo-1-propyl-1,6-dihydro-3-pyridinecarboxamide as a white solid (97%), m.p. (EtOAc) 218-220° C. $^1$H NMR [(CD$_3$)$_2$SO, 400 MHz] δ 10.43 (s, 1H), 8.30 (s, 1H), 7.80 (br s, 1H), 7.73 (dd, J=10.2, 1.9 Hz, 1H), 7.56 (dd, J=8.4, 0.9 Hz, 1H), 7.46 (br s, 1H), 7.30 (t, J=8.5 Hz, 1H), 5.55 (d, J=0.7 Hz, 1H), 3.75 (t, J=7.3 Hz, 2H), 1.65 (sextet, J=7.4 Hz, 2H), 0.87 (t, J=7.4 Hz, 3H). Anal. Calcd for C$_{15}$H$_{15}$FIN$_3$O$_2$: C, 43.4; H, 3.6; N, 10.1. Found: C, 43.5; H, 3.7; N, 9.9.

EXAMPLE 29

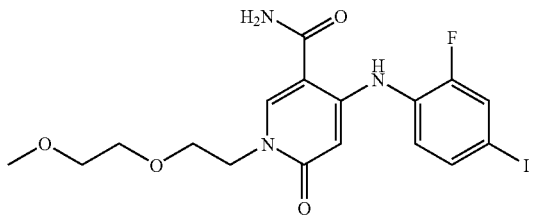

4-(2-Fluoro-4-iodoanilino)-1-[2-(2-methoxyethoxy)ethyl]-6-oxo-1,6-dihydro-3-pyridinecarboxamide

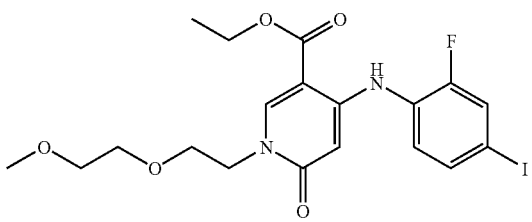

Step A: Preparation of ethyl 4-(2-fluoro-4-iodoanilino)-1-[2-(2-methoxyethoxy)ethyl]-6-oxo-1,6-dihydro-3-pyridinecarboxylate Ethyl 4-(2-fluoro-4-iodoanilino)-6-oxo-1,6-dihydro-3-pyridinecarboxylate was reacted with NaH and 1-bromo-2-(2-methoxyethoxy)ethane in DMF under the same conditions as for example 22, step A to give a crude solid which was purified by column chromatography on silica gel (1% MeOH/CH$_2$Cl$_2$ as eluant). Ethyl 4-(2-fluoro-4-iodoanilino)-1-[2-(2-methoxyethoxy)ethyl]-6-oxo-1,6-dihydro-3-pyridinecarboxylate was isolated as a pale yellow oil (41%). $^1$H NMR [(CD$_3$)$_2$SO, 400 MHz] δ 9.30 (s, 1H), 8.43 (s, 1H), 7.77 (dd, J=10.1, 1.9 Hz, 1H), 7.60 (ddd, J=8.3, 1.9, 0.8 Hz, 1H), 7.31 (t, J=8.5 Hz, 1H), 5.44 (d, J=1.3 Hz, 1H), 4.31 (q, J=7.1 Hz, 2H), 4.06 (t, J=5.1 Hz, 2H), 3.61 (t, J=5.2 Hz, 2H), 3.54-3.50 (m, 2H), 3.43-3.39 (m, 2H), 3.22 (s, 3H), 1.32 (t, J=7.1 Hz, 3H). HRMS (EI$^+$) calcd C$_{19}$H$_{22}$FIN$_2$O$_5$ (M$^+$) 504.0558, found 504.0552.

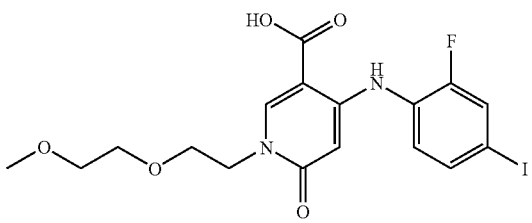

Step B: Preparation of 4-(2-fluoro-4-iodoanilino)-1-[2-(2-methoxyethoxy)ethyl]-6-oxo-1,6-dihydro-3-pyridinecarboxylic acid Ethyl 4-(2-fluoro-4-iodoanilino)-1-[2-(2-methoxyethoxy)ethyl]-6-oxo-1,6-dihydro-3-pyridinecarboxylate was dissolved in EtOH and treated with 1 M NaOH, as for example 1, step C, to hydrolyse the ester to give 4-(2-fluoro-4-iodoanilino)-1-[2-(2-methoxyethoxy)ethyl]-6-oxo-1,6-dihydro-3-pyridinecarboxylic acid as a cream solid (99%), used directly in the next step. $^1$H NMR [(CD$_3$)$_2$SO, 400 MHz] δ 13.00 (v br s, 1H), 9.72 (br s, 1H), 8.41 (s, 1H), 7.75 (dd, J=10.1, 1.9 Hz, 1H), 7.60 (ddd, J=8.3, 1.9, 0.8 Hz, 1H), 7.32 (t, J=8.5 Hz, 1H), 5.47 (d, 1.2 Hz, 1H), 4.05 (t, J=5.2 Hz, 2H), 3.60 (t, J=5.2 Hz, 2H), 3.53-3.50 (m, 2H), 3.42-3.38 (m, 2H), 3.21 (s, 3H). HRMS (EI$^+$) calcd C$_{17}$H$_{18}$FIN$_2$O$_5$ (M$^+$) 476.0245, found 476.0236.

Step C: Preparation of 4-(2-fluoro-4-iodoanilino)-1-[2-(2-methoxyethoxy)ethyl]-6-oxo-1,6-dihydro-3-pyridinecarboxamide 4-(2-Fluoro-4-iodoanilino)-1-[2-(2-methoxyethoxy)ethyl]-6-oxo-1,6-dihydro-3-pyridine-carboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (50% acetone/CH$_2$Cl$_2$ as eluant) to afford 4-(2-fluoro-4-iodoanilino)-1-[2-(2-methoxyethoxy)ethyl]-6-oxo-1,6-dihydro-3-pyridinecarboxamide as a white solid (58%), m.p. (EtOAc/n-pentane) 114-116° C. $^1$H NMR [(CD$_3$)$_2$SO, 400 MHz] δ 10.43 (s, 1H), 8.28 (s, 1H), 7.81 (br s, 1H), 7.73 (dd, J=10.2, 1.9 Hz, 1H), 7.57 (dd, J=8.4, 0.9 Hz, 1H), 7.48 (br s, 1H), 7.29 (t, J=8.5 Hz, 1H), 5.55 (s, 1H), 3.95 (t, J=5.5 Hz, 2H), 3.63 (t, J=5.5 Hz, 2H), 3.54-3.51 (m, 2H), 3.43-3.39 (m, 2H), 3.22 (s, 3H). Anal. Calcd for C$_{17}$H$_{19}$FIN$_3$O$_4$: C, 43.0; H, 4.0; N, 8.8. Found: C, 42.6; H, 4.0; N, 8.6.

EXAMPLE 30

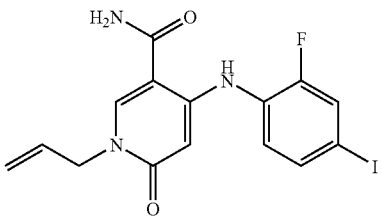

1-Allyl-4-(2-fluoro-4-iodoanilino)-6-oxo-1,6-dihydro-3-pyridinecarboxamide

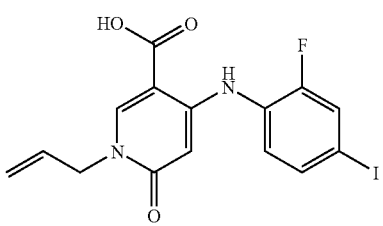

Step A: Preparation of ethyl 1-allyl-4-(2-fluoro-4-iodoanilino)-6-oxo-1,6-dihydro-3-pyridinecarboxylate Ethyl 4-(2-fluoro-4-iodoanilino)-6-oxo-1,6-dihydro-3-pyridinecarboxylate was reacted with NaH and allyl bromide in DMF under the same conditions as for example 22, step A to give a crude solid which was purified by column chromatography on silica gel (50% EtOAc/hexanes as eluant). Ethyl 1-allyl-4-(2-fluoro-4-iodoanilino)-6-oxo-1,6-dihydro-3-pyridinecarboxylate was isolated as a white solid (78%), m.p. (EtOAc) 138-141° C. $^1$H NMR [(CD$_3$)$_2$SO, 400 MHz] δ 9.30 (s, 1H), 8.45 (s, 1H), 7.77 (dd, J=10.1, 1.9 Hz, 1H), 7.61 (ddd, J=8.4, 2.0, 0.8 Hz, 1H), 7.31 (t, J=8.5 Hz, 1H), 5.98-5.87 (m, 1H), 5.47 (d, J=1.3 Hz, 1H), 5.19 (ddd, J=10.4, 2.7, 1.3 Hz, 1H), 5.12 (ddd, J=17.2, 3.0, 1.5 Hz, 1H), 4.54 (br d, J=5.5 Hz, 2H), 4.31 (q, J=7.1 Hz, 2H), 1.32 (t, J=7.1 Hz, 3H). Anal. Calcd for C$_{17}$H$_{16}$FIN$_2$O$_3$: C, 46.2; H, 3.7; N, 6.3. Found: C, 46.5; H, 3.6; N, 6.2.

Step B: Preparation of 1-allyl-4-(2-fluoro-4-iodoanilino)-6-oxo-1,6-dihydro-3-pyridinecarboxylic acid Ethyl 1-allyl-4-(2-fluoro-4-iodoanilino)-6-oxo-1,6-dihydro-3-pyridinecarboxylate was dissolved in EtOH and treated with 1 M NaOH, as for example 1, step C, to hydrolyse the ester to give 1-allyl-4-(2-fluoro-4-iodoanilino)-6-oxo-1,6-dihydro-3-pyridinecarboxylic acid as a white solid (99%), used directly in the next step. $^1$H NMR [(CD$_3$)$_2$SO, 400 MHz] δ 13.25 (v br s, 1H), 9.73 (br s, 1H), 8.41 (s, 1H), 7.75 (dd, J=10.1, 1.9 Hz, 1H), 7.60 (ddd, J=8.4, 2.0, 0.8 Hz, 1H), 7.32 (t, J=8.5 Hz, 1H), 5.98-5.86 (m, 1H), 5.49 (d, J=1.1 Hz, 1H), 5.19 (dd, J=10.3, 1.4 Hz, 1H), 5.14 (ddd, J=17.1, 3.0, 1.5 Hz, 1H), 4.52 (d, J=5.6 Hz, 2H). HRMS (EI$^+$) calcd C$_{15}$H$_{12}$FIN$_2$O$_3$ (M$^+$) 413.9877, found 413.9874.

Step C: Preparation of 1-allyl-4-(2-fluoro-4-iodoanilino)-6-oxo-1,6-dihydro-3-pyridinecarboxamide 1-Allyl-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (5% MeOH/CH$_2$Cl$_2$ as eluant) to afford 1-allyl-4-(2-fluoro-4-iodoanilino)-6-oxo-1,6-dihydro-3-pyridinecarboxamide as a white solid (85%), m.p. (EtOAc) 215-217° C. $^1$H NMR [(CD$_3$)$_2$SO, 400 MHz] δ 10.43 (s, 1H), 8.27 (s, 1H), 7.90 (br s, 1H), 7.73 (dd, J=10.2, 1.9 Hz, 1H), 7.57 (dd, J=8.3, 0.8 Hz, 1H), 7.49 (br s, 1H), 7.30 (t, J=8.5 Hz, 1H), 6.00-5.88 (m, 1H), 5.55 (s, 1H), 5.19 (dd, J=10.3, 1.3 Hz, 1H), 5.11 (ddd, J=17.2, 2.9, 1.5 Hz, 1H), 4.41 (d, J=5.5 Hz, 2H). Anal. Calcd for C$_{15}$H$_{13}$FIN$_3$O$_2$: C, 43.6; H, 3.2; N, 10.2. Found: C, 43.6; H, 3.3; N, 10.0.

EXAMPLE 31

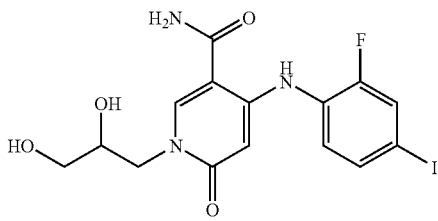

1-(2,3-Dihydroxypropyl)-4-(2-fluoro-4-iodoanilino)-6-oxo-1,6-dihydro-3-pyridinecarboxamide 1-Allyl-4-(2-fluoro-4-iodoanilino)-6-oxo-1,6-dihydro-3-pyridinecarboxamide (400 mg, 0.97 mmol) was dissolved in a mixture of t-butanol (60 mL) and water (60 mL) and to the resulting solution was added K$_3$Fe(CN)$_6$ (956 mg, 2.91 mmol), K$_2$CO$_3$ (400 mg, 2.91 mmol), OsO$_4$ (0.62 mL of a 4% w/w solution in water) and DABCO (108 mg, 0.97 mmol). The reaction mixture was stirred at R.T. for 15 h., then poured into 1 M Na$_2$S$_2$O$_4$ (200 mL) and extracted with EtOAc (3×100 mL). The combined EtOAc extracts were washed with water (100 mL), brine (100 mL) and dried (Na$_2$SO$_4$). The solvent was removed under reduced pressure and the resulting oil purified by column chromatography on silica gel (5% MeOH/CH$_2$Cl$_2$ as eluant) to give 1-(2,3-dihydroxypropyl)-4-(2-fluoro-4-iodoanilino)-6-oxo-1,6-dihydro-3-pyridinecarboxamide as a white solid (312 mg, 72%), m.p. (EtOAc) 210-213° C. $^1$H NMR [(CD$_3$)$_2$SO, 400 MHz] δ 10.44 (s, 1H), 8.26 (s, 1H), 7.87 (br s, 1H), 7.73 (dd, J=10.2, 1.9 Hz, 1H), 7.57 (dd, J=8.4, 0.9 Hz, 1H), 7.46 (br s, 1H), 7.29 (t, J=8.5 Hz, 1H), 5.56 (d, J=0.9 Hz, 1H), 4.96 (d, J=5.5 Hz, 1H), 4.70 (t, J=4.7 Hz, 1H), 4.14 (dd, J=13.1, 3.5 Hz, 1H), 3.79-3.70 (m, 1H), 3.51 (dd, J=13.1, 8.3 Hz, 1H), 3.40-3.30 (m, 2H). Anal. Calcd for C$_{15}$H$_{15}$FIN$_3$O$_4$: C, 40.3; H, 3.4; N, 9.4. Found: C, 40.7; H, 3.7; N, 9.5.

EXAMPLE 32

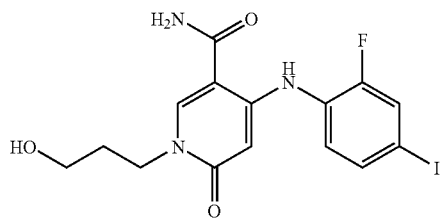

4-(2-Fluoro-4-iodoanilino)-1-(3-hydroxypropyl)-6-oxo-1,6-dihydro-3-pyridinecarboxamide

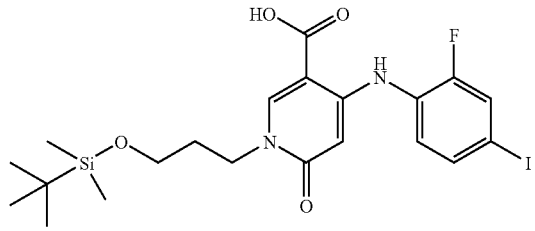

Step A: Preparation of 1-(3-{[tert-butyl(dimethyl)silyl]oxy}propyl)-4-(2-fluoro-4-iodoanilino)-6-oxo-1,6-dihydro-3-pyridinecarboxylic acid 3-Bromopropanol was protected as the t-butyldimethylsilyl ether according to a literature method [*J. Am. Chem. Soc.*, 94, 6190 (1972)]. Ethyl 4-(2-fluoro-4-iodoanilino)-6-oxo-1,6-dihydro-3-pyridinecarboxylate was reacted with NaH and the silyl ether-protected bromide in DMF under the same conditions as for example 22, step A to give a crude solid which was purified by column chromatography on silica gel (5% MeOH/CH$_2$Cl$_2$ as eluant). 1-(3-{[tert-Butyl(dimethyl)silyl]oxy}propyl)-4-(2-fluoro-4-iodoanilino)-6-oxo-1,6-dihydro-3-pyridinecarboxylic acid was isolated as a pale yellow glass (34%), used directly in the next step. $^1$H NMR [(CD$_3$)$_2$SO, 400 MHz] δ 11.20 (v br s, 1H), 8.23 (s, 1H), 7.71 (dd, J=10.2, 1.9 Hz, 1H), 7.55 (ddd, J=8.4, 2.0, 1.0 Hz, 1H), 7.30 (t, J=8.5 Hz, 1H), 5.55 (s, 1H), 3.89 (t, J=6.9 Hz, 2H), 3.60 (t, J=6.1 Hz, 2H), 1.79 (pentet, J=6.5 Hz, 2H), 0.87 (s, 9H), 0.04 (s, 6H).

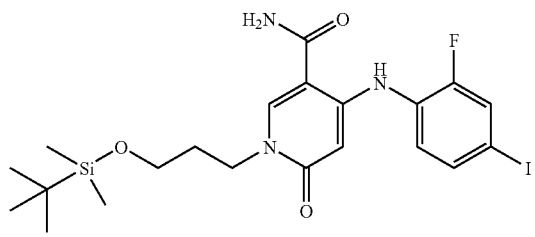

Step B: Preparation of 1-(3-{[tert-Butyl(dimethyl)silyl]oxy}propyl)-4-(2-fluoro-4-iodoanilino)-6-oxo-1,6-dihydro-3-pyridinecarboxamide 1-(3-{[tert-Butyl(dimethyl)silyl]oxy}propyl)-4-(2-fluoro-4-iodoanilino)-6-oxo-1,6-dihydro-3-pyridinecarboxylic acid was reacted with pentafluorophenyl trifluoroacetate in the presence of pyridine in THF as for example 4, step A, to afford the corresponding pentafluorophenyl ester which was reacted directly with conc. NH$_3$ solution in THF as for example 4, step B. All solvent was removed under reduced pressure and the resulting solid purified by chromatography on silica gel (50% EtOAc/hexanes as eluant) to afford 1-(3-{[tert-butyl(dimethyl)silyl]oxy}propyl)-4-(2-fluoro-4-iodoanilino)-6-oxo-1,6-dihydro-3-pyridinecarboxamide as a white solid (68%), used directly in the next step. $^1$H NMR [(CD$_3$)$_2$SO, 400 MHz] δ 10.36 (s, 1H), 8.24 (s, 1H), 7.92 (br s, 1H), 7.72 (dd, J=10.2, 1.8 Hz, 1H), 7.56 (br d, J=8.9 Hz, 1H), 7.46 (br s, 1H), 7.28 (t, J=8.5 Hz, 1H), 5.55 (s, 1H), 3.85 (t, J=7.1 Hz, 2H), 3.62 (t, J=6.1 Hz, 2H), 1.85 (pentet, J=6.6 Hz, 2H), 0.86 (s, 9H), 0.03 (s, 6H). HRMS (EI$^+$) calcd C$_{21}$H$_{29}$FIN$_3$O$_3$Si (M$^+$) 545.1007, found 545.1019.

Step C: Preparation of 4-(2-fluoro-4-iodoanilino)-1-(3-hydroxypropyl)-6-oxo-1,6-dihydro-3-pyridinecarboxamide 1-(3-{[tert-Butyl(dimethyl)silyl]oxy}propyl)-4-(2-fluoro-4-iodoanilino)-6-oxo-1,6-dihydro-3-pyridinecarboxamide was dissolved in EtOH and treated with 1 M HCl, as for example 22, step D, deprotecting the t-butyldimethylsilyl ether to give 4-(2-fluoro-4-iodoanilino)-1-(3-hydroxypropyl)-6-oxo-1,6-dihydro-3-pyridinecarboxamide as a white solid which was recrystallised from EtOAc/MeOH (86%), m.p. (EtOAc/MeOH) 220-223° C. $^1$H NMR [(CD$_3$)$_2$SO, 400 MHz] δ 10.40 (s, 1H), 8.29 (s, 1H), 7.91 (br s, 1H), 7.72 (dd, J=10.2, 1.8 Hz, 1H), 7.56 (br d, J=8.4 Hz, 1H), 7.46 (br s, 1H), 7.30 (t, J=8.5 Hz, 1H), 5.56 (s, 1H), 4.58 (t, J=5.1 Hz, 1H), 3.86 (t, J=7.2 Hz, 2H), 3.41 (q, J=5.7 Hz, 2H), 1.79 (pentet, J=6.6 Hz, 2H). Anal. Calcd for C$_{15}$H$_{15}$FIN$_3$O$_3$: C, 41.8; H, 3.5; N, 9.8. Found: C, 42.0; H, 3.4; N, 9.6.

EXAMPLE 33

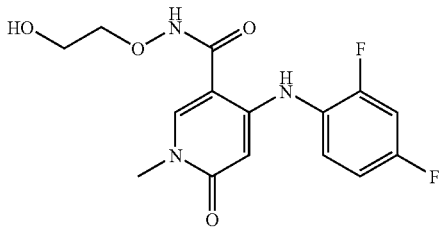

4-(2,4-Difluoroanilino)-N-(2-hydroxyethoxy)-1-methyl-6-oxo-1,6-dihydro-3-pyridinecarboxamide

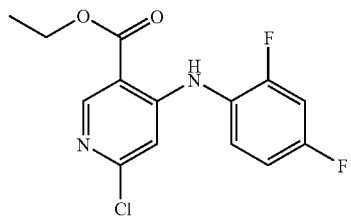

Step A: Preparation of ethyl 6-chloro-4-(2,4-difluoroanilino) nicotinate 2,4-Difluoroaniline (1.20 g, 9.3 mmol) and ethyl 4,6-dichloronicotinate (2.05 g, 9.3 mmol) were dissolved in a mixture of EtOH (40 ml) and conc. HCl (5 drops) and heated to reflux for 15 h. The solution was allowed to cool and H$_2$O (3 drops) was added to initialize precipitation. The flask was then sealed and placed in a freezer for 3 h. The solid was then isolated by filtration and washed with 10% Et$_2$O/Hexane, affording ethyl 6-chloro-4-(2,4-difluoroanilino) nicotinate (1.87 g, 64%); m.p. (EtOH/water) 107-109° C. $^1$H NMR [400 MHz, CDCl$_3$] δ 9.62 (br s, 1H), 8.79 (s, 1H), 7.35-7.29 (m, 1H), 7.02-6.95 (m, 2H), 6.58 (d, J=1.5 Hz, 1H), 4.42 (q, J=7.1 Hz, 2H), 1.43 (t, J=7.1 Hz, 3H). MS (FAB$^+$) 313 (50%).

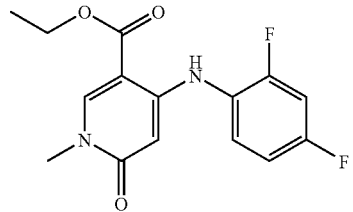

Step B: Preparation of ethyl 4-(2,4-difluoroanilino)-1-methyl-6-oxo-1,6-dihydro-3-pyridinecarboxylate Ethyl 6-chloro-4-(2,4-difluoroanilino)nicotinate (1.00 g, 3.2 mmol) was dissolved in CHCl$_3$ (35 ml) and cooled to 0° C. Me$_2$SO$_4$ (2.45 g, 19.5 mmol) was added dropwise over 5 min. The solution was allowed to warm to room temperature and then refluxed for 18 h. After cooling to room temperature, a mixture of triethylamine (9.9 ml), AcOH (6.6 ml) and EtOH (6.6 ml) was added. The reaction mixture was heated to reflux for a further 2 h then cooled and H$_2$O (50 ml) was added. After partitioning between water and EtOAc, the organic layer was further washed with water, brine, dried (Na$_2$SO$_4$) and concentrated under reduced pressure to give crude ethyl 4-(2,4-difluoroanilino)-1-methyl-6-oxo-1,6-dihydro-3-pyridinecarboxylate. Further purification by recrystallisation (EtOAc/Hexane) gave the desired product as a cream solid (0.55 g, 56%); m.p. (EtOAc/Hexane) 128-132° C. $^1$H NMR [400 MHz, CDCl$_3$] δ 9.15 (br s, 1H), 8.21 (s, 1H), 7.36-7.30 (m, 1H), 6.95-6.87 (m, 2H), 5.66 (s, 1H), 4.35 (q, J=7.1 Hz, 2H), 3.54 (s, 3H), 1.40 (t, J=7.1 Hz, 3H).

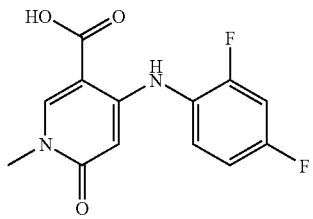

Step C: Preparation of 4-(2,4-difluoroanilino)-1-methyl-6-oxo-1,6-dihydro-3-pyridinecarboxylic acid Ethyl 4-(2,4-difluoroanilino)-1-methyl-6-oxo-1,6-dihydro-3-pyridinecarboxylate (0.50 g, 1.6 mmol) was dissolved in EtOH (30 ml) and 1M NaOH (30 ml). After stirring for 3.5 h at RT, the solution was concentrated under reduced pressure. 1M HCl was added, and the resultant precipitate isolated by filtration. The precipitate was washed with copious amounts of water then dried under vacuum to yield 4-(2,4-difluoroanilino)-1-methyl-6-oxo-1,6-dihydro-3-pyridinecarboxylic acid as a white solid (0.36 g, 80%); m.p. 253-255° C. $^1$H NMR [400 MHz, (CD$_3$)$_2$SO] δ 13.40 (v br s, 1H), 9.42 (br s, 1H), 8.50 (s, 1H), 7.51 (dt, J=9.0, 2.9 Hz, 1H), 7.42 (qd, J=9.0, 2.9 Hz, 1H), 7.18-7.13 (m, 1H), 5.25 (d, J=1.3 Hz, 1H), 3.40 (s, 3H). MS (FAB$^+$) 281 (35%).

Step D: Preparation of 4-(2,4-difluoroanilino)-N-(2-hydroxyethoxy)-1-methyl-6-oxo-1,6-dihydro-3-pyridinecarboxamide 2-(Aminooxy)ethanol (0.05 g, 0.6 mmol) in MeOH (1 ml) was added to 4-(2,4-difluoroanilino)-1-methyl-6-oxo-1,6-dihydro-3-pyridinecarboxylic acid (0.15 g, 0.5 mmol) in MeOH (20 ml). THF was added dropwise until the reagents dissolved. The solution was stirred at RT for 30 min, after which DMT-MM (0.18 g, 0.6 mmol) was added. After stirring at RT for 60 h, the reaction had not gone to completion. Further 2-(aminooxy)ethanol (0.05 g, 0.6 mmol) and DMT-MM (0.18 g, 0.6 mmol) were added and the reaction mixture stirred for a further 2 h at RT. The solvent was then removed under reduced pressure and the residue dissolved in EtOAc. After washing with water ×2, sat. NaHCO$_3$ and brine, the organic layer was dried (Na$_2$SO$_4$), concentrated and further purified by flash chromatography on silica gel (EtOAc followed by 10% MeOH/CH$_2$Cl$_2$) to give 4-(2,4-difluoroanilino)-N-(2-hydroxyethoxy)-1-methyl-6-oxo-1,6-dihydro-3-pyridinecarboxamide (0.07 g, 39%) as a white solid; m.p. (EtOAc/Hexane) 232-238° C. $^1$H NMR [400 MHz, (CD$_3$)$_2$SO] δ 11.62 (br s, 1H), 9.21 (br s, 1H), 8.11 (s, 1H), 7.51-7.38 (m, 2H), 7.17-7.11 (m, 1H), 5.30 (s, 1H), 4.76 (br s, 1H), 3.92 (t, J=4.8 Hz, 2H), 3.62 (t, J=4.8 Hz, 2H), 3.34 (s, 3H). LCMS (ACPI$^+$) 340 (100%). Anal. Calcd for C$_{15}$H$_{15}$F$_2$N$_3$O$_4$.0.25 H$_2$O: C, 52.4; H, 4.5; N, 12.2. Found C, 52.6; H, 4.5; N, 12.1

EXAMPLE 34

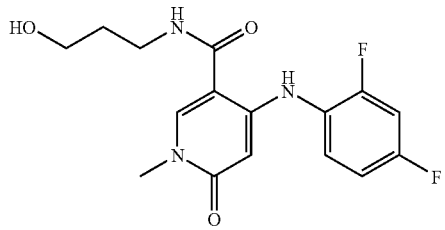

4-(2,4-Difluoroanilino)-N-(3-hydroxypropyl)-1-methyl-6-oxo-1,6-dihydro-3-pyridinecarboxamide 4-(2,4-Difluoroanilino)-1-methyl-6-oxo-1,6-dihydro-3-pyridinecarboxylic acid (0.15 g, 0.5 mmol) was dissolved in a mixture of anhydrous THF (20 ml) and anhydrous DMF (2 ml). CDI (0.18 g, 1.1 mmol) was added and the solution stirred at RT for 2 h. 3-Amino-1-propanol (0.16 g, 2.2 mmol) was then added and the solution stirred for a further 15 h. The solvent was removed under reduced pressure and the residue partitioned between 2% MeOH/EtOAc and water. The organic fraction was washed with water ×2, NaHCO$_3$, brine, dried (Na$_2$SO$_4$) and concentrated to give crude 4-(2,4-difluoroanilino)-N-(3-hydroxypropyl)-1-methyl-6-oxo-1,6-dihydro-3-pyridinecarboxamide. Further purification by flash chromatography on silica gel (5% MeOH/CH$_2$Cl$_2$) afforded 4-(2,4-difluoroanilino)-N-(3-hydroxypropyl)-1-methyl-6-oxo-1,6-dihydro-3-pyridinecarboxamide (0.12 g, 68%) as a cream solid; m.p. (EtOAc/Hexane) 129-132° C. $^1$H NMR [400 MHz, (CD$_3$)$_2$SO] δ 9.84 (br s, 1H), 8.36 (t, J=5.4 Hz, 1H), 8.22 (s, 1H), 7.51-7.37 (m, 2H), 7.16-7.10 (m, 1H), 5.32 (d, J=1.1 Hz, 1H), 4.47 (t, J=4.9 Hz, 1H), 3.47 (dd, J=11.5, 6.2 Hz, 2H), 3.35 (s, 3H), 3.27 (dd, J=12.7, 6.8 Hz, 2H), 1.67 (p, J=6.7 Hz, 2H). LCMS (ACPI$^-$) 336 (100%). Anal. Calcd for C$_{16}$H$_{17}$F$_2$N$_3$O$_3$.0.25 H$_2$O: C, 56.2; H, 5.2; N, 12.3. Found C, 56.4; H, 5.3; N, 12.5.

EXAMPLE 35

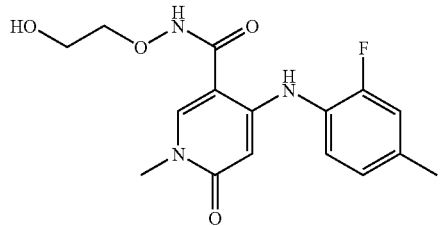

4-(2-Fluoro-4-methylanilino)-N-(2-hydroxyethoxy)-1-methyl-6-oxo-1,6-dihydro-3-pyridinecarboxamide

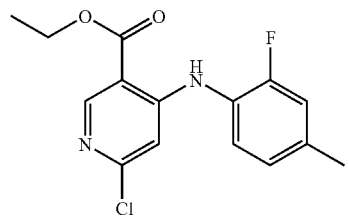

Step A: Preparation of ethyl 6-chloro-4-(2-fluoro-4-methylanilino)nicotinate

2-Fluoro-4-methylaniline and ethyl 4,6-dichloronicotinate were reacted in a mixture of EtOH and conc. HCl as for example 33, step A. The resultant solid was isolated by filtration and washed with 10% Et$_2$O/Hexane, to give ethyl 6-chloro-4-(2-fluoro-4-methylanilino)nicotinate (44%); m.p. (EtOH/water) 107-109° C. $^1$H NMR [400 MHz, CDCl$_3$] δ 9.63 (br s, 1H), 8.77 (s, 1H), 7.20 (t, J=8.2 Hz, 1H), 7.05-6.99 (m, 2H), 6.65 (d, J=1.6 Hz, 1H), 4.41 (q, J=7.1 Hz, 2H), 1.43 (t, J=7.1 Hz, 3H). MS (FAB$^+$) 309 (40%).

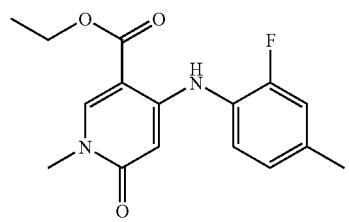

Step B: Preparation of ethyl 4-(2-fluoro-4-methylanilino)-1-methyl-6-oxo-1,6-dihydro-3-pyridinecarboxylate Ethyl 6-chloro-4-(2-fluoro-4-methylanilino)nicotinate) was dissolved in CHCl$_3$ and reacted with Me$_2$SO$_4$, followed by triethylamine, AcOH and EtOH as described for example 33, step B. Purification by recrystallisation (EtOAc/Hexane) afforded ethyl 4-(2-fluoro-4-methylanilino)-1-methyl-6-oxo-1,6-dihydro-3-pyridinecarboxylate (84%); m.p. (EtOAc/Hexane) 148-150° C. $^1$H NMR [400 MHz, CDCl$_3$] δ 9.17 (br s, 1H), 8.20 (s, 1H), 7.27-7.21 (m, 1H), 6.99-6.92 (m, 2H), 5.76 (s, 1H), 4.35 (q, J=7.1 Hz, 2H), 3.53 (s, 3H), 2.35 (s, 3H), 1.39 (t, J=7.1 Hz, 3H). LCMS (ACPI$^-$) 303 (100%). Anal. Calcd for C$_{16}$H$_{17}$FN$_2$O$_3$: C, 63.2; H, 5.6; N, 9.2. Found C, 63.1; H, 5.7; N, 9.2.

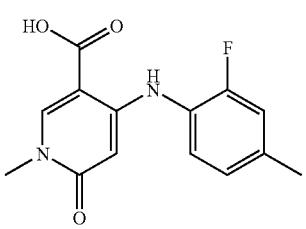

Step C: Preparation of 4-(2-fluoro-4-methylanilino)-1-methyl-6-oxo-1,6-dihydro-3-pyridinecarboxylic acid Ethyl 4-(2-fluoro-4-methylanilino)-1-methyl-6-oxo-1,6-dihydro-3-pyridinecarboxylate was dissolved in EtOH and treated with 1M NaOH as for example 33, step C. The precipitate which formed on addition of 1M HCl was washed with copious amounts of water then dried under vacuum to yield 4-(2-fluoro-4-methylanilino)-1-methyl-6-oxo-1,6-dihydro-3-pyridinecarboxylic acid as a white solid (91%). $^1$H NMR [400 MHz, (CD$_3$)$_2$SO] δ 13.20 (v br s, 1H), 9.47 (br s, 1H), 8.49 (s, 1H), 7.34 (t, J=8.3 Hz, 1H), 7.18 (d, J=11.7 Hz, 1H), 7.07 (d, J=7.8 Hz, 1H), 5.33 (d, J=1.1 Hz, 1H), 3.39 (s, 3H), 2.33 (s, 3H).

Step D: Preparation of 4-(2-fluoro-4-methylanilino)-N-(2-hydroxyethoxy)-1-methyl-6-oxo-1,6-dihydro-3-pyridinecarboxamide 2-(Aminooxy)ethanol, 4-(2-fluoro-4-methylanilino)-1-methyl-6-oxo-1,6-dihydro-3-pyridinecarboxylic acid and DMT-MM were reacted in MeOH as outlined in example 33, step D. Further purification by flash chromatography on silica gel (EtOAc followed by 10% MeOH/CH$_2$Cl$_2$) gave 4-(2-fluoro-4-methylanilino)-N-(2-hydroxyethoxy)-1-methyl-6-oxo-1,6-dihydro-3-pyridinecarboxamide (61%) as a cream solid; m.p. (EtOAc/Hexane) 110-115° C. $^1$H NMR [400 MHz, (CD$_3$)$_2$SO] δ 11.62 (br s, 1H), 9.21 (br s, 1H), 8.11 (s, 1H), 7.31 (t, J=8.3 Hz, 1H), 7.17 (d, J=11.8 Hz, 1H), 7.06 (d, J=8.3 Hz, 1H), 5.38 (s, 1H), 4.75 (t, J=5.3 Hz, 1H), 3.91 (t, J=4.9 Hz, 2H), 3.62 (q, J=4.9 Hz, 2H), 3.35 (s, 3 H, obscured), 2.32 (s, 3H). LCMS (ACPI$^-$) 334 (50%). Anal. Calcd for C$_{16}$H$_{18}$FN$_3$O$_4$.0.25 H$_2$O: C, 56.6; H, 5.5; N, 12.4. Found C, 56.5; H, 5.5; N, 12.1.

EXAMPLE 36

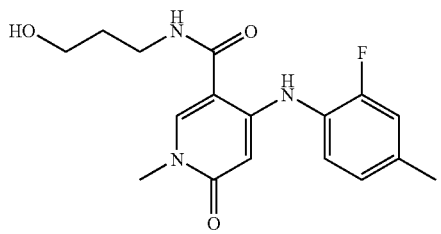

4-(2-Fluoro-4-methylanilino)-N-(3-hydroxypropyl)-1-methyl-6-oxo-1,6-dihydro-3-pyridinecarboxamide 4-(2-Fluoro-4-methylanilino)-1-methyl-6-oxo-1,6-dihydro-3-pyridinecarboxylic acid and CDI were dissolved in a mixture of anhydrous THF and anhydrous DMF and treated with 3-amino-1-propanol as for example 34. After workup, the residue was further purified by flash chromatography on silica gel (5% MeOH/CH$_2$Cl$_2$—10% MeOH/CH$_2$Cl$_2$ gradient elution) yielding 4-(2-fluoro-4-methylanilino)-N-(3-hydroxypropyl)-1-methyl-6-oxo-1,6-dihydro-3-pyridinecarboxamide (47%) as a pale cream solid; m.p. (EtOAc/Hexane) 142-145° C. $^1$H NMR [400 MHz, (CD$_3$)$_2$SO] δ 9.86 (br s, 1H), 8.36 (t, J=5.4 Hz, 1H), 8.21 (s, 1H), 7.30 (t, J=8.4 Hz, 1H), 7.16 (d, J=11.8 Hz, 1H), 7.05 (d, J=7.7 Hz, 1H), 5.40 (s, 1H), 4.48 (t, J=5.1 Hz, 1H), 3.47 (dd, J=11.5, 6.2 Hz, 2H), 3.35 (s, 3H), 3.27 (dd, J=12.8, 6.8 Hz, 2H), 2.32 (s, 3H), 1.67 (p, J=6.7 Hz, 2H). LCMS (ACPI$^-$) 332 (100%). Anal. Calcd for C$_{17}$H$_{20}$FN$_3$O$_3$: C, 61.3; H, 6.1; N, 12.6. Found C, 61.0; H, 6.3; N, 12.7.

EXAMPLE 37

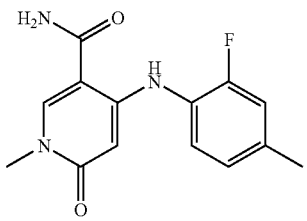

4-(2-Fluoro-4-methylanilino)-1-methyl-6-oxo-1,6-dihydro-3-pyridinecarboxamide

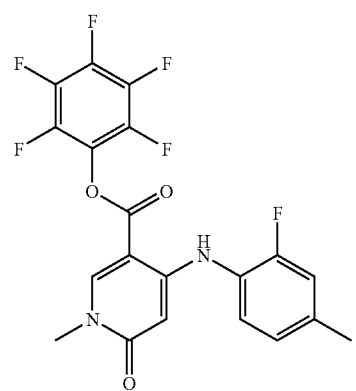

Step A: Preparation of 2,3,4,5,6-pentafluorophenyl 4-(2-fluoro-4-methylanilino)-1-methyl-6-oxo-1,6-dihydro-3-pyridinecarboxylate 4-(2-Fluoro-4-methylanilino)-1-methyl-6-oxo-1,6-dihydro-3-pyridinecarboxylic acid and pentafluorophenyl trifluoroacetate were reacted in the presence of pyridine in THF as for example 4, step A. The crude residue was purified by flash chromatography on silica gel (60% EtOAc/Hexane) to give 2,3,4,5,6-pentafluorophenyl 4-(2-fluoro-4-methylanilino)-1-methyl-6-oxo-1,6-dihydro-3-pyridinecarboxylate (90%). $^1$H NMR [400 MHz, (CD$_3$)$_2$SO] δ 9.02 (s, 1H), 8.60 (s, 1H), 7.33 (t, J=8.3 Hz, 1H), 7.20 (dd, J=11.6, 1.1 Hz, 1H), 7.09 (d, J=8.1 Hz, 1H), 5.24 (d, J=1.6 Hz, 1H), 3.48 (s, 3H), 2.34 (s, 3H).

Step B: Preparation of 4-(2-fluoro-4-methylanilino)-1-methyl-6-oxo-1,6-dihydro-3-pyridinecarboxamide Conc. NH$_3$ solution (0.5 ml) was added to 2,3,4,5,6-pentafluorophenyl 4-(2-fluoro-4-methylanilino)-1-methyl-6-oxo-1,6-dihydro-3-pyridinecarboxylate (0.33 g, 0.6 mmol) in THF (10 ml) and the solution stirred at RT for 2 h. The solvent was removed under reduced pressure and the residue dissolved in 5% EtOAc/MeOH. The organic phase was washed with water, brine, dried (Na$_2$SO$_4$) and concentrated to give crude 4-(2-fluoro-4-methylanilino)-1-methyl-6-oxo-1,6-dihydro-3-pyridinearboxamide which was then recrystallised (EtOAc/Hexane) (0.11 g, 84%); m.p. (EtOAc/Hexane) 285-288° C. $^1$H NMR [400 MHz, (CD$_3$)$_2$SO] δ 10.14 (s, 1H), 8.32 (s, 1H), 7.86 (br s, 1H), 7.43 (br s, 1H), 7.31 (t, J=8.4 Hz), 1H), 7.16 (dd, J=11.8, 1.1 Hz, 1H), 7.05 (d, J=8.2 Hz, 1H), 5.38 (d, J=1.1 Hz, 1H), 3.34 (s, 3H), 2.32 (s, 3H). LCMS (ACPI$^-$) 274 (100%). Anal. Calcd for C$_{14}$H$_{14}$FN$_3$O$_2$: C, 61.1; H, 5.1; N, 15.3. Found C, 61.0; H, 5.2; N, 15.4.

EXAMPLE 38

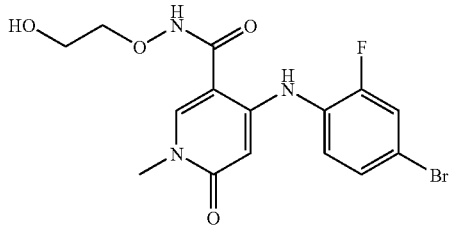

4-(4-Bromo-2-fluoroanilino)-N-(2-hydroxyethoxy)-1-methyl-6-oxo-1,6-dihydro-3-pyridinecarboxamide

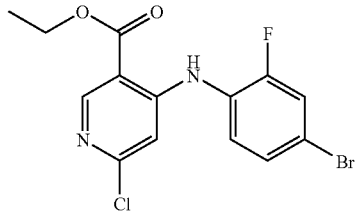

Step A: Preparation of ethyl 4-(4-bromo-2-fluoroanilino)-6-chloronicotinate

4-Bromo-2-fluoroaniline and ethyl 4,6-dichloronicotinate were reacted in a mixture of EtOH and conc. HCl as for example 33, step A. The resultant solid was isolated by filtration and washed with 10% Et$_2$O/Hexane, to give ethyl 4-(4-bromo-2-fluoroanilino)-6-chloronicotinate (58%); m.p. (EtOH/water) 150-152° C. $^1$H NMR [400 MHz, CDCl$_3$] δ 9.74 (br s, 1H), 8.81 (s, 1H), 7.41 (dd, J=9.6, 2.2 Hz, 1H), 7.38-7.35 (m, 1H), 7.25 (t, J=8.3 Hz, 1H), 6.71 (d, J=1.5 Hz, 1H), 4.42 (q, J=7.1 Hz, 2H), 1.43 (t, J=7.1 Hz, 3H). MS (FAB$^+$) 375 (16%).

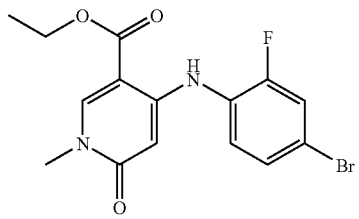

Step B: Preparation of ethyl 4-(4-bromo-2-fluoroanilino)-1-methyl-6-oxo-1,6-dihydro-3-pyridinecarboxylate Ethyl 4-(4-bromo-2-fluoroanilino)-6-chloronicotinate was dissolved in CHCl$_3$ and reacted with Me$_2$SO$_4$, followed by triethylamine, AcOH and EtOH as described for example 33, step B. Purification by recrystallisation (EtOAc/Hexane) gave ethyl 4-(4-bromo-2-fluoroanilino)-1-methyl-6-oxo-1,6-dihydro-3-pyridinecarboxylate (77%); m.p. (EtOAc/Hexane) 159-162° C. $^1$H NMR [400 MHz, CDCl$_3$] δ 9.34 (br s, 1H), 8.22 (s, 1H), 7.36-7.25 (m, 3H), 5.85 (s, 1H), 4.35 (q, J=7.1 Hz, 2H), 3.54 (s, 3H), 1.39 (t, J=7.1 Hz, 3H). LCMS (APCI$^-$) 369 (100%), 367 (100%). Anal. Calcd for C$_{15}$H$_{14}$BrFN$_2$O$_3$: C, 48.8; H, 3.8; N, 7.6. Found C, 49.1; H, 3.8; N, 7.4.

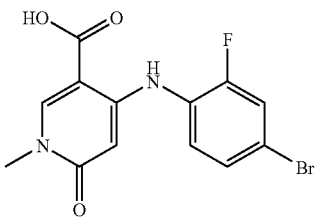

Step C: Preparation of 4-(4-bromo-2-fluoroanilino)-1-methyl-6-oxo-1,6-dihydro-3-pyridinecarboxylic acid Ethyl 4-(4-bromo-2-fluoroanilino)-1-methyl-6-oxo-1,6-dihydro-3-pyridinecarboxylate was dissolved in EtOH and treated with 1M NaOH as for example 33, step C. The precipitate which formed on addition of 1M HCl was washed with copious amounts of water then dried under vacuum to afford 4-(4-bromo-2-fluoroanilino)-1-methyl-6-oxo-1,6-dihydro-3-pyridinecarboxylic acid as a white solid (89%). $^1$H NMR [400 MHz, (CD$_3$)$_2$SO] δ 13.30 (v br s, 1H), 9.65 (br s, 1H), 8.52 (s, 1H), 7.69 (dd, J=10.3, 1.6 Hz, 1H), 7.51-7.43 (m, 2H), 5.47 (d, J=1.2 Hz, 1H), 3.41 (s, 3H).

Step D: Preparation of 4-(4-bromo-2-fluoroanilino)-N-(2-hydroxyethoxy)-1-methyl-6-oxo-1,6-dihydro-3-pyridinecarboxamide 2-(Aminooxy)ethanol, 4-(4-bromo-2-fluoroanilino)-1-methyl-6-oxo-1,6-dihydro-3-pyridinecarboxylic acid and DMT-MM were reacted in MeOH as outlined in example 33, step D. Further purification by flash chromatography on silica gel (EtOAc followed by 10% MeOH/CH$_2$Cl$_2$) gave 4-(4-bromo-2-fluoroanilino)-N-(2-hydroxyethoxy)-1-methyl-6-oxo-1,6-dihydro-3-pyridinecarboxamide (38%); m.p. (EtOAc/Hexane) 124-128° C. $^1$H NMR [400 MHz, (CD$_3$)$_2$SO] δ 11.64 (br s, 1H), 9.50 (br s, 1H), 8.13 (s, 1H), 7.69-7.65 (m, 1H), 7.47-7.41 (m, 2H), 5.53 (d, J=0.7 Hz, 1H), 4.78 (s, 1H), 3.91 (t, J=5.0 Hz, 2H), 3.61 (t, J=5.0 Hz, 2H), 3.36 (s, 3H). LCMS (ACPI$^-$) 400 (80%), 398 (100%). Anal. Calcd for C$_{15}$H$_{15}$BrFN$_3$O$_4$·0.25 H$_2$O: C, 44.5; H, 3.9; N, 10.4. Found C, 44.3; H, 3.5; N, 10.2.

EXAMPLE 39

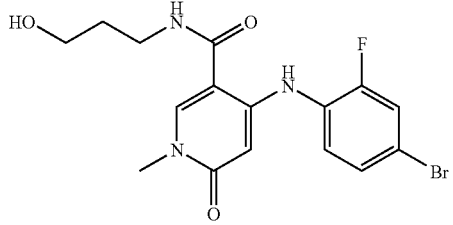

4-(4-Bromo-2-fluoroanilino)-N-(3-hydroxypropyl)-1-methyl-6-oxo-1,6-dihydro-3-pyridinecarboxamide 4-(4-Bromo-2-fluoroanilino)-1-methyl-6-oxo-1,6-dihydro-3-pyridinecarboxylic acid and CDI were dissolved in a mixture of anhydrous THF and anhydrous DMF and treated with 3-amino-1-propanol as for example 34. After workup, the residue was further purified by flash chromatography on silica gel (5% MeOH/CH$_2$Cl$_2$) to give 4-(4-bromo-2-fluoroanilino)-N-(3-hydroxypropyl)-1-methyl-6-oxo-1,6-dihydro-3-pyridinecarboxamide (71%) as a cream solid; m.p. (EtOAc/Hexane) 167-170° C. $^1$H NMR [400 MHz, (CD$_3$)$_2$SO] δ 10.10 (br s, 1H), 8.40 (t, J=5.3 Hz, 1H), 8.24 (s, 1H), 7.69-7.64 (m, 1H), 7.48-7.40 (m, 2H), 5.56 (s, 1H), 4.48 (t, J=5.1 Hz, 1H), 3.47 (dd, J=11.5, 6.2 Hz, 2H), 3.37 (s, 3H), 3.27 (dd, J=12.7, 6.9 Hz, 2H), 1.67 (p, J=6.7 Hz, 2H). LCMS (ACPI$^-$) 398 (85%), 396 (100%). Anal. Calcd for C$_{16}$H$_{17}$BrFN$_3$O$_3$: C, 48.3; H, 4.3; N, 10.6. Found C, 48.2; H, 4.2; N, 10.5.

EXAMPLE 40

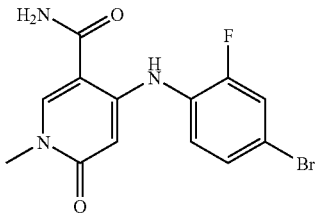

4-(4-Bromo-2-fluoroanilino)-1-methyl-6-oxo-1,6-dihydro-3-pyridinecarboxamide

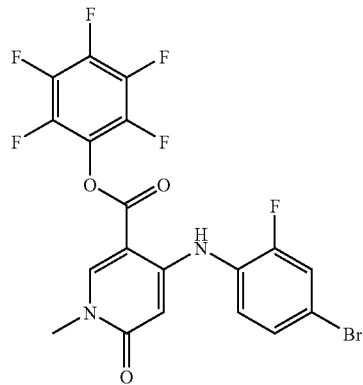

Step A: Preparation of 2,3,4,5,6-pentafluorophenyl 4-(4-bromo-2-fluoroanilino)-1-methyl-6-oxo-1,6-dihydro-3-pyridinecarboxylate 4-(4-Bromo-2-fluoroanilino)-1-methyl-6-oxo-1,6-dihydro-3-pyridinecarboxylic acid and pentafluorophenyl trifluoroacetate were reacted in the presence of pyridine in THF as for example 4, step A. The crude residue was purified by flash chromatography on silica gel (60% EtOAc/Hexane) to give 2,3,4,5,6-pentafluorophenyl 4-(4-bromo-2-fluoroanilino)-1-methyl-6-oxo-1,6-dihydro-3-pyridinecarboxylate (97%). $^1$H NMR [400 MHz, (CD$_3$)$_2$SO] δ 9.03 (s, 1H), 8.70 (s, 1H), 7.71 (dd, J=10.6, 2.0 Hz, 1H), 7.49 (dd, J=8.5, 2.0 Hz, 1H), 7.46 (t, J=8.7 Hz, 1H), 5.34 (d, J=1.6 Hz, 1H), 3.49 (s, 3H).

Step B: Preparation of 4-(4-bromo-2-fluoroanilino)-1-methyl-6-oxo-1,6-dihydro-3-pyridinecarboxamide 2,3,4,5,6-Pentafluorophenyl 4-(4-bromo-2-fluoroanilino)-1-methyl-6-oxo-1,6-dihydro-3-pyridinecarboxylate in THF was reacted with conc. NH$_3$ solution as for example 37, step B. Recrystallisation (EtOAc/Hexane) yielded 4-(4-bromo-2-fluoroanilino)-1-methyl-6-oxo-1,6-dihydro-3-pyridinecarboxamide (100%); m.p. (EtOAc/Hexane) 282-284° C. $^1$H NMR [400 MHz, (CD$_3$)$_2$SO] δ 10.39 (s, 1H), 8.35 (s, 1H), 7.89 (br s, 1H), 7.66 (dd, J=10.4, 1.7 Hz, 1H), 7.51-7.44 (br m, 2H), 7.42 (dd, J=8.5, 1.9 Hz, 1H), 5.55 (s, 1H), 3.38 (s, 3H). LCMS (ACPI$^-$) 340 (100%), 338 (90%). Anal. Calcd for C$_{13}$H$_{11}$BrFN$_3$O$_2$: C, 45.9; H, 3.3; N, 12.4. Found C, 46.1; H, 3.2; N, 12.6.

EXAMPLE 41

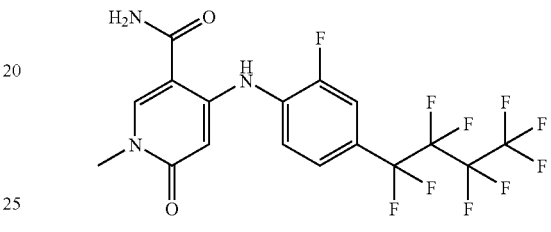

4-[2-Fluoro-4-(1,1,2,2,3,3,4,4,4-nonafluorobutyl)anilino]-1-methyl-6-oxo-1,6-dihydro-3-pyridinecarboxamide

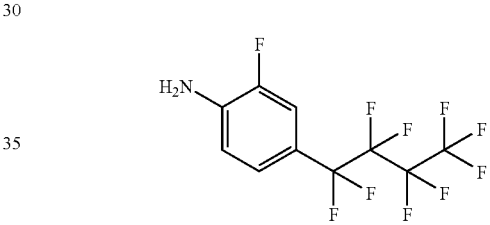

Step A: Preparation of 2-fluoro-4-(1,1,2,2,3,3,4,4,4-nonafluorobutyl)aniline

A dispersion of 1,1,1,2,2,3,3,4,4-nonafluoro-4-iodobutane (3.50 9, 10.1 mmol), 2-fluoro-4-iodoaniline (2.00 g, 8.4 mmol) and copper bronze (1.93 g, 30.4 mmol) in DMSO (10 ml) was stirred at 120° C. for 15 h. Copper(I) iodide was removed by filtration through Celite®. Et$_2$O (100 ml) was used to wash the Celite® plug. Water (100 ml) was then added to the filtrate and the mixture stirred at RT for 5 min. The organic layer was separated and washed 5× with water to remove DMSO, dried (Na$_2$SO$_4$) and concentrated. Flash chromatography on silica gel (10% EtOAc/Hexane) afforded 2-fluoro-4-(1,1,2,2,3,3,4,4,4-nonafluorobutyl)aniline (1.69 g, 61%). $^1$H NMR [300 MHz, CDCl$_3$] δ 7.25-7.14 (m, 2H), 6.86-6.74 (m, 1H), 4.07 (br s, 1H). LCMS (ACPI$^-$) 328 (100%).

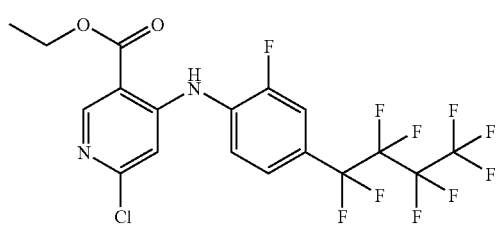

Step B: Preparation of ethyl 6-chloro-4-[2-fluoro-4-(1,1,2,2,3,3,4,4,4-nonafluorobutyl)-anilino]nicotinate 2-Fluoro-4-(1,1,2,2,3,3,4,4,4-nonafluorobutyl) aniline and ethyl 4,6-dichloronicotinate were reacted in a mixture of EtOH and conc. HCl for 36 h as for example 33, step A. The resultant solid was purified by flash chromatography on silica gel (Hexane—10% EtOAc/Hexane gradient elution) to give ethyl 6-chloro-4-[2-fluoro-4-(1,1,2,2,3,3,4,4,4-nonafluorobutyl)anilino]nicotinate (30%). $^1$H NMR [400 MHz, CDCl$_3$] δ 10.11 (br s, 1H), 8.86 (s, 1H), 7.57 (t, J=8.0 Hz, 1H), 7.46 (d, J=9.7 Hz, 2H), 6.98 (d, J=0.7 Hz, 1H), 4.44 (q, J=7.1 Hz, 2H), 1.44 (t, J=7.1 Hz, 3H).

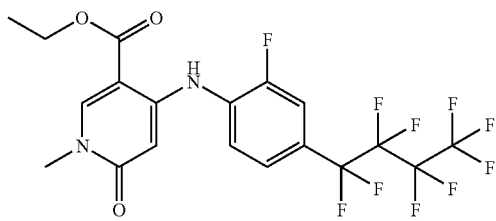

Step C: Preparation of ethyl 4-[2-fluoro-4-(1,1,2,2,3,3,4,4,4-nonafluorobutyl)anilino]-1-methyl-6-oxo-1,6-dihydro-3-pyridinecarboxylate Ethyl 6-chloro-4-[2-fluoro-4-(1,1,2,2,3,3,4,4,4-nonafluorobutyl)anilino]nicotinate was dissolved in CHCl$_3$ and reacted with Me$_2$SO$_4$, followed by triethylamine, AcOH and EtOH as described for example 33, step B. Purification by recrystallisation (EtOAc/Hexane) gave ethyl 4-[2-fluoro-4-(1,1,2,2,3,3,4,4,4-nonafluorobutyl)anilino]-1-methyl-6-oxo-1,6-dihydro-3-pyridinecarboxylate (47%). $^1$H NMR [400 MHz, (CD$_3$)$_2$SO] δ 9.50 (s, 1H), 8.35 (s, 1H), 7.58 (t, J=8.3 Hz, 1H), 7.52 (dd, J=10.9, 1.8 Hz, 1H), 7.34 (d, J=8.1 Hz, 1H), 5.59 (s, 1H), 4.08 (q, J=7.1 Hz, 2H), 3.22 (s, 3H), 1.10 (t, J=7.1 Hz, 3H).

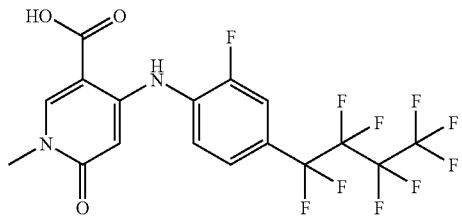

Step D: Preparation of 4-[2-fluoro-4-(1,1,2,2,3,3,4,4,4-nonafluorobutyl)anilino]-1-methyl-6-oxo-1,6-dihydro-3-pyridinecarboxylic acid Ethyl 4-[2-fluoro-4-(1,1,2,2,3,3,4,4,4-nonafluorobutyl)anilino]-1-methyl-6-oxo-1,6-dihydro-3-pyridinecarboxylate was dissolved in EtOH and treated with 1M NaOH as described for example 33, step C. The precipitate which formed on addition of 1M HCl was washed with copious amounts of water then dried under vacuum to afford 4-[2-fluoro-4-(1,1,2,2,3,3,4,4,4-nonafluorobutyl)anilino]-1-methyl-6-oxo-1,6-dihydro-3-pyridinecarboxylic acid (75%). $^1$H NMR [400 MHz, (CD$_3$)$_2$SO] δ 13.20 (v br s, 1H), 10.21 (br s, 1H), 8.56 (s, 1H), 7.83 (t, J=8.3 Hz, 1H), 7.74 (d, J=10.4 Hz, 1H), 7.57 (d, J=8.2 Hz, 1H), 5.86 (s, 1H), 3.44 (s, 3H).

Step E: Preparation of 4-[2-fluoro-4-(1,1,2,2,3,3,4,4,4-nonafluorobutyl)anilino]-1-methyl-6-oxo-1,6-dihydro-3-pyridinecarboxamide 4-[2-fluoro-4-(1,1,2,2,3,3,4,4,4-nonafluorobutyl)anilino]-1-methyl-6-oxo-1,6-dihydro-3-pyridinecarboxylic acid and pentafluorophenyl trifluoroacetate were reacted in the presence of pyridine in THF as described for example 4, step A.

Without further purification, the crude 2,3,4,5,6-pentafluorophenyl 4-[2-fluoro-4-(1,1,2,2,3,3,4,4,4-nonafluorobutyl)anilino]-1-methyl-6-oxo-1,6-dihydro-3-pyridinecarboxylate was then dissolved in THF and reacted with conc. NH$_3$ solution as for example 37, step B. Recrystallisation (EtOAc/Hexane) yielded 4-[2-fluoro-4-(1,1,2,2,3,3,4,4,4-nonafluorobutyl)anilino]-1-methyl-6-oxo-1,6-dihydro-3-pyridinecarboxamide (65%); m.p. (EtOAc/Hexane) 112-118° C. (glue-liquid). $^1$H NMR [400 MHz, (CD$_3$)$_2$SO] δ 10.92 (s, 1H), 8.40 (s, 1H), 7.93 (br s, 1H), 7.79 (t, J=8.3 Hz, 1H), 7.70 (dd, J=11.2, 1.7 Hz, 1H), 7.53 (d, J=7.8 Hz, 2H), 5.92 (s, 1H), 3.40 (s, 3H). HRMS (FAB$^+$) calcd for C$_{17}$H$_{12}$F$_{10}$N$_3$O$_2$ 480.0770 (M$^+$), found 480.0762.

EXAMPLE 42

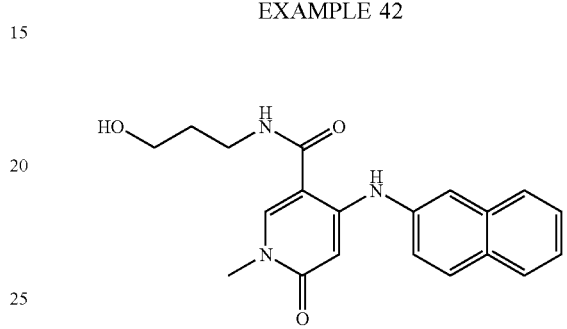

N-(3-Hydroxypropyl)-1-methyl-4-(2-naphthylamino)-6-oxo-1,6-dihydro-3-pyridinecarboxamide

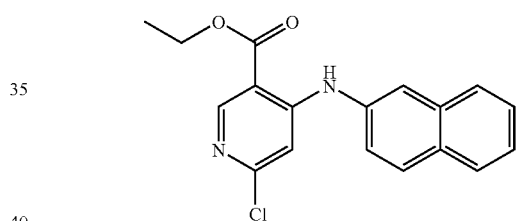

Step A: Preparation of ethyl 6-chloro-4-(2-naphthylamino)nicotinate

2-Naphthylamine and ethyl 4,6-dichloronicotinate were reacted in a mixture of EtOH and conc. HCl as for example 33, step A. The resultant solid was isolated by filtration and washed with 10% Et$_2$O/Hexane, yielding ethyl 6-chloro-4-(2-naphthylamino)nicotinate (68%). $^1$H NMR [400 MHz, (CD$_3$)$_2$SO] δ 9.91 (br s, 1H), 8.71 (s, 1H), 8.02 (d, J=8.7 Hz, 1H), 7.97-7.88 (m, 3H), 7.59-7.48 (m, 3H), 6.91 (s, 1H), 4.39 (q, J=7.1 Hz, 2H), 1.37 (t, J=7.1 Hz, 3H).

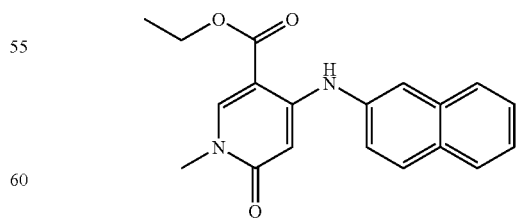

Step B: Preparation of ethyl 1-methyl-4-(2-naphthylamino)-6-oxo-1,6-dihydro-3-pyridinecarboxylate Ethyl 6-chloro-4-(2-naphthylamino)nicotinate was dissolved in CHCl$_3$ and reacted with Me$_2$SO$_4$, followed by triethylamine, AcOH and EtOH as described for example 33, step B. Purification by recrystallisation (EtOAc/Hexane) afforded ethyl 1-methyl-4-(2-naphthylamino)-6-oxo-1,6-dihydro-3-pyridinecarboxylate as a white solid (57%); m.p. (EtOAc/Hexane) 160-163° C. $^1$H NMR [400 MHz, (CD$_3$)$_2$SO] δ 9.55 (s, 1H), 8.57 (s, 1H), 7.97 (d, J=8.8 Hz, 1H), 7.91 (dd, J=7.7, 4.7 Hz, 2H), 7.81 (d, J=1.8 Hz, 1H), 7.55-7.43 (m, 3H), 5.79 (s, 1H), 4.32 (q, J=7.1 Hz, 2H), 3.43 (s, 3H), 1.35 (t, J=7.1 Hz, 3H). Anal. Calcd for C$_{19}$H$_{18}$N$_2$O$_3$: C, 70.8; H, 5.6; N, 8.7. Found C, 70.8; H, 5.5; N, 8.7.

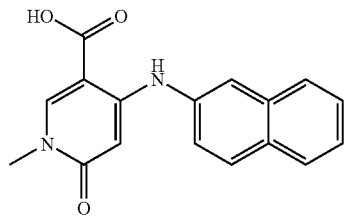

Step C: Preparation of 1-methyl-4-(2-naphthylamino)-6-oxo-1,6-dihydro-3-pyridinecarboxylic acid Ethyl 1-methyl-4-(2-naphthylamino)-6-oxo-1,6-dihydro-3-pyridinecarboxylate was dissolved in EtOH and treated with 1M NaOH for 15 h as for example 33, step C. The precipitate which formed on addition of 1M HCl was washed with copious amounts of water then dried under vacuum to give 1-methyl-4-(2-naphthylamino)-6-oxo-1,6-dihydro-3-pyridinecarboxylic acid (88%). $^1$H NMR [400 MHz, (CD$_3$)$_2$SO] δ 13.27 (v br s, 1H), 9.95 (br s, 1H), 8.53 (s, 1H), 7.96 (d, J=8.8 Hz, 1H), 7.91 (d, J=8.8 Hz, 2H), 7.80 (d, J=1.9 Hz, 1H), 7.54-7.42 (m, 3H), 5.81 (s, 1H), 3.42 (s, 3H).

Step D: Preparation of N-(3-hydroxypropyl)-1-methyl-4-(2-naphthylamino)-6-oxo-1,6-dihydro-3-pyridinecarboxamide 1-Methyl-4-(2-naphthylamino)-6-oxo-1,6-dihydro-3-pyridinecarboxylic acid and CDI were dissolved in a mixture of anhydrous THF and anhydrous DMF and treated with 3-amino-1-propanol as for example 34. After workup, the residue was further purified by flash chromatography on silica gel (5% MeOH/CH$_2$Cl$_2$—10% MeOH/CH$_2$Cl$_2$ gradient elution) to give 4-(4-bromo-2-fluoroanilino)-N-(3-hydroxypropyl)-1-methyl-6-oxo-1,6-dihydro-3-pyridinecarboxamide (56%) as a pale cream solid; m.p. 78-83° C. (powder-glue), 144-148° C. (glue-liquid). $^1$H NMR [400 MHz, (CD$_3$)$_2$SO] δ 10.25 (br s, 1H), 8.40 (t, J=5.4 Hz, 1H), 8.24 (s, 1H), 7.93 (d, J=8.8 Hz, 1H), 7.89 (d, J=8.8 Hz, 2H), 7.73 (d, J=1.9 Hz, 1H), 7.53-7.37 (m, 3H), 5.88 (s, 1H), 4.49 (t, J=5.1 Hz, 1H), 3.49 (dd, J=11.4, 6.2 Hz, 2H), 3.38 (s, 3H), 3.32-3.26 (m, 2H), 1.69 (p, J=6.7 Hz, 2H). LCMS (ACPI$^-$) 350 (100%). Anal. Calcd for C$_{20}$H$_{21}$N$_3$O$_3$.0.5 H$_2$O: C, 66.7; H, 6.2; N, 11.7. Found C, 66.6; H, 5.9; N, 12.0.

EXAMPLE 43

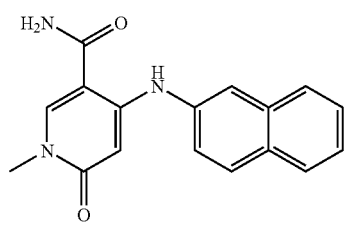

1-Methyl-4-(2-naphthylamino)-6-oxo-1,6-dihydro-3-pyridinecarboxamide

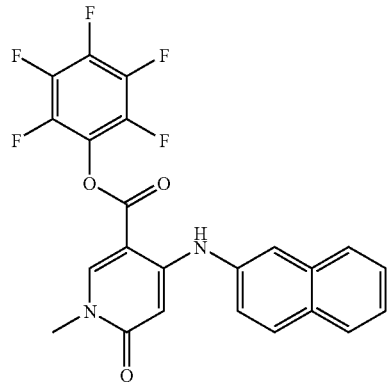

Step A: Preparation of 2,3,4,5,6-pentafluorophenyl 1-methyl-4-(2-naphthylamino)-6-oxo-1,6-dihydro-3-pyridinecarboxylate 1-Methyl-4-(2-naphthylamino)-6-oxo-1,6-dihydro-3-pyridinecarboxylic acid and pentafluorophenyl trifluoroacetate were reacted in the presence of pyridine in THF as for example 4, step A. The crude residue was purified by flash chromatography on silica gel (60% EtOAc/Hexane) to give 2,3,4,5,6-pentafluorophenyl 1-methyl-4-(2-naphthylamino)-6-oxo-1,6-dihydro-3-pyridinecarboxylate (97%). $^1$H NMR [400 MHz, (CD$_3$)$_2$SO] δ 9.06 (s, 1H), 8.97 (s, 1H), 7.98 (d, J=8.8 Hz, 1H), 7.92 (t, J=9.0 Hz, 2H), 7.85 (d, J=1.9 Hz, 1H), 7.56-7.46 (m, 3H), 5.73 (s, 1H), 3.51 (s, 3H).

Step B: Preparation of 1-methyl-4-(2-naphthylamino)-6-oxo-1,6-dihydro-3-pyridinecarboxamide 2,3,4,5,6-Pentafluorophenyl 1-methyl-4-(2-naphthylamino)-6-oxo-1,6-dihydro-3-pyridinecarboxylate in THF was reacted with conc. NH$_3$ solution as for example 37, step B. The crude product was recrystallised (MeOH/EtOAc) to give 1-methyl-4-(2-naphthylamino)-6-oxo-1,6-dihydro-3-pyridinecarboxamide as a white solid (87%); m.p. (MeOH/EtOAc) 254-257° C. $^1$H NMR [400 MHz, (CD$_3$)$_2$SO] δ 10.56 (s, 1H), 8.35 (s, 1H), 7.95-7.86 (m, 4H), 7.74 (d, J=1.9 Hz, 1H), 7.53-7.42 (m, 3H), 7.39 (dd, J=8.7, 2.1 Hz, 1H), 5.86 (s, 1H), 3.37 (s, 3H). LCMS (ACPI$^-$) 292 (100%). Anal. Calcd for C$_{17}$H$_{15}$N$_3$O$_2$: C, 69.6; H, 5.2; N, 14.3. Found C, 69.4; H, 5.2; N, 14.5.

EXAMPLE 44

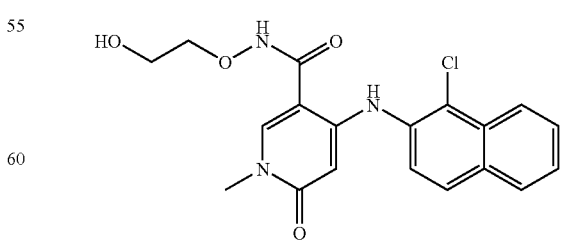

4-[(1-Chloro-2-naphthyl)amino]-N-(2-hydroxyethoxy)-1-methyl-6-oxo-1,6-dihydro-3-pyridinecarboxamide

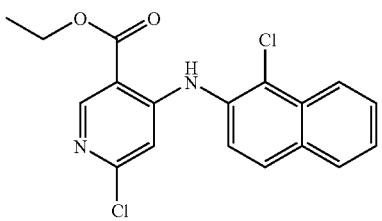

Step A: Preparation of ethyl 6-chloro-4-[(1-chloro-2-naphthyl)amino]nicotinate

1-Chloro-2-naphthalenamine and ethyl 4,6-dichloronicotinate were reacted in a mixture of EtOH and conc. HCl as described for example 33, step A. The resultant solid was isolated by filtration and washed with 10% Et$_2$O/Hexane, giving ethyl 6-chloro-4-[(1-chloro-2-naphthyl)amino]nicotinate (22%). $^1$H NMR [400 MHz, (CD$_3$)$_2$SO] δ 10.07 (br s, 1H), 8.75 (s, 1H), 8.23 (d, J=8.7 Hz, 1H), 8.09-8.05 (m, 2H), 7.77-7.71 (m, 2H), 7.66 (ddd, J=8.0, 6.9, 1.1 Hz, 1H), 6.75 (s, 1H), 4.41 (q, J=7.1 Hz, 2H), 1.38 (t, J=7.1 Hz, 3H).

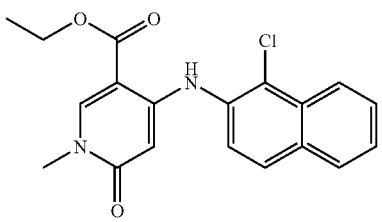

Step B: Preparation of ethyl 4-[(1-chloro-2-naphthyl)amino]-1-methyl-6-oxo-1,6-dihydro-3-pyridinecarboxylate Ethyl 6-chloro-4-[(1-chloro-2-naphthyl)amino]nicotinate was dissolved in CHCl$_3$ and reacted with Me$_2$SO$_4$, followed by triethylamine, AcOH and EtOH as described for example 33, step B. Purification by flash chromatography on silica gel (50% EtOAc/Hexane) afforded ethyl 4-[(1-chloro-2-naphthyl)amino]-1-methyl-6-oxo-1,6-dihydro-3-pyridinecarboxylate (71%). $^1$H NMR [400 MHz, (CD$_3$)$_2$SO] δ 9.73 (s, 1H), 8.59 (s, 1H), 8.18 (d, J=8.4 Hz, 1H), 8.02 (t, J=8.4 Hz, 2H), 7.75-7.69 (m, 2H), 7.64-7.59 (m, 1H), 5.59 (s, 1H), 4.34 (q, J=7.1 Hz, 2H), 3.45 (s, 3H), 1.35 (t, J=7.1 Hz, 3H).

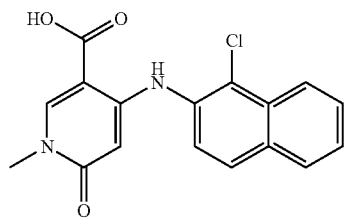

Step C: Preparation of 4-[(1-chloro-2-naphthyl)amino]-1-methyl-6-oxo-1,6-dihydro-3-pyridinecarboxylic acid Ethyl 4-[(1-chloro-2-naphthyl)amino]-1-methyl-6-oxo-1,6-dihydro-3-pyridine-carboxylate was dissolved in EtOH and treated with 1M NaOH for 15 h as for example 33, step C. The precipitate which formed on addition of 1M HCl was washed with copious amounts of water then dried under vacuum to give 4-[(1-chloro-2-naphthyl)amino]-1-methyl-6-oxo-1,6-dihydro-3-pyridinecarboxylic acid (87%). $^1$H NMR [400 MHz, (CD$_3$)$_2$SO] δ 13.50 (v br s, 1H), 10.16 (br s, 1H), 8.56 (s, 1H), 8.18 (d, J=8.4 Hz, 1H), 8.02 (t, J=8.7 Hz, 2H), 7.76-7.68 (m, 2H), 7.61 (dd, J=8.1, 1.0 Hz, 1H), 5.93 (s, 1H), 3.43 (s, 3H).

Step D: Preparation of 4-[(1-chloro-2-naphthyl)amino]-N-(2-hydroxyethoxy)-1-methyl-6-oxo-1,6-dihydro-3-pyridinecarboxamide 2-(Aminooxy)ethanol, 4-[(1-chloro-2-naphthyl)amino]-1-methyl-6-oxo-1,6-dihydro-3-pyridinecarboxylic acid, DMT-MM and N-MM (2 eq) were reacted in 20% water/MeOH for 15 h according to the procedure outlined in example 33, step D. Further purification by flash chromatography on silica gel (EtOAc followed by 10% MeOH/CH$_2$Cl$_2$—100% MeOH gradient elution) gave 4-[(1-chloro-2-naphthyl)amino]-N-(2-hydroxyethoxy)-1-methyl-6-oxo-1,6-dihydro-3-pyridinecarboxamide (24%). $^1$H NMR [400 MHz, (CD$_3$)$_2$SO] δ 11.72 (br s, 1H), 9.89 (br s, 1H), 8.20-8.14 (m, 1H), 7.98 (t, J=9.6 Hz, 2H), 7.74-7.67 (m, 2H), 7.61-7.56 (m, 2H), 5.69 (s, 1H), 4.78 (br s, 1H), 3.94 (t, J=4.8 Hz, 2H), 3.67-3.61 (m, 2H), 3.38 (s, 3H). LCMS (ACPI$^-$) 386 (100%).

EXAMPLE 45

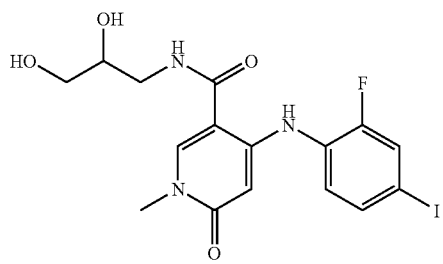

N-(2,3-Dihydroxypropyl)-4-(2-fluoro-4-iodoanilino)-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid and CDI were dissolved in anhydrous THF/DMF (5:1) and treated with 3-amino-1,2-propandiol as for example 34. After workup, the residue was further purified by flash chromatography on silica gel (5% MeOH/CH$_2$Cl$_2$—10% MeOH/CH$_2$Cl$_2$ gradient elution) to give N-(2,3-dihydroxypropyl)-4-(2-fluoro-4-iodoanilino)-1-methyl-6-oxo-1,6-dihydro-3-pyridinecarboxamide (33%) as a pale cream solid; m.p. (EtOAc/Hexane) 96-101° C. (glue-liquid). $^1$H NMR [400 MHz, CH$_3$OD] δ 8.17 (s, 1H), 7.61 (dd, J=9.9, 1.9 Hz, 1H), 7.59-7.55 (m, 1H), 7.22 (t, J=8.4, 1H), 5.78 (s, 1H), 3.85-3.79 (m, 1H), 3.56 (dd, J=5.4, 2.3 Hz, 2H), 3.51 (s, 3H), 3.53-3.50 (m, 1H), 3.39-3.33 (m, 1H). HRMS (FAB$^+$) calcd for C$_{16}$H$_{18}$FIN$_3$O$_4$ 462.0326 (M$^+$), found 462.0332. HPLC 84.8% (254 nm).

EXAMPLE 46

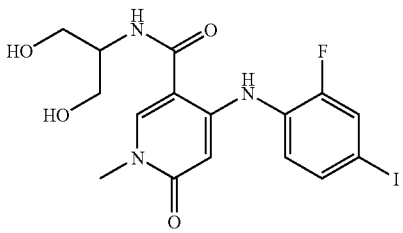

4-(2-Fluoro-4-iodoanilino)-N-[2-hydroxy-1-(hydroxymethyl)ethyl]-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid and CDI were dissolved in anhydrous THF/DMF (5:1) and treated with 2-amino-1,3-propandiol as for example 34. After workup, the residue was further purified by flash chromatography on silica gel (5% MeOH/CH$_2$Cl$_2$—10% MeOH/CH$_2$Cl$_2$ gradient elution) to give 4-(2-fluoro-4-iodoanilino)-N-[2-hydroxy-1-(hydroxymethyl)ethyl]-1-methyl-6-oxo-1,6-dihydro-3-pyridinecarboxamide (34%) as a white solid; m.p. (EtOAc/Hexane) 93-98° C. (glue-liquid). $^1$H NMR [400 MHz, CH$_3$OD] δ 8.22 (s, 1H), 7.61 (dd, J=9.9, 1.8 Hz, 1H), 7.58-7.54 (m, 1H), 7.21 (t, J=8.4, 1H), 5.78 (d, J=1.1 Hz, 1H), 4.12 (p, J=5.6 Hz, 1H), 3.72 (ddd, J=15.1, 11.2, 5.6 Hz, 4H), 3.51 (s, 3H). HRMS (FAB$^+$) calcd for C$_{16}$H$_{18}$FIN$_3$O$_4$ 462.0326 (M$^+$), found 462.0323. HPLC 89.9% (254 nm).

EXAMPLE 47

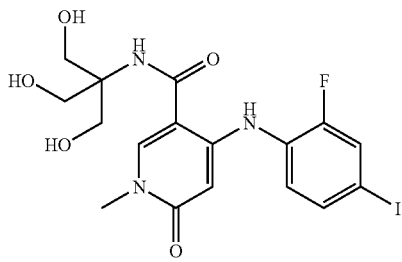

4-(2-Fluoro-4-iodoanilino)-N-[2-hydroxy-1,1-bis(hydroxymethyl)ethyl]-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid and CDI were dissolved in anhydrous THF/DMF (4:1) and treated with 2-amino-2-[hydroxymethyl]-1,3-propandiol as for example 34. After the standard workup, trituration with hexane gave 4-(2-fluoro-4-iodoanilino)-N-[2-hydroxy-1,1-bis(hydroxymethyl)ethyl]-1-methyl-6-oxo-1,6-dihydro-3-pyridinecarboxamide (22%) as a yellow/cream solid; m.p. (EtOAc/Hexane) 100-105° C. (glue-liquid). $^1$H NMR [400 MHz, (CD$_3$)$_2$SO] δ 9.62 (br s, 1H), 8.15 (s, 1H), 7.73 (dd, J=10.2, 1.7 Hz, 1H), 7.57 (d, J=8.5 Hz, 1H), 7.32 (s, 1H), 7.26 (t, J=8.5 Hz, 1H), 5.54 (s, 1H), 4.59 (t, J=5.7 Hz, 3H), 3.68 (d, J=5.7 Hz, 6H), 3.37 (s, 3H). HPLC 78.1% (254 nm). HRMS (FAB$^+$) calcd for C$_{17}$H$_{20}$FIN$_3$O$_5$ 492.043 (M$^+$), found 492.0425.

EXAMPLE 48

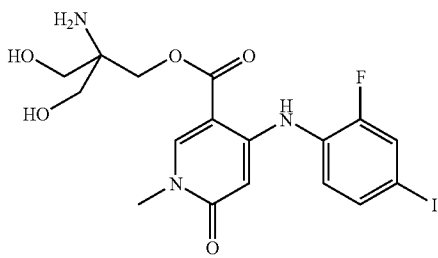

2-Amino-3-hydroxy-2-(hydroxymethyl)propyl-4-(2-fluoro-4-iodoanilino)-1-methyl-6-oxo-1,6-dihydro-3-pyridinecarboxylate 4-(2-Fluoro-4-iodoanilino)-1-methyl-6-oxo-1,6-dihydro-3-pyridinecarboxylic acid and CDI were dissolved in anhydrous THF/DMF (5:1) and treated with 2-amino-2-[hydroxymethyl]-1,3-propandiol as for example 34. After stirring at RT for 60 h, a precipitate had formed. The solid was isolated by filtration and further purified by flash chromatography on silica gel (5% MeOH/CH$_2$Cl$_2$—10% MeOH/CH$_2$Cl$_2$ gradient elution) to give 2-amino-3-hydroxy-2-(hydroxymethyl)propyl 4-(2-fluoro-4-iodoanilino)-1-methyl-6-oxo-1,6-dihydro-3-pyridinecarboxylate (7%) as a white solid; m.p. (EtOAc/Hexane) 117-122° C. (glue-liquid). $^1$H NMR [400 MHz, (CD$_3$)$_2$CO] δ 9.44 (br s, 1H), 8.61 (s, 1H), 7.67 (dd, J=9.9, 1.8 Hz, 1H), 7.66-7.62 (m, 1H), 7.35 (dt, J=8.4, 2.4 Hz, 1H), 5.62 (dd, J=6.3, 1.2 Hz, 1H), 4.26 (s, 2H), 3.56 (d, J=1.8 Hz, 4H), 3.49 (s, 3H). HRMS (FAB$^+$) calcd for C$_{17}$H$_{20}$FIN$_3$O$_5$ 492.0432 (M$^+$), found 492.0450. HPLC 88.9% (254 nm).

EXAMPLE 49

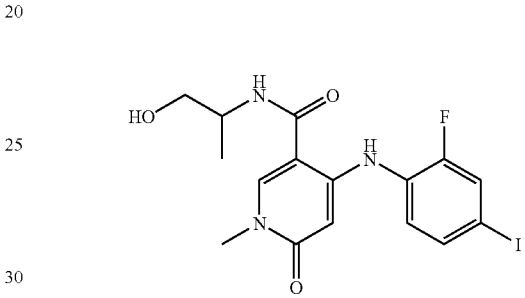

4-(2-Fluoro-4-iodoanilino)-N-(2-hydroxy-1-methylethyl)-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid and CDI were dissolved in anhydrous THF/DMF (4:1) and treated with 2-amino-1-propanol as for example 34. After workup, the residue was triturated with hexane, then dried to give 4-(2-fluoro-4-iodoanilino)-N-(2-hydroxy-1-methylethyl)-1-methyl-6-oxo-1,6-dihydro-3-pyridinecarboxamide (40%) as a cream solid; m.p. (EtOAc/Hexane) 198-202° C. $^1$H NMR [400 MHz, (CD$_3$)$_2$SO] δ 10.10 (br s, 1H), 8.26 (s, 1H), 8.08 (d, J=7.8 Hz, 1H), 7.72 (dd, J=10.2, 1.7 Hz, 1H), 7.57 (d, J=8.5 Hz, 1H), 7.28 (t, J=8.5 Hz, 1H), 5.58 (s, 1H), 4.73 (t, J=5.8 Hz, 1H), 3.97 (p, J=6.7 Hz, 1H), 3.47-3.39 (m, 1H), 3.38 (s, 3H), 3.37-3.33 (m, 1H), 1.12 (d, J=6.7 Hz, 3H). HRMS (FAB$^+$) calcd for C$_{16}$H$_{18}$FIN$_3$O$_3$ 446.0377 (M$^+$), found 446.0383. HPLC 95.1% (254 nm).

EXAMPLE 50

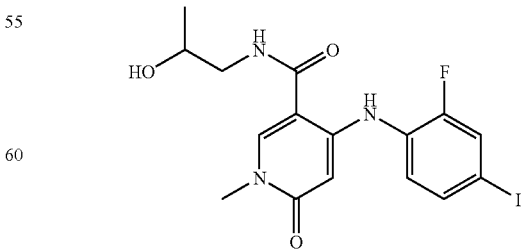

4-(2-Fluoro-4-iodoanilino)-N-(2-hydroxypropyl)-1-methyl-6-oxo-1,6-dihydro-3-pyridinecarboxamide 4-(2-Fluoro-4-iodoanilino)-1-methyl-6-oxo-1,6-dihydro-3-pyridinecarboxylic acid and CDI were dissolved in anhydrous THF/DMF (4:1) and treated with 1-amino-2-propanol as for example 34. After workup, the residue was triturated with hexane then dried, affording 4-(2-fluoro-4-iodoanilino)-N-(2-hydroxypropyl)-1-methyl-6-oxo-1,6-dihydro-3-pyridinecarboxamide (36%) as a white solid; m.p. (EtOAc/Hexane) 161-166° C. (glue-liquid). $^1$H NMR [400 MHz, (CD$_3$)$_2$CO] δ 10.13 (br s, 1H), 8.31 (t, J=1.7 Hz, 1H), 7.73 (br s, 1H), 7.66-7.58 (m, 2H), 7.37-7.31 (m, 1H), 5.75 (dd, J=5.2, 0.9 Hz, 1H), 3.96-3.88 (m, 1H), 3.46-3.39 (m, 1H), 3.42 (s, 3H), 3.25-3.17 (m, 1H), 1.15 (d, J=6.2 Hz, 3H). HRMS (FAB$^+$) calcd for C$_{16}$H$_{18}$FIN$_3$O$_3$ 446.0377 (M$^+$), found 446.0371. HPLC 96.8% (254 nm).

EXAMPLE 51

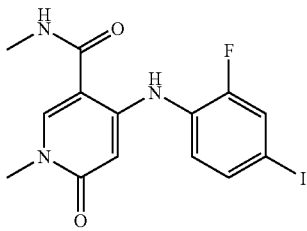

4-(2-Fluoro-4-iodoanilino)-N,1-dimethyl-6-oxo-1,6-dihydro-3-pyridinecarboxamide

Methylamine (40% in aqueous solution) was added to 2,3,4,5,6-pentafluorophenyl 4-(2-fluoro-4-iodoanilino)-1-methyl-6-oxo-1,6-dihydro-3-pyridinecarboxylate in THF as for example 37, step B, and the solution stirred at RT for 15 h. The resultant precipitate was isolated by filtration and washed with hexane to afford 4-(2-fluoro-4-iodoanilino)-N,1-dimethyl-6-oxo-1,6-dihydro-3-pyridinecarboxamide as a white solid. Additional product could be obtained by further purifying the filtrate, (73%); m.p. 252-254° C. $^1$H NMR [400 MHz, (CD$_3$)$_2$SO] δ 10.10 (br s, 1H), 8.41 (br d, J=4.4 Hz, 1H), 8.22 (s, 1H), 7.72 (dd, J=10.2, 1.9 Hz, 1H), 7.57 (dt, J=8.4, 0.9 Hz, 1H), 7.28 (t, J=8.4 Hz, 1H), 5.58 (d, J=0.9 Hz, 1H), 3.36 (s, 3H), 2.75 (d, J=4.4 Hz, 3H). HRMS (FAB$^+$) calcd for C$_{14}$H$_{14}$FIN$_3$O$_2$ 402.0115 (M$^+$), found 402.0119. HPLC 98.0% (254 nm).

EXAMPLE 52

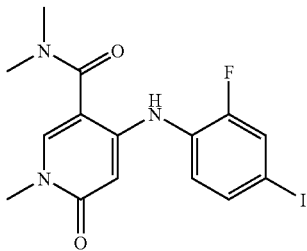

4-(2-Fluoro-4-iodoanilino)-N,N,1-trimethyl-6-oxo-1,6-dihydro-3-pyridinecarboxamide Dimethylamine (40% in aqueous solution) was added to 2,3,4,5,6-pentafluorophenyl 4-(2-fluoro-4-iodoanilino)-1-methyl-6-oxo-1,6-dihydro-3-pyridinecarboxylate in THF as for example 37, step B, and the solution stirred at RT for 15 h. The resultant precipitate was removed by filtration and washed with hexane and Et$_2$O. The filtrate was concentrated under reduced pressure and triturated with hexane to give 4-(2-fluoro-4-iodoanilino)-N,N,1-trimethyl-6-oxo-1,6-dihydro-3-pyridinecarboxamide as a pale yellow solid (58%); m.p. 106-111° C. (glue-liquid). $^1$H NMR [400 MHz, (CD$_3$)$_2$SO] δ 8.21 (s, 1H), 7.79 (s, 1H), 7.72 (dd, J=10.2, 1.9 Hz, 1H), 7.56 (dt, J=8.4, 1.2 Hz, 1H), 7.16 (t, J=8.4 Hz, 1H), 5.41 (d, J=1.2 Hz, 1H), 3.34 (s, 3H), 2.98 (s, 6H). HRMS (FAB$^+$) calcd for C$_{15}$H$_{16}$FIN$_3$O$_2$ 416.0271 (M$^+$), found 416.0270. HPLC 97.2% (254 nm).

EXAMPLE 53

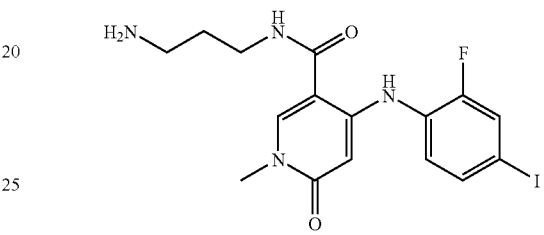

N-(3-Aminopropyl)-4-(2-fluoro-4-iodoanilino)-1-methyl-6-oxo-1,6-dihydro-3-pyridinecarboxamide 2,3,4,5,6-pentafluorophenyl 4-(2-fluoro-4-iodoanilino)-1-methyl-6-oxo-1,6-dihydro-3-pyridinecarboxylate (0.20 g, 0.4 mmol) in THF (5 ml) was added to 1,3-propanediamine (0.35 ml, >10 eq) in THF (5 ml) and stirred at RT for 15 h. The solution was then concentrated under reduced pressure and the residue dissolved in 5% MeOH/EtOAc. The organic phase was washed with water, brine, dried (Na$_2$SO$_4$) and concentrated to give crude N-(3-aminopropyl)-4-(2-fluoro-4-iodoanilino)-1-methyl-6-oxo-1,6-dihydro-3-pyridinecarboxamide which was then recrystallised (MeOH/Hexane/EtOAc) (0.04 g, 22%); m.p. 201-206° C. $^1$H NMR [400 MHz, (CD$_3$)$_2$SO] δ 8.42 (br s, 1H), 8.25 (s, 1H), 7.74 (dd, J=10.2, 1.9 Hz, 1H), 7.57 (dt, J=8.5, 0.9 Hz, 1H), 7.29 (t, J=8.5 Hz, 1H), 5.60 (d, J=0.9 Hz, 1H), 3.38 (s, 3 H, obscured), 3.3-3.25 (m, 2 H, obscured), 2.81 (t, J=7.4 Hz, 2H), 1.75 (p, J=7.4 Hz, 2H). HPLC 94.4% (254 nm). HRMS (FAB$^+$) calcd for C$_{16}$H$_{19}$FIN$_4$O$_2$ 445.0537 (M$^+$), found 445.0543.

EXAMPLE 54

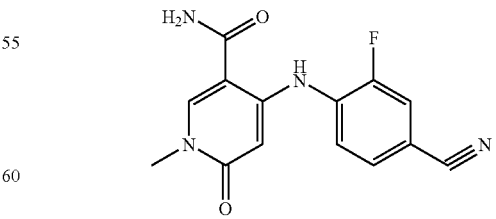

4-(4-Cyano-2-fluoroanilino)-1-methyl-6-oxo-1,6-dihydro-3-pyridinecarboxamide 4-(2-Fluoro-4-iodoanilino)-1-methyl-6-oxo-1,6-dihydro-3-pyridinecarboxamide (0.20 g, 0.5 mmol) was added to potassium cyanide (0.23 g, 3.5 mmol), copper(I)iodide (excess) and tetrakis(triphenylphosphine)palladium(0) (excess) in DMF (30 ml) and heated at 110° C. for 4 h. The reaction mixture was allowed to cool to RT and filtered through Celite® to remove any solid. The Celite® pad was washed well with 5% MeOH/EtOAc. The filtrate and washings were combined and concentrated under reduced pressure. The residue was dissolved in 5% MeOH/EtOAc, then washed with water, brine, dried ($Na_2SO_4$), concentrated and triturated with EtOAc giving an approximately 1:1 mixture of 4-(2-fluoro-4-iodoanilino)-1-methyl-6-oxo-1,6-dihydro-3-pyridinecarboxamide and 4-(4-cyano-2-fluoroanilino)-1-methyl-6-oxo-1,6-dihydro-3-pyridinecarboxamide. Further purification by preparative HPLC [90% ($H_2O$/TFA)/(acetonitrile/TFA)—1% ($H_2O$/TFA)/(acetonitrile/TFA) gradient elution 0.8 ml/min, pH 2.5-2.6] yielded 4-(4-cyano-2-fluoroanilino)-1-methyl-6-oxo-1,6-dihydro-3-pyridinecarboxamide (0.01 g, 7%); m.p. 261-266° C. $^1$H NMR [400 MHz, $(CD_3)_2SO$] δ 11.01 (s, 1H), 8.39 (s, 1H), 7.91 (dd and br s, J=11.2, 1.7 Hz, 2H), 7.72 (t, J=8.2 Hz, 1H), 7.66 (dd, J=8.6, 1.7 Hz, 1H), 7.52 (br s, 1H), 5.97 (s, 1H), 3.40 (s, 3H). HPLC 95.5% (254 nm). HRMS (FAB$^+$) cald for $C_{14}H_{11}FN_4O_2$ 286.0866 (M+), found 286.0864.

EXAMPLE 55

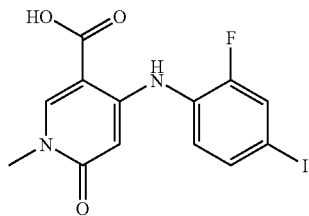

4-(2-fluoro-4-iodoanilino)-1-methyl-6-oxo-1,6-dihydro-3-pyridinecarboxylic acid

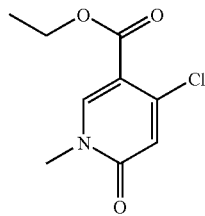

Step A: Preparation of 4-Chloro-1-methyl-6-oxo-1,6-dihydro-pyridine-3-carboxylic acid ethyl ester Ethyl 4,6-dichloronicotinate [prepared according to the literature procedure of *J. Chem. Soc.* 5163 (1963)] (3.19 g, 14.5 mmol) and dimethyl sulfate (6.0 mL, 63 mmol) were combined in a thick-walled glass tube with a Teflon cap. The tube was sealed and heated in a 120° C. sand bath. After 5 h, the reaction was cooled to ambient temperature and diluted with acetonitrile (100 mL) and saturated aqueous sodium bicarbonate solution (100 mL). The reaction mixture was stirred vigorously overnight (ca. 18 h). This mixture was further diluted with water and extracted with dichloromethane (3×). The combined extracts were washed with brine, dried over anhydrous magnesium sulfate and concentrated in vacuo to afford 4-chloro-1-methyl-6-oxo-1,6-dihydro-pyridine-3-carboxylic acid ethyl ester (2.65 g, 85% yield) as an oil that solidified upon standing.

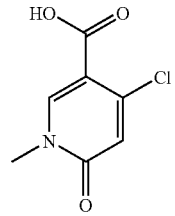

Step B: Preparation of 4-Chloro-1-methyl-6-oxo-1,6-dihydro-pyridine-3-carboxylic acid 4-Chloro-1-methyl-6-oxo-1,6-dihydro-pyridine-3-carboxylic acid ethyl ester (2.65 g, 12.3 mmol) was dissolved in a mixture of tetrahydrofuran (16 mL), acetonitrile (16 mL) and water (8 mL). Sodium hydroxide (1.23 g, 30.8 mmol) was added and the reaction mixture was allowed to stir at ambient temperature for 24 h. The reaction mixture was diluted with water (50 mL) and was acidified to pH 2 with 1 M hydrochloric acid and was extracted many times with ethyl acetate (about 1 L). The extracts were dried over anhydrous magnesium sulfate and concentrated in vacuo to afford an orange-tinged solid. Crystallization from methanol-ethyl acetate afforded 4-chloro-1-methyl-6-oxo-1,6-dihydro-pyridine-3-carboxylic acid (0.859 g, 37% yield) as an off-white solid: $^1$H NMR (DMSO-$d_6$, 400 MHz) δ 13.02 (br s, 1H), 8.58 (s, 1H), 6.58 (s, 1H), 3.48 (s, 3H).

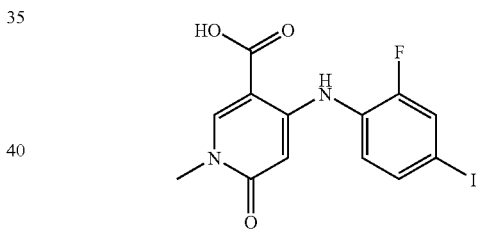

Step C: Preparation of 4-(2-fluoro-4-iodoanilino)-1-methyl-6-oxo-1,6-dihydro-3-pyridinecarboxylic acid 4-Chloro-1-methyl-6-oxo-1,6-dihydro-pyridine-3-carboxylic acid (133 mg, 0.709 mmol) and 2-fluoro-4-iodoaniline (172 mg, 0.726 mmol) were combined in a round bottom flask equipped with magenetic stir bar. The flask was immersed in an ice bath and lithium bis(trimethylsilyl)amide (1.0 M in tetrahydrofuran, 5.0 mL, 5.0 mmol) was added slowly (5 min) with vigorous stirring under an atmosphere of nitrogen. The reaction mixture was further stirred for 1 h at 0° C. and 1 h at ambient temperature. The reaction mixture was diluted with 1 M hydrochloric acid and water and was extracted with ethyl acetate (3×). The extracts were dried over magnesium sulfate and concentrated in vacuo. Upon concentrateion, 4-(2-fluoro-4-iodoanilino)-1-methyl-6-oxo-1,6-dihydro-3-pyridinecarboxylic acid (114 mg, 41% yield) was isolated directly from the ethyl acetate by filtration and drying in vacuo: $^1$H NMR (DMSO-$d_6$, 400 MHz) δ 13.30 (v br s, 1H), 9.66 (s, 1H), 8.52 (s, 1H), 7.76 (dd, J=10.1, 1.9 Hz, 1H), 7.59 (br d, J=8.5 Hz, 1H), 7.31 (t, J=8.5 Hz, 1H), 5.49 (s, 1H), 3.41 (s, 3H); MS (APCI+) 388.9.

EXAMPLE 56

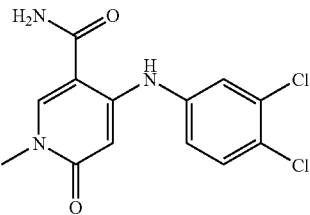

4-(3,4-Dichloro-phenylamino)-1-methyl-6-oxo-1,6-dihydro-pyridine-3-carboxylic acid amide

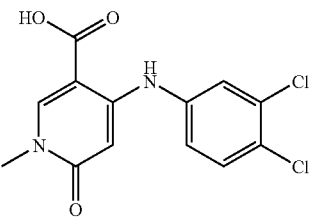

Step A: Preparation of 4-(3,4-Dichloro-phenylamino)-1-methyl-6-oxo-1,6-dihydro-pyridine-3-carboxylic acid A suspension of 4-chloro-1-methyl-6-oxo-1,6-dihydro-pyridine-3-carboxylic acid (161 mg, 0.86 mmol) was treated with lithium diisopropylamide (2.0 M solution in tetrahydrofuran-ethylbenzene-heptane, 0.45 mL, 0.9 mmol). The resultant solution was stirred for 30 min at ambient temperature under nitrogen and was then cooled to −78° C. This is solution A. In a separate flask, a solution of 3,4-dichloroaniline (147 mg, 1.21 mmol) in tetrahydrofuran (3.0 mL) was cooled to −78° C. and treated with lithium diisopropylamide (2.0 M solution in tetrahydrofuran-ethylbenzene-heptane, 1.2 mL, 2.4 mmol). The resultant solution was stirred for 30 min at −78° C. and was transferred to solution A (also at −78° C.) via cannula. The resultant reaction mixture was stirred for 30 min at −78° C. and was then warmed to ambient temperature for 2.5 h. The reaction was diluted with ethyl ether (10 mL) and filtered. The solid was washed with ether (10 mL). The filtrate and washings were discarded. The solid was partitioned between ethyl acetate (60 mL) and 1 N hydrochloric acid (20 mL). The organics were washed with water (2×20 mL) and brine (20 mL). The combined aqueous portion was further extracted with ethyl acetate (20 mL). All organics were combined and dried over magnesium sulfate and concentrated in vacuo to afford a brown-colored solid (234 mg), used in step B without further purification.

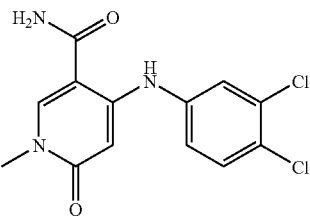

Step B: Preparation of 4-(3,4-Dichloro-phenylamino)-1-methyl-6-oxo-1,6-dihydro-pyridine-3-carboxylic acid amide The product of step A (234 mg) was dissolved in dichloromethane (5 mL) and ethanolic ammonia (2 M, 2.0 mL, 4.0 mmol): PyBOP (579 mg, 1.10 mmol) was added in one portion and the reaction mixture was stirred overnight at ambient temperature. The reaction mixture was quenched with acetic acid (ca. 0.5 mL), diluted with ethyl acetate (40 mL) and washed with water (2×10 mL) and saturated brine (10 mL). The organics were dried over magnesium sulfate, concentrated in vacuo and chromatographed on silica gel. Elution with dichloromethane-methanol (4:1) afforded 4-(3,4-Dichloro-phenylamino)-1-methyl-6-oxo-1,6-dihydro-pyridine-3-carboxylic acid amide (28 mg, 12% yield) as a dark yellow-colored solid. An analytical sample was prepared by crystallization from methanol: m.p. >250° C.; $^1$H NMR (DMSO-d$_6$, 400 MHz) δ10.38 (s, 1H), 8.30 (s, 1H), 7.85 (br s, 1H), 7.57 (d, J=8.8 Hz, 1H), 7.48 (d, J=2.4 Hz, 1H), 7.45 (br s, 1H), 7.23 (dd, J=8.8, 2.4 Hz, 1H), 5.70 (s, 1H), 3.33 (s, 3H). Anal. Calcd./Found for $C_{13}H_{11}Cl_2N_3O_2$: C, 50.02/50.02; H, 3.55/3.19; N, 13.46/13.21.

The following examples, 57 to 60, were prepared by the procedure of Example 33, Steps A and B.

EXAMPLE 57

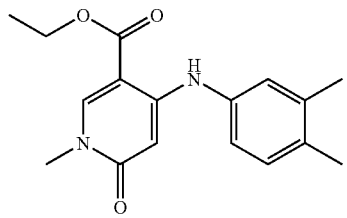

4-(3,4-Dimethyl-phenylamino)-1-methyl-6-oxo-1,6-dihydro-pyridine-3-carboxylic acid ethyl ester $C_{17}H_{20}N_2O_3$; m.p. 153-154° C.; MS (APCI+) 301.1 [M+H]; HPLC 3.377 minutes 95.04%; NMR (400 MHz, CDCl$_3$) δ 9.23 (bs, 1H), 8.17 (s, 1H), 7.09 (d, J=8.1 Hz, 1H), 6.99 (d, J=2.0 Hz, 1H), 6.94 (dd, J=8.1, 2.2 Hz, 1H), 5.89 (s, 1H), 4.31 (q, J=7.1 Hz, 2H), 3.50 (s, 3H), 2.22 (s, 6H), 1.37 (t, J=7.1 Hz, 3H).

EXAMPLE 58

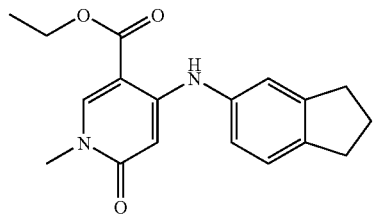

4-(Indan-5-ylamino)-1-methyl-6-oxo-1,6-dihydro-pyridine-3-carboxylic acid ethyl ester $C_{18}H_{20}N_2O_3$, m.p. 141-143° C., MS (APCI+) 313.1 [M+H], HPLC 3.499 m. 100%, NMR 400 MHz, CDCl$_3$ δ

9.25 (br s, 1H), 8.17 (s, 1H), 7.18 (d, J=7.8 Hz, 1H), 7.086 (s, 1H), 6.95 (dd, J=8.1, 2.0, 1H), 5.88 (s, 1H), 4.32 (q, J=7.1, 2H), 3.51 (s, 3H), 2.87 (t, J=7.3, 4H), 2.07 (m 2H), 1.37 (t, J=7.1, 3H).

EXAMPLE 59

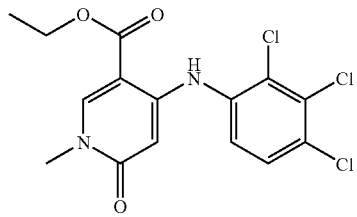

1-Methyl-6-oxo-4-(2,3,4-trichloro-phenylamino)-1,6-dihydro-pyridine-3-carboxylic acid ethyl ester $C_{15}H_{13}Cl_4N_2O_2$; MS (APCI+) 376 [M+H]; HPLC 3.788 m. 100%; NMR (CDCl$_3$) δ 9.67 (br s, 1H), 8.24 (s, 1H), 7.38 (d, J=1.2 Hz, 2H), 5.95 (s, 1H), 4.36 (q, J=7.1 Hz, 2H), 3.55 (s, 3H), 1.39 (t, J=7.1 Hz, 3H).

EXAMPLE 60

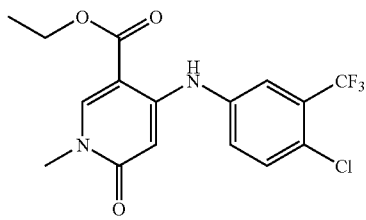

4-(4-Chloro-3-trifluoromethyl-phenylamino)-1-methyl-6-oxo-1,6-dihydro-pyridine-3-carboxylic acid ethyl ester $C_{16}H_{14}ClF_3N_2O_3$; MS (APCI+) 375 [M+H]; HPLC 3.409 m. 100%; NMR (400 MHz, CDCl$_3$) δ 9.54 (br s,1H), 8.22 (s, 1H), 7.51 (d, J=2.4 Hz, 1H), 7.48 (d, J=J=8.5 Hz, 1H), 7.38 (dd, J=8.5, 2.4 Hz, 1H), 5.93 (s,1H), 4.33 (q, J=7.1 Hz, 2H), 3.54 (s, 3H), 3.54 (s, 3H), 1.38 (t, J=7.1 Hz, 3H).

EXAMPLE 61

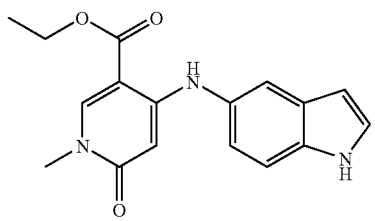

4-(1H-Indol-5-ylamino)-1-methyl-6-oxo-1,6-dihydro-pyridine-3-carboxylic acid ethyl ester

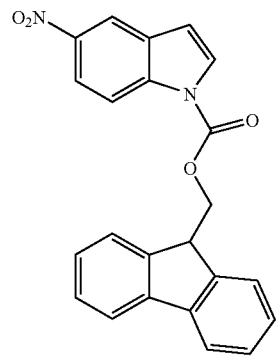

Step A: 5-Nitro-indole-1-carboxylic acid 9H-fluoren-9-ylmethyl ester

5-Nitroindole (2.0 g, 12.3 mmol) was dissolved in dioxane (25 mL) and 10% wt./vol Na$_2$CO$_3$ solution (2.5 g, water 25 mL) was added. FMOC-chloroformate (3.19 g, 12.3 mmol) was added to the mixture and the reaction was stirred overnight. The reaction mixture was transferred into water, filtered as a yellow solid and dried in vacuum oven at 50° C. for 2 hours. Obtained (4.07 g, 86% y). NMR (400 MHz, CDCl$_3$), δ 8.61 (d, J=2.2 Hz, 1H), 8.43 (d, J=2.2 Hz, 1H), 8.12 (dd, J=7.3, 5.1 Hz, 1H), 8.02 (d, J=8.3 Hz, 1H), 7.82 (d, J=7.6 Hz, 2H), 7.76 (d, J=7.6 Hz, 2H), 7.62 (m, 4H), 7.60-7.30 (m, 8H), 6.74-6.69 (m, 2H), 4.94 (d, J=5.4 Hz, 2H), 4.41 (t, J=5.1 Hz, 1H), 4.05 (d, J=5.6 Hz, 2H). MS 384 [M−H] APCI.

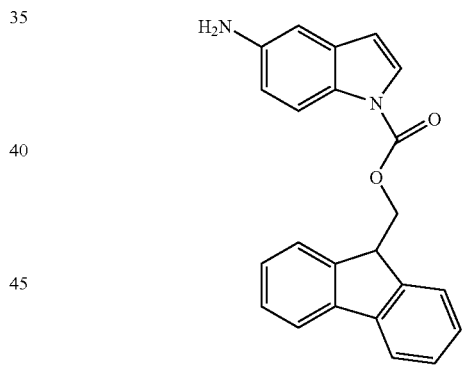

Step B: 5-Amino-indole-1-carboxylic acid 9H-fluoren-9-ylmethyl ester

A solution of 5-nitro-indole-1-carboxylic acid 9H-fluoren-9-ylmethyl ester (4.16 g, 0.0108 mol) in 100 ml of tetrahydrofuran was treated with 1.0 g of sponge nickel catalyst (Activated Metals & Chemicals Co. A-7000, water wet) and hydrogenated in a Parr shaker hydrogenation apparatus (52 to 18 psig, room temperature). After 20 h, the resulting slurry was filtered and the filtrate was returned. Solvent was removed in vacuo to afford a brown oil (4.05 g, 106.6% y). NMR (CDCl$_3$) δ 8.03 (br s, 1H), 7.78 (m, 3H), 7.63 (m,3H), 7.51 (d, J=3.2 Hz, 1H), 7.42 (m, 3H), 7.34 (m, 3H), 7.18 (d, J=8.3 Hz, 1H), 6.49 (d, J=2.3 Hz, 1H), 6.82 (d, J=2.0), 6.66 (dd, J=8.5, 2.2 Hz, 1H), 6.45 (d, J=3.7 Hz, 1H), 6.38 (m, 1H), 4.78 (br s, 2H), 4.43 (t, J=6.3 Hz, 1H), 4.12 (t, J=6.1 HZ, 1H), 4.03 (d, J=0.49 Hz, 2H), 3.76 (t, J=2.4 Hz, 1H), 1.85 (m, 1H). MS 355 [M+H].

Step C: 5-(5-Ethoxycarbonyl-1-methyl-2-oxo-1,2-dihydro-pyridin-4-ylamino)-indole-1-carboxylic acid 9 H-fluoren-9-ylmethyl ester 5-Amino-indole-1-carboxylic acid 9H-fluoren-9-ylmethyl ester was utilized according to the procedures of Example 33, Steps A and B to provide the title compound.

Step D: 4-(1H-Indol-5-ylamino)-1-methyl-6-oxo-1,6-dihydro-pyridine-3-carboxylic acid ethyl ester 5-(5-Ethoxycarbonyl-1-methyl-2-oxo-1,2-dihydro-pyridin-4-ylamino)-indole-1-carboxylic acid 9H-fluoren-9-ylmethyl ester (0.58 g, 1.09 mmol) was dissolved in DCM (10 mL). Piperidine (0.11 mL, 1.09 mmol) was added and the reaction mixture was stirred at RT overnight. Solvent was removed in vacuum. EtOAc was added and the mixture was washed with water (2×), and brine. Filtered white precipitate and dried in vacuum oven for 2 hours. Obtained a white solid (50 mg). The filtrate was dried over MgSO₄ and solvent removed in vacuum. The residue was chromatographed using DCM—8% EtOAc/DCM as eluent. Obtained 2 fractions. Neither fraction was the desired product. The white solid data; HPLC 3.308 minutes, 100% pure, LC/MS 2.789 minutes 100% no mass. MS (APCI+) 312 [M+H]; NMR (400 MHz, DMSO-d₆) δ 11.22 (s,1H), 9.14 (s,1H), 8.460 (s, 1H), 7.38 (m, 3H), 6.93 (dd, J=8.6, 1.5 Hz, 1H), 6.40 (s,1H), 5.32 (s, 1H), 4.27 (q, J=7.1 Hz, 2H), 3.36 (s, 3H), 1.30 (t, J=7.1 Hz, 3H).

EXAMPLE 62

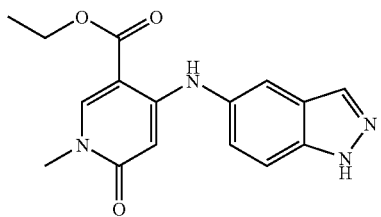

4-(1H-Indazol-5-ylamino)-1-methyl-6-oxo-1,6-dihydro-pyridine-3-carboxylic acid ethyl ester

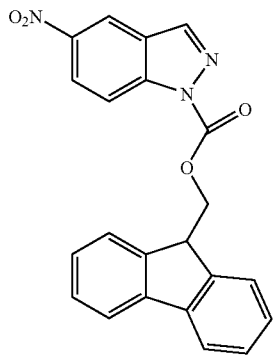

Step A: 5-Nitro-indazole-1-carboxylic acid 9H-fluoren-9-ylmethyl ester

5-Nitroindazole was utilized as a starting material in accordance with Example 61, Step A to afford the title compound as an off-white solid (4.29 g, 90.6% y.). MS APCI 386 [M+H]. NMR (CDCl₃, 400 MHz), δ 8.67 (d, J=1.7 Hz, 1H), 8.39 (d, J=0.7 Hz, 1H), 8.26 (dd, J=9.28, 2.0 Hz, 1H), 7.81 (d, J=7.6 Hz, 3H), 7.73 (d, J=0.7 Hz, 3H), 7.44 (t, J=7.4 Hz, 2H), 7.34 (m, 2H), 4.92 (d, J=6.4 Hz, 2H), 4.48 (t, J=6.4 Hz, 1H).

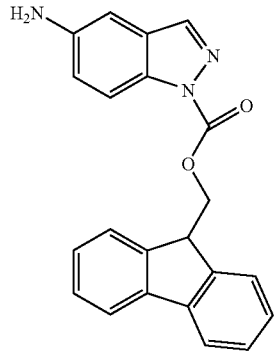

Step B: 5-Amino-indazole-1-carboxylic acid 9H-fluoren-9-ylmethyl ester

5-Nitro-indazole-1-carboxylic acid 9H-fluoren-9-ylmethyl ester was utilized as a starting material in accordance with Example 61, Step B to afford the title compound as a yellow solid (3.99 g, 100% y.). MS 356 [M+H] APCI; NMR (CDCl₃, 400 MHz) δ 8.06 (s, 1H), 7.79 (d, J=7.6 Hz, 3H), 7.21 (d, J=7.3 Hz, 3H), 7.42 (t, J=7.44 Hz, 3H), 7.34 (q, J=7.3, 1.1 Hz, 3H), 6.92 (d, J=2.0 Hz, 1H), 6.86 (d, J=8.5 Hz, 3H), 4.81 (d, J=6.6 Hz, 1H), 3.74 (br s, 2H), 3.48 (s, 1H).

Step C: 5-Amino-indazole-1-carboxylic acid 9H-fluoren-9-ylmethyl ester was utilized according to the procedures of Example 33, Steps A and B and Example 61, Step D to provide the title compound MS (APCI+) 313 [M+H]; HPLC 3.170 m. 97.25%; C₁₆H₁₆N₄O₃; CHN Calc. C)61.53% H)5.16% N)17.94% found C)50.88% H)4.09% N)14.33% NMR (400 MHz, DMSO-d₆) δ 13.16 (s, 1H), 9.22 (s, 1H), 8.48 (s, 1H), 8.03 (s, 1H), 7.61 (d, J=1.2 Hz, 1H), 7.56 (d, J=8.8 Hz, 1H), 7.22 (d, J=8.5, 1.7, 1H), 5.34 (s, 1H), 4.27 (q, J=7.1 Hz, 2H), 3.35 (s, 3H), 1.29 (t, J=7.1 Hz, 3H).

The following examples, 63 to 66, were prepared by the procedure of Example 33, steps A, B and C.

EXAMPLE 63

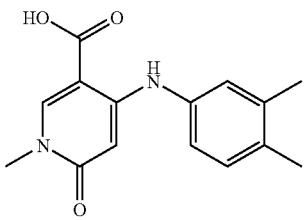

4-(3,4-Dimethyl-phenylamino)-1-methyl-6-oxo-1,6-dihydro-pyridine-3-carboxylic acid C₁₅H₁₆N₂O₃; m.p. 238-242° C.; MS (APCI+) 273 [M+H]; HPLC 2.765 m. 98.4%; NMR (400 MHz, DMSO-d₆) δ 13.15, (br s, 1H), 9.46, (br s, 1H), 8.45 (s, 1H), 7.14 (d, J=8.1 Hz, 1H), 7.01 (d, J=2.0 Hz, 1H), 6.95 (dd, J=7.8, 2.2 Hz, 1H), 5.51 (s, 1H), 3.35 (s, 3H), 2.194 (s, 3H), 2.180 (s, 3H).

EXAMPLE 64

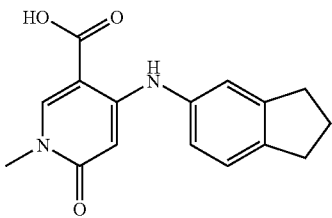

4-(Indan-5-ylamino)-1-methyl-6-oxo-1,6-dihydro-pyridine-3-carboxylic acid $C_{16}H_{16}N_2O_3$; m.p. 218-220° C.; MS (APCI+) 286 [M+H]; HPLC 2.810 m. 92.03%; NMR (400 MHz, DMSO-$d_6$) δ 9.60 (br s, 1H), 8.42 (s, 1H), 7.21 (d, J=7.8 Hz, 1H), 7.08 (s, 1H), 6.95 (dd, J=7.8 Hz, 1H), 5.51, (s, 1H), 3.35 (s, 3H), 2.82 (m, 4H), 1.99 (m, 2H).

EXAMPLE 65

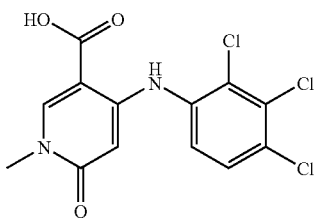

1-Methyl-6-oxo-4-(2,3,4-trichloro-phenylamino)-1,6-dihydro-pyridine-3-carboxylic acid $C_{13}H_9Cl_3N_2O_3$; m.p. 258-261° C.; MS*APCI+) 347, 349 [M+H]; HPLC 2.954 m. 95.3%; NMR (400 MHz, DMSO-$d_6$) δ 8.37 (s, 1H), 7.61 (d, J=8.8 Hz, 1H),7.55 (d, J=9 Hz, 1H), 5.61 (s, 1H), 3.36 (obscured by HDO peak, s, 3H).

EXAMPLE 66

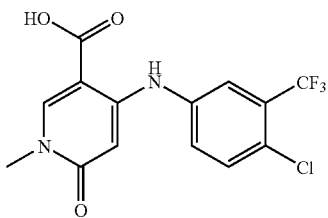

4-(4-Chloro-3-trifluoromethyl-phenylamino)-1-methyl-6-oxo-1,6-dihydro-pyridine-3-carboxylic acid $C_{14}H_{10}Cl_1F_3N_2O_3$; MS (APCI+) 347 [M+H]; HPLC 2.878 m. 98.4%; NMR (400 MHz, DMSO-$d_6$) δ 11.85 (br s, 1H), 8.27 (s, 1H), 7.64 (d, J=8.6 Hz, 1H), 7.55 (m, 1H), 7.52 (m, 1H), 5.74 (s, 1H), 3.35 (obscured by HDO peak, s, 3H).

EXAMPLE 67

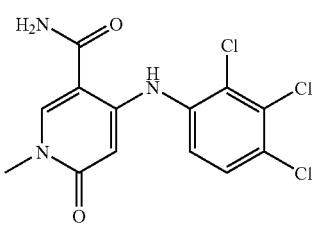

1-Methyl-6-oxo-4-(2,3,4-trichloro-phenylamino)-1,6-dihydro-pyridine-3-carboxylic acid amide The product of Example 65, 1-methyl-6-oxo-4-(2,3,4-trichloro-phenylamino)-1,6-dihydro-pyridine-3-carboxylic acid (0.4 g, 1.15 mmol) was dissolved in DCM (20 mL). Added one drop of DMF and then oxalyl chloride (0.11 mL, 1.27 mmol) was added. Reaction was stirred at rt for 1.5 hours. Then 0.5 N $NH_3$/dioxane (10 mL) was added and stirred for 72 hours. The solvent was removed in vacuum. Ethyl acetate was added and washed with sat. $NaHCO_3$ soln. Filtered solid and dried in vacuum oven 1 hour. Tried to recrystalize using hexanes (5 mL) and EtOAc (30 mL) but never dissolved. Solvent removed in vacuum and took the residue up in ethyl acetate (10 mL)/MeOH (2 mL). Still did not dissolve. Cooled, filtered and dried in vacuum oven overnight at 60° C. Obtained white solid (210.0 mg, 52.7% y.). MS (APCI+) 347,349 [M+H]; HPLC 2.954 m. 94.68%; $C_{13}H_{10}Cl_3N_3O_2$; CHN Calc. C)45.05% H)2.91% N)12.12% found C)27.56% H)1.29% N)3.96%; NMR (400 MHz, DMSO-$d_6$) δ 13.36 (s, 1H), 8.11 (s, 1H), 7.55 (d, J=9.0 Hz, 1H), 7.51 (d, J=9.0 Hz, 1H), 5.67 (s, 1H), 3.31 (s, 3H).

The following examples, 68 to 70, were prepared by the procedure of Example 33, steps A, B and C and Example 67.

EXAMPLE 68

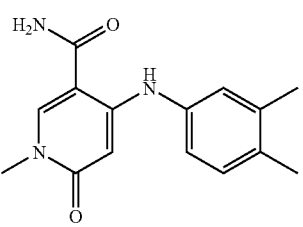

4-(3, -Dimethyl-phenylamino)-1-methyl-6-oxo-1,6-dihydro-pyridine-3-carboxylic acid amide $C_{15}H_{17}N_3O_2$; MS (APCI+) 272 [M+H]; HPLC 5.49 m. 99%; NMR (400 MHz, DMSO-$d_6$) δ 10.08 (s, 1H), 8.23 (s, 1H), 7.77 (br s, 1H), 7.35 (br s, 1H), 7.09 (d, J=8.1 Hz, 1H), 6.93 (d, J=1.7 Hz, 1H), 6.88 (dd, J=8.1, 2.2 Hz, 1H), 5.53 (s, 1H), 3.28 (s, 3H) 2.16 (d, 6H).

EXAMPLE 69

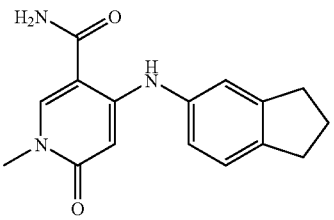

4-(Indan-5-ylamino)-1-methyl-6-oxo-1,6-dihydro-pyridine-3-carboxylic acid amide $C_{16}H_{17}N_2O_3$; MS (APCI+) 286 [M+H]; HPLC 2.717 m. 96.15%; NMR (400 MHz, DMSO-$d_6$) δ 10.13 (s, 1H), 8.26 (s, 1H), 7.79 (br s, 1H), 7.38 (br s, 1H), 7.20 (d, J=7.8 Hz, 1H), 7.05 (s, 1H), 6.92 (d, J=8.1 Hz, 1H), 5.54 (s, 1H), 3.31 (obscured by the DHO peak, s, 3H), 2.79 (m, 4H), 1.98 (m, 2H).

EXAMPLE 70

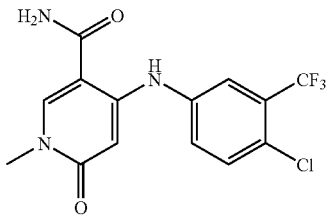

4-(4-Chloro-3-trifluoromethyl-phenylamino)-1-methyl-6-oxo-1,6-dihydro-pyridine-3-carboxylic acid amide $C_{14}H_{10}Cl_1F_3N_3O_2$; MS (APCI+) 346 [M+H]; HPLC 2.819 m. 95.44%; NMR (400 MHz, DMSO-$d_6$) δ 10.43 (s, 1H), 8.29 (s, 1H), 7.85 (br s, 1H), 7.64 (d, J=8.5 Hz, 1H), 7.59 (d, J=2.2 Hz, 1H), 7.54 (d, J=8.8 Hz, 1H), 7.52 (br s, 1H), 5.70 (s, 1H), 3.31 (s, 3H).

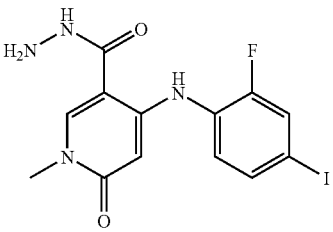

EXAMPLE 71

4-(2-Fluoro-4-iodo-phenylamino)-1-methyl-6-oxo-1,6-dihydro-pyridine-3-carboxylic acid hydrazide To a stirred solution of 4-(2-fluoro-4-iodo-phenylamino)-1-methyl-6-oxo-1,6-dihydro-pyridine-3-carboxylic acid (5.62 g, 14.5 mmol) in DMF (50 mL) was added pyridine (3.5 mL, 43.4 mmol) then followed by dropwise addition of pentafluorophenyl trifluoroacetate (4.5 mL, 43.4 mmol). The mixture was stirred at room temperature for 24 hours. To this mixture was added hydrazine monohydrate (2.8 mL, 58 mmol). The reaction mixture was stirred at room temperature for another 24 hours. The precipitated white solid was collected by filtration and washed with water (5 mL) and hexanes. After drying, the 4-(2-Fluoro-4-iodo-phenylamino)-1-methyl-6-oxo-1,6-dihydro-pyridine-3-carboxylic acid hydrazide was obtained as a white solid (6.55 g, 81%).

$^1$H NMR [(CD$_3$)$_2$SO, 400 MHz] δ 9.90 (s, 1H), 9.63 (s, 1H), 8.15 (s, 1H), 7.73 (d, 1H), 7.58 (d, 1H), 7.26 (t, 1H), 5.58 (s, 1H), 4.42 (br s, 1H), 2.50 (t, 3H). Anal. Calcd for $C_{15}H_{14}FIN_2O_3$: C, 43.3; H, 3.4; N, 6.7. Found: C, 43.7; H, 3.1; N, 7.0.

EXAMPLE 72

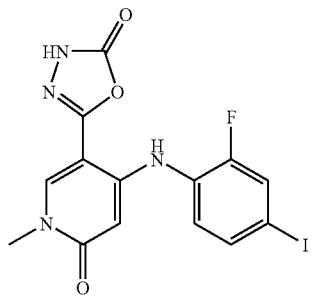

4-(2-Fluoro-4-iodo-phenylamino)-1-methyl-5-(5-oxo-4,5-dihydro-[1,3,4]oxadiazol-2-yl)-1H-pyridin-2-one 4-(2-Fluoro-4-iodo-phenylamino)-1-methyl-6-oxo-1,6-dihydro-pyridine-3-carboxylic acid hydrazide was dissolved in DMF (20 mL) and treated with the 1,1'-carbonydiimidazole (2.90 g, 17.92 mmol). The mixture was stirred at room temperature for 24 hours. The solid was precipitate out. This material was isolated by filtration, washed well with water and hexanes, then dried to afford 4-(2-Fluoro-4-iodo-phenylamino)-1-methyl-5-(5-oxo-4,5-dihydro-[1,3,4]oxadiazol-2-yl)-1H-pyridin-2-one as an off white solid (5.0 g, 71%). (APCI$^+$) calcd for $C_{14}H_{10}FIN_4O_3$ 428.16 (M+1), found 428.9. Anal. Calcd for $C_{14}H_{10}FIN_4O_3$: C, 39.27; H, 2.35; N, 13.09. Found: C, 39.55; H, 2.88; N, 13.12.

EXAMPLE 73

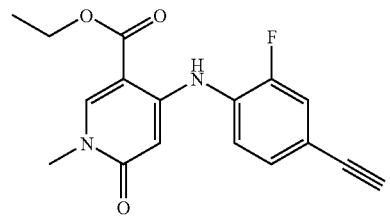

4-(4-Ethynyl-2-fluoro-phenylamino)-1-methyl-6-oxo-1,6-dihydro-pyridine-3-carboxylic acid ethyl ester 4-(2-Fluoro-4-iodo-phenylamino)-1-methyl-6-oxo-1,6-dihydro-pyridine-3-carboxylic acid ethyl ester (1.0 g, 2.40 mmol) was reacted with ethynyl-trimethyl-silane (0.70 mL, 4.80 mmol) in the presence of CuI (0.23 g, 1.20 mmol), (Ph$_3$P)$_2$PdCl$_2$ (0.085 g, 0.12 mmol) and TEA (10 mL) in THF/DMF (4:1, 25 mL) which was stirred at room temperature for 24 hours. The reaction mixture was filtered pass through a pad of alumina (neutral). The filtrate was partitioned between water (20 mL) and EtOAc (100 mL). The organic layer was dried and concentrated under reduced pressure. The resulting residue was dissolved in THF (10 mL) and treated with the tetrabutylammonium fluoride (1M in THF, 2.40 mL, 2.4 mmol) which was stirred at room temperature for 15 hours. The reaction was partitioned between water (20 mL), and EtOAc (100 mL). The organic layer was dried over MgSO$_4$, filtered, and concentrated in vacuo. The resulting residue was purified by column chromatography on silica gel (5% MeOH/CH$_2$Cl$_2$ as eluant) to give 4-(4-Ethynyl-2-fluoro-phenylamino)-1-methyl-6-oxo- 1,6-dihydro-pyridine-3-carboxylic acid ethyl ester as a light brown solid (0.67 g, 88%). $^1$H NMR [(CDCl$_3$, 400 MHz] δ9.56 (s, 1H), 8.22 (s, 1H), 7.38 (dd, J=10.1, 1.9 Hz, 1H), 7.25 (s, 2H), 6.01 (s, 1H), 4.38 (q, J=7.1 Hz, 2H), 3.53 (s, 3H), 3.09 (s, 1H), 1.38 (t, J=7.1 Hz, 3H). Anal. Calcd for C$_{17}$H$_{15}$FlN$_2$O$_3$: C, 64.96; H, 4.81; N, 8.91. Found: C, 64.89; H, 4.40; N, 8.64.

EXAMPLE 74

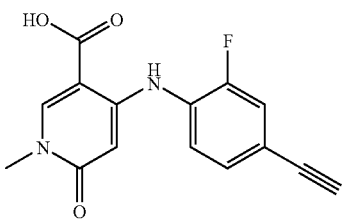

4-(4-Ethynyl-2-fluoro-phenylamino)-1-methyl-6-oxo-1,6-dihydro-pyridine-3-carboxylic acid 4-(4-Ethynyl-2-fluoro-phenylamino)-1-methyl-6-oxo-1,6-dihydro-pyridine-3-carboxylic acid ethyl ester (0.67 mg, 2.13 mmol) was suspended in EtOH (20 mL), to which was added NaOH (0.26 g, 6.40 mmol). This mixture was stirred at 70° C. for 1 hour. The solvent was removed under reduced pressure. The residue was acidified with 1N HCl then the resulting precipitate was filtered and washed with water. The tan solid was dried under high vacuum pump to afford 4-(4-Ethynyl-2-fluoro-phenylamino)-1-methyl-6-oxo-1,6-dihydro-pyridine-3-carboxylic acid (0.56 g, 91%). $^1$H NMR [(CD$_3$)$_2$SO, 400 MHz] δ 13.31 (v br s, 1H), 9.79 (s, 1H), 8.51 (s, 1H), 7.49 (dd, J=10.1, 1.9 Hz, 1H), 7.44 (dd, J=8.4, 1.7, 0.8 Hz, 1H), 7.32 (dd, J=8.5 Hz, 1H), 5.61 (dd, J=0.7 Hz, 1H), 4.25 (s, 1H), 3.41 (s, 3H). Anal. Calcd for C$_{15}$H$_{11}$FlN$_2$O$_3$: C, 62.94; H, 3.87; N, 9.79. Found: C, 62.56; H, 3.78; N, 9.30.

EXAMPLE 75

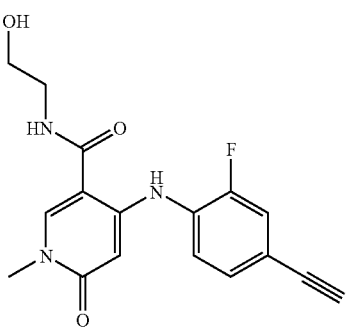

4-(4-Ethynyl-2-fluoro-phenylamino)-1-methyl-6-oxo-1,6-dihydro-pyridine-3-carboxylic acid (2-hydroxy-ethyl)-amide 4-(4-Ethynyl-2-fluoro-phenylamino)-1-methyl-6-oxo-1,6-dihydro-pyridine-3-carboxylic acid (0.70 g, 2.44 mmol) was reacted with pentafluorophenyl trifluoroacetate (1.30 mL, 7.36 mmol) in the presence of pyridine (0.60 mL) in DMF. The solution was allowed to stir at room temperature for 15 hours, to afford the 4-(4-Ethynyl-2-fluoro-phenylamino)-1-methyl-6-oxo-1,6-dihydro-pyridine-3-carboxylic acid pentafluorophenyl ester which was reacted directly with 2-aminoethanol (0.74 mL, 12.20 mmol) that is stirred at room temperature for 4 hours. The resulting precipitate was filtered and purified by column chromatography on silica gel (5% MeOH/CH$_2$Cl$_2$ as eluant) to give 4-(4-Ethynyl-2-fluoro-phenylamino)-1-methyl-6-oxo-1,6-dihydro-pyridine-3-carboxylic acid (2-hydroxy-ethyl)-amide as a yellow solid (0.24 g, 30%). $^1$H NMR [(CD$_3$)$_2$SO, 400 MHz] δ 10.27 (s, 1H), 8.41 (t, 1H), 8.13 (s, 1 H), 7.48 (dd, J=10.2, 1.8 Hz, 1H), 7.40 (dd, J=8.6 Hz, 1H), 7.31 (dd, J=8.5 Hz, 1H), 5.73 (s, 1H), 4.76 (t, 1 H, OH), 4.24 (s, 1H), 3.51 (t, J=4.9 Hz, 2H), 3.35 (s, 3H), 3.25 (t, J=8.3 Hz, 2H). (APCI$^+$) calcd for C$_{17}$H$_{16}$FN$_3$O$_3$ 329.33 (M+1), found 330.1.

EXAMPLE 76

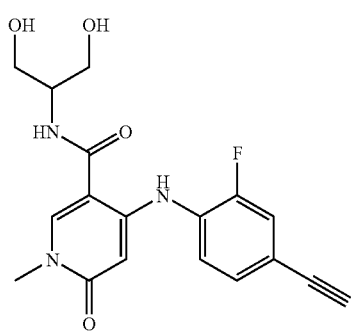

4-(4-Ethynyl-2-fluoro-phenylamino)-1-methyl-6-oxo-1,6-dihydro-pyridine-3-carboxylic acid (2-hydroxy-1-hydroxymethyl-ethyl)-amide 4-(4-Ethynyl-2-fluoro-phenylamino)-1-methyl-6-oxo-1,6-dihydro-pyridine-3-carboxylic acid was reacted with pentafluorophenyl trifluoroacetate in the presence of pyridine in DMF to afford the corresponding pentafluorophenyl ester which was reacted directly with 2-Amino-propane-1,3-diol as for Example 75. All solvent was removed from the reaction mixture under reduced pressure, and the resulting solid was purified by HPLC to afford 4-(4-Ethynyl-2-fluoro-phenylamino)-1-methyl-6-oxo-1,6-dihydro-pyridine-3-carboxylic acid (2-hydroxy-1-hydroxymethyl-ethyl)-amide as an off white solid (0.26 g, 30%). $^1$H NMR [(CD$_3$)$_2$SO, 400 MHz] δ 10.27 (s, 1H), 8.30 (s, 1H), 8.04 (s, 1H), 7.45 (dd, J=10.2, 1.8 Hz, 1H), 7.41 (dd, J=8.6 Hz, 1H), 7.35 (dd, J=8.5 Hz, 1H), 5.70 (s, 1H), 4.76 (v br s, 2 H, OH), 4.21 (s, 1H), 3.90 (m, 1H), 3.45 (br s, 3H), 3.38 (s, 3H), 2.44 (s, 2H). (APCI$^+$) calcd for C$_{18}$H$_{18}$FN$_3$O$_4$ 359.35 (M+1), found 360.1.

EXAMPLE 77

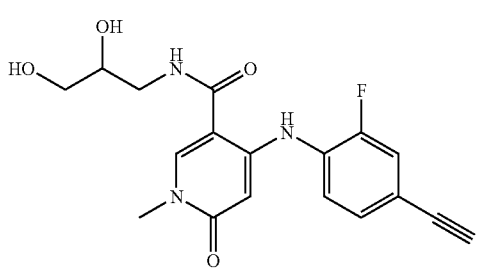

4-(4-Ethynyl-2-fluoro-phenylamino)-1-methyl-6-oxo-1,6-dihydro-pyridine-3-carboxylic acid (2,3-dihydroxy-propyl)-amide 4-(4-Ethynyl-2-fluoro-phenylamino)-1-methyl-6-oxo-1,6-dihydro-pyridine-3-carboxylic acid was reacted with pentafluorophenyl trifluoroacetate in the presence of pyridine in DMF, to afford the corresponding pentafluorophenyl ester which was reacted directly with 3-Amino-propane-1,2-diol as for Example 75. All solvent was removed from the reaction mixture under reduced pressure, and the resulting solid was purified by HPLC to afford 4-(4-Ethynyl-2-fluoro-phenylamino)-1-methyl-6-oxo-1,6-dihydro-pyridine-3-carboxylic acid (2,3-dihydroxy-propyl)-amide as an off white solid (0.210 g, 53%). $^1$H NMR [(CD$_3$)$_2$SO, 400 MHz] δ 10.24 (s, 1H), 8.38 (t, 1H), 8.30 (s, 1H), 7.51 (dd, J=10.2, 1.8 Hz, 1H), 7.42 (dd, J=8.6 Hz, 1H), 7.34 (dd, J=8.5 Hz, 1H), 5.68 (s, 1H), 4.76 (v br s, 2 H, OH), 4.22 (s, 1H), 3.58 (m, 1H), 3.35 (m, 7H), 3.08 (m, 1H), 2.42 (s, 1H). (APCI$^+$) calcd for C$_{18}$H$_{18}$FN$_3$O$_4$ 359.35 (M+1), found 360.1.

EXAMPLE 78

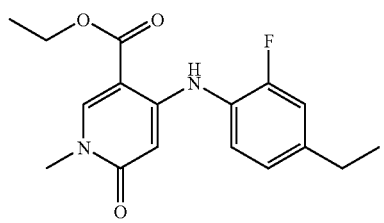

4-(4-Ethyl-2-fluoro-phenylamino)-1-methyl-6-oxo-1,6-dihydro-pyridine-3-carboxylic acid ethyl ester

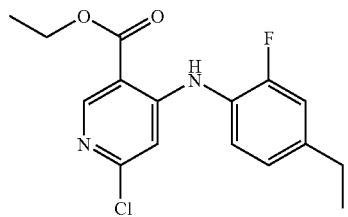

Step A: 6-Chloro-4-(4-ethyl-2-fluoro-phenylamino)-nicotinic acid ethyl ester

Ethyl 4,6-dichloronicotinate (31.62 g, 144.0 mmol) and 4-Ethyl-2-fluoro-phenylamine (20.0 g, 144.0 mmol) were dissolved in EtOH (200 mL), to which was added conc. HCl (6 drops) as for Example 1, alternate Step A to give 6-Chloro-4-(4-ethyl-2-fluoro-phenylamino)-nicotinic acid ethyl ester (46.50 g, 99%). (APCI$^+$) calcd for C$_{16}$H$_{18}$ClFN$_2$O$_2$ 322.76 (M−1), found 321.0.

Step B: 4-(4-Ethyl-2-fluoro-phenylamino)-1-methyl-6-oxo-1,6-dihydro-pyridine-3-carboxylic acid ethyl ester 6-Chloro-4-(4-ethyl-2-fluoro-phenylamino)-nicotinic acid ethyl ester (23.0 g, 72.0 mmol) was dissolved in CHCl$_3$ (200 mL) and the solution cooled (ice/water). Dimethyl sulfate (42.0 mL, 432.0 mmol) was added, the solution allowed to warm to room temperature then heated at reflux for 20 hours as in Example 1, alternate Step B to give 4-(4-Ethyl-2-fluoro-phenylamino)-1-methyl-6-oxo-1,6-dihydro-pyridine-3-carboxylic acid ethyl ester as a white solid (10.30 g, 45%). $^1$H NMR [(CDCl$_3$, 400 MHz] δ 9.17 (s, 1H), 8.19 (s, 1H), 7.23 (dd, J=10.1, 1.9 Hz, 1H), 6.99 (dd, J=8.3, 1.0 Hz, 1H), 6.94 (d, J=8.5 Hz, 1H), 5.76 (s, 1H), 4.33 (q, J=7.1 Hz, 2H), 3.52 (s, 3H), 2.64 (q, J=7.2 Hz, 2H), 1.39 (t, J=6.9 Hz, 3H), 1.23 (t, J=7.1 Hz, 3H). (APCI$^+$) calcd for C$_{17}$H$_{19}$FN$_2$O$_3$ 318.34 (M+1), found 319.1.

EXAMPLE 79

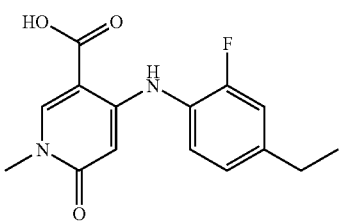

4-(4-Ethyl-2-fluoro-phenylamino)-1-methyl-6-oxo-1,6-dihydro-pyridine-3-carboxylic acid 4-(4-Ethyl-2-fluoro-phenylamino)-1-methyl-6-oxo-1,6-dihydro-pyridine-3-carboxylic acid ethyl ester (9.20 g, 28.90 mmol) was dissolved in EtOH (100 mL) and treated with NaOH (3.50 g, 86.70 mmol). This mixture was stirred at 90° C. for 2 hours to hydrolyze the ester as in Example 1, alternate Step C to give 4-(4-Ethyl-2-fluoro-phenylamino)-1-methyl-6-oxo-1,6-dihydro-pyridine-3-carboxylic acid as a white solid (8.30 g, 98%). $^1$H NMR [(CD$_3$)$_2$SO, 400 MHz] δ 13.21 (v br s, 1H), 9.41 (s, 1H), 8.49 (s, 1H), 7.35 (dd, J=10.1, 1.9 Hz, 1H), 7.19 (dd, J=8.4, 1.7, 0.8 Hz, 1H), 7.06 (dd, J=8.5 1.9 Hz, 1H), 5.33 (dd, J=0.7 Hz, 1H), 3.37 (s, 3H), 2.57 (q, J=7.2 Hz, 2H). 1.16 (t, J=7.1 Hz, 3H). (APCI$^+$) calcd for C$_{15}$H$_{15}$FN$_2$O$_3$ 290.29 (M+1), found 291.1.

EXAMPLE 80

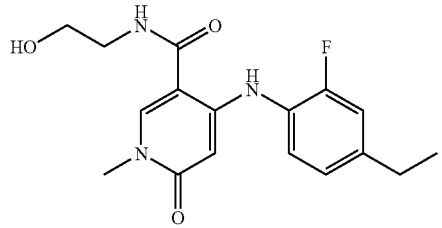

4-(4-Ethyl-2-fluoro-phenylamino)-1-methyl-6-oxo-1,6-dihydro-pyridine-3-carboxylic acid (2-hydroxy-ethyl)-amide 4-(4-Ethyl-2-fluoro-phenylamino)-1-methyl-6-oxo-1,6-dihydro-pyridine-3-carboxylic acid (0.50 g, 1.72 mmol) was reacted with pentafluorophenyl trifluoroacetate (0.92 mL, 5.20 mmol) in the presence of pyridine (0.45 mL) in DMF (15 mL). The solution was allowed to stir at room temperature for 15 hours and then treated with 2-Amino-ethanol (0.50 mL, 8.60 mmol) as in example 75 to afford the 4-(4-Ethyl-2-fluoro-phenylamino)-1-methyl-6-oxo-1,6-dihydro-pyridine-3-carboxylic acid (2-hydroxy-ethyl)-amide (0.47 g, 82%). $^1$H NMR [400 MHz, (CD$_3$)$_2$SO] δ 9.82 (s, 1H), 8.35 (t, J=5.4 Hz, 1H), 8.20 (s, 1H), 7.27 (t, J=8.4 Hz, 1H), 7.12 (d, J=11.8 Hz, 1H), 7.06 (d, J=7.7 Hz, 1H), 5.38 (s, 1H), 4.72 (t, J=5.1 Hz, 1 H, OH), 3.44 (t, J=11.5, 6.2 Hz, 2H), 3.35 (s, 3H), 3.22 (t, J=12.8, 6.8 Hz, 2H), 2.58 (q, J=7.1

Hz, 2H), 1.14 (t, J=7.1 Hz, 3H). (APCI⁺) calcd for $C_{17}H_{20}FN_3O_3$ 333.36 (M+1), found 334.1.

EXAMPLE 81

4-(4-Ethyl-2-fluoro-phenylamino)-6-oxo-1,6-dihydro-pyridine-3-carboxylic acid (2-hydroxy-1-hydroxymethyl-ethyl)-amide

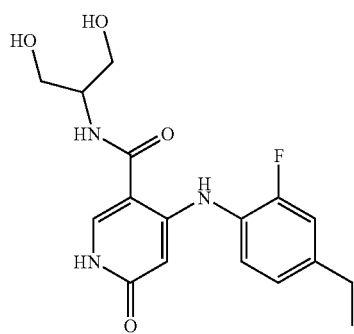

4-(4-Ethyl-2-fluoro-phenylamino)-1-methyl-6-oxo-1,6-dihydro-pyridine-3-carboxylic acid was reacted with pentafluorophenyl trifluoroacetate in the presence of pyridine in DMF to afford the corresponding pentafluorophenyl ester which was reacted directly with 2-Amino-propane-1,3-diol as for example 76 to afford 4-(4-Ethyl-2-fluoro-phenylamino)-6-oxo-1,6-dihydro-pyridine-3-carboxylic acid (2-hydroxy-1-hydroxymethyl-ethyl)-amide as an off white solid (0.51 g, 81%). ¹H NMR [(CD₃)₂SO, 400 MHz] δ 9.84 (s, 1H), 8.26 (s, 1H), 7.98 (d, J=7.8 Hz, 1H), 7.28 (dd, J=10.2, 1.8 Hz, 1H), 7.18 (dd, J=8.6 Hz, 1H), 7.04 (dd, J=8.5 Hz, 1H), 5.41 (s, 1H), 4.68 (t, 2H), 3.92 (m, 1H), 3.51 (m, 4H), 3.33 (s, 3H), 2.54 (q, J=7.1 Hz, 2H), 1.16 (t, J=7.1 Hz, 3H). (APCI⁺) calcd for $C_{18}H_{22}FN_3O_4$ 363.38 (M+1), found 364.1.

EXAMPLE 82

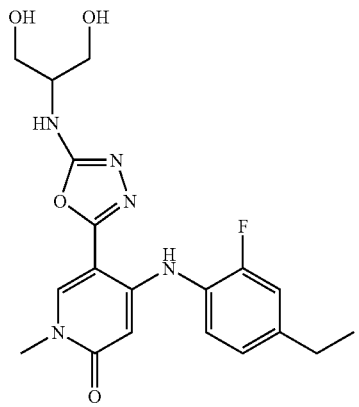

4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one

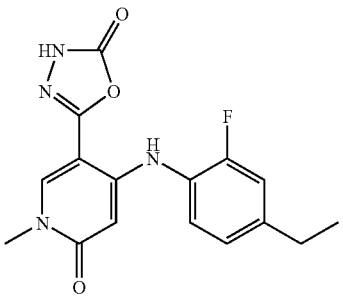

Step A: 4-(4-Ethyl-2-fluoro-phenylamino)-1-methyl-5-(5-oxo-4,5-dihydro-[1,3,4]oxadiazol-2-yl)-1H-pyridin-2-one The produce of Step A was prepared as described in Example 72.

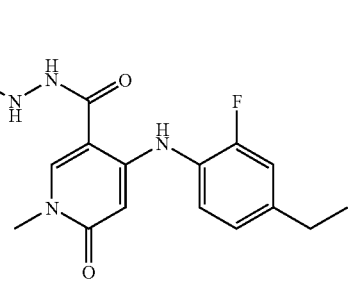

Step B: 4-(4-Ethyl-2-fluoro-phenylamino)-1-methyl-5-(5-oxo-4,5-dihydro-[1,3,4]oxadiazol-2-yl)-1H-pyridin-2-one (2.0 g, 6.05 mmol) was treated with the pyridine (15 mL) and 2-Amino-propane-1,3-diol (1.70 g, 18.16 mmol). The mixture was heated at 100° C. for 5 hours. After cooling, the reaction solvent was removed under reduced pressure and the resulting residue was purified by column chromatography on silica gel (10-50% MeOH/CH₂Cl₂ as eluant) to give product as brown oil (0.60 g, 23%). ¹H NMR [(CD₃)₂SO, 400 MHz] δ 8.91 (s, 1H), 8.03 (br s, 1H), 7.29 (d, J=7.8 Hz, 1H), 7.12 (dd, J=10.2, 1.8 Hz, 1H), 7.18 7.04 (d, J=8.5 Hz, 1H), 6.03 (br s, 1H), 5.36 (s, 1H), 4.12 (br s, 2H), 3.44 (m, 1H), 3.38 (m, 4H), 3.33 (s, 3H), 3.21 (m, 2H), 2.64 (q, J=7.1 Hz, 2H), (1.16 (t, J=7.1 Hz, 3H). (APCI⁺) calcd for $C_{19}H_{24}FN_5O_5$ 421.42 (M+1), found 422.1.

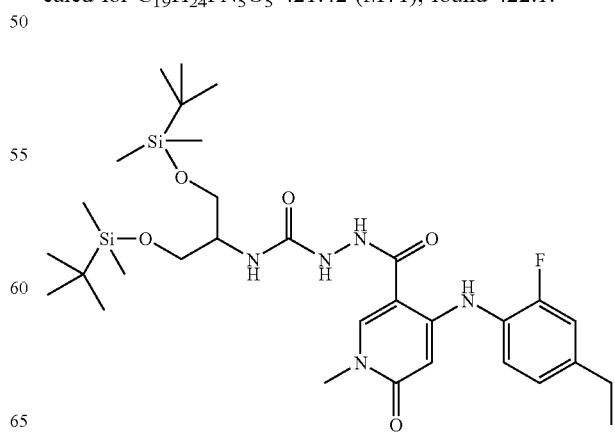

Step C: To the product of step B (0.60 g, 1.42 mmol) in DMF (10 mL) was added imidazole (0.40 g, 6.0 mmol) and tert-butyldimethylsilyl chloride (0.47 g, 3.13 mmol), which was stirred at RT for 48 hours. The reaction was diluted with EtOAc (100 mL), which was washed sequentially with water (100 mL), and brine (100 mL). The EtOAc fraction was then dried (MgSO$_4$) and the solvent removed under reduced pressure to yield a dark brown gummy-viscous oil (0.65 g, 70%). $^1$H NMR [(CD$_3$)$_2$SO, 400 MHz] δ 9.62 (br s, 1H), 8.38 (s, 1H), 8.0 (s, 1H), 7.29 (d, J=7.8 Hz, 1H), 7.12 (dd, J=10.2, 1.8 Hz, 1H), 7.18 7.04 (d, J=8.5 Hz, 1H), 6.03 (br s, 1H), 5.36 (s, 1H), 4.12 (br s, 2H), 3.44 (m, 1H), 3.38 (s, 1H), 3.33 (s, 3H), 3.21 (m, 2H), 2.67 (q, J=7.1 Hz, 2H), (1.21 (t, J=7.1 Hz, 3H), 0.89 (s, 18H), 0.07 (s, 12H). (APCI$^+$) calcd for C$_{31}$H$_{52}$FN$_5$O$_6$Si$_2$ 649.94 (M+1), found 650.3.

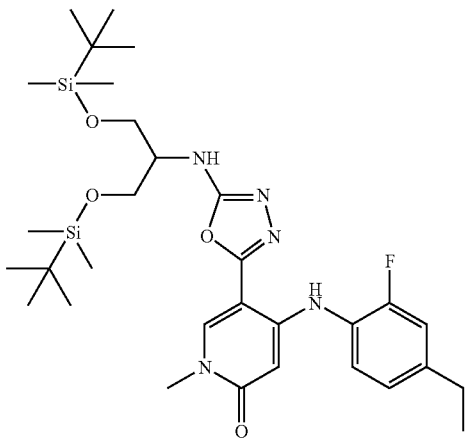

Step D: 5-{5-[2-(tert-Butyl-dimethyl-silanyloxy)-1-(tert-butyl-dimethyl-silanyloxymethyl)-ethylamino]-[1,3,4]oxadiazol-2-yl}-4-(4-ethyl-2-fluoro-phenylamino)-1-methyl-1H-pyridin-2-one To the product of step C (0.65 g, 1.0 mmol) in CH$_2$Cl$_2$ (10 mL) was added PS-triphenylphosphine (1.23 g, 2.70 mmol), Et$_3$N (0.30 mL, 2 mmol), and CCl$_4$ (0.20 mL, 2 mmol), which was stirred at 80° C. for 3 hours. After cooling, the resin was filtered out and washed with methanol (20 mL) and CH$_2$Cl$_2$ (20 mL). The filtrate was diluted with EtOAc (100 mL), which was washed sequentially with water (2×100 mL), and brine (100 mL). The EtOAc fraction was then dried (MgSO$_4$) and the solvent removed under reduced pressure to yield 5-{5-[2-(tert-Butyl-dimethyl-silanyloxy)-1-(tert-butyl-dimethyl-silanyloxymethyl)-ethylamino]-[1,3,4]oxadiazol-2-yl}-4-(4-ethyl-2-fluoro-phenylamino)-1-methyl-1H-pyridin-2-one as a dark brownish foam (0.41 g, 65%). $^1$H NMR [(CD$_3$)$_2$SO, 400 MHz] δ 9.1 (s, 1H), 8.85 (s, 1H), 7.85 (s, 1H), 7.35 (m, 3H), 7.05 (m, 2H), 5.86 (m, 1H), 3.95 (m, 2H), 3.80 (m, 2H), 3.60 (s, 3H), 2.70 (q, J=7.1 Hz, 2H), (1.30 (t, J=7.1 Hz, 3H), 0.97 (s, 18H), 0.06 (s, 12H). (APCI$^+$) calcd for C$_{31}$H$_{50}$FN$_5$O$_4$Si$_2$ 631.93 (M+1), found 632.3.

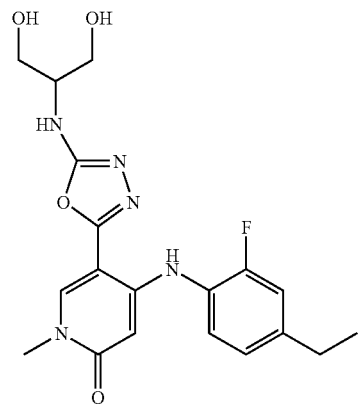

Step E: The product of step D (0.41 g, 0.65 mmol) in THF (15 mL) at 0° C. was added AcOH (0.040 mL, 0.65 mmol), tetrabutylammonium fluoride (1M in THF, 0.97 mL), which was stirred at 0° C. for 1 hour and R.T. for 5 hours. The reaction was diluted with EtOAc (50 mL), which was washed sequentially with NaHCO$_3$ (20 mL), 0.5 M HCl (20 mL), water (50 mL), and brine (50 mL). The EtOAc fraction was then dried (MgSO$_4$) and the solvent removed under reduced pressure. No product was present in the organic layer. The filtrate (aqueous layers) were combined and cooled to 0° C. An off white solid precipitate out, filtered and dried to yield 4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one (0.080 g, 30%). $^1$H NMR [(CD$_3$)$_2$SO, 400 MHz] δ 9.05 (s, 1H), 8.08 (s, 1H), 7.54 (d, 1H), 7.38 (dd, 1H), 7.21 (d, 1H), 7.09 (d, 1H), 5.43 (s, 1H), 4.72 (t, 1H), 3.50 (m, 5H), 3.40 (s, 3H), 2.60 (q, 2H), 1.18 (t, 3H). (APCI$^+$) calcd for C$_{19}$H$_{22}$FN5O4 403.1 (M+1), found 404.1.

EXAMPLE 83

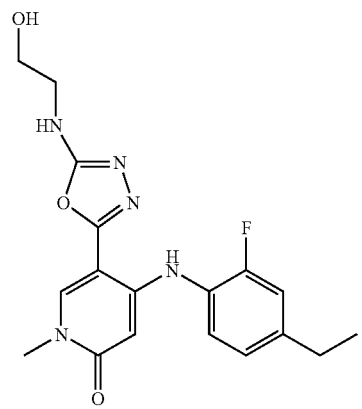

4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one The title compound was prepared as described in Example 82. The final product was obtained as an off white solid (0.38 g, 37%). $^1$H NMR [400 MHz, (CD$_3$)$_2$SO] δ 9.12 (s, 1H), 8.17 (s, 1H), 7.83 (t, J=5.4 Hz, 1H), 7.45 (t, J=8.4 Hz, 1H), 7.31 (d, J=11.8 Hz, 1H), 7.19 (d, J=7.7 Hz, 1H), 5.38 (s, 1H), 4.81 (br s, 1 H, OH), 3.62 (t, J=5.1 Hz, 2H), 3.47 (s, 3H), 3.35 (t, J=11.5, 6.2 Hz, 2H), 2.65 (q, J=7.1 Hz, 2H), 1.22 (t, J=7.1 Hz, 3H). (APCI$^+$) calcd for C$_{18}$H$_{20}$FN$_5$O$_3$ 373.38 (M+1), found 374.1.

EXAMPLE 84

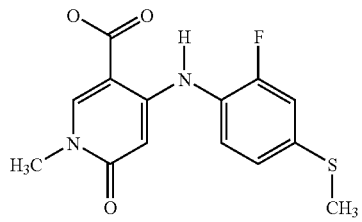

4-(2-Fluoro-4-methylsulfanyl-phenylamino)-1-methyl-6-oxo-1,6-dihydro-pyridine-3-carboxylic acid 4-(2-Fluoro-4-methylsulfanyl-phenylamino)-1-methyl-6-oxo-1,6-dihydro-pyridine-3-carboxyic acid was synthesized according to the procedure described in Example 1, alternate Steps A-C only employing 2-fluoro-3-thiomethyl aniline as starting material providing product 7.25 g (85%) as a light yellow solid $^1$H NMR [(CD$_3$)$_2$SO, 400 MHz δ13.22 (v br s, 1H), 9.43(s,1H), 8.47(s,1H), 7.39(t,1H),7.26(dd,1H), 7.13 (dd,1H), 5.33(s,1H), 3.38(s,3H), 2.48(s,3H); APCIMS calcd for C$_{14}$H$_{13}$N$_2$O$_3$S$_1$F$_1$ 308 (MH$^+$), Found 309.

EXAMPLE 85

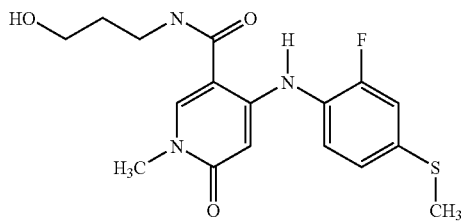

4-(2-Fluoro-4-methylsulfanyl-phenylamino)-1-methyl-6-oxo-1,6-dihydro-pyridine-3-carboxylic acid (3-hydroxypropyl)-amide 4-(2-Fluoro-4-methylsulfanyl-phenylamino)-1-methyl-6-oxo-1,6-dihydro-pyridine-3-carboxylic acid (3-hydroxypropyl)-amide was synthesized according to the procedure described in Example 1, alternate Steps A-C employing 2-fluoro-3-thiomethyl aniline as starting material and Example 71 employing 3-aminopropanol as starting material providing product 0.50 g (85%) as a colorless solid $^1$H NMR [(CD$_3$)$_2$SO, 400 MHz δ 9.89 (s,1H), 8.35(t,1H), 8.19(s,1H), 7.37(t,1H), 7.25(dd,1H), 7.08(dd,1H),5.40(s, 1H), 4.44(t,1H), 3.45(q,2H), 3.35(s,3H), 3.24(m,2H), 2.47 (s,3H), 1.64(m,2H); APCIMS calcd for C$_{17}$H$_{20}$N$_3$O$_3$S$_1$F$_1$ 365 (MH$^+$), Found 366.

EXAMPLE 86

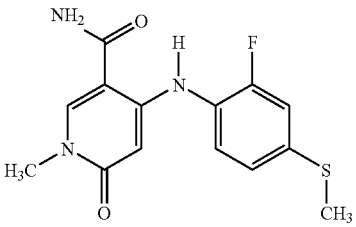

4-(2-Fluoro-4-methylsulfanyl-phenylamino)-1-methyl-6-oxo-1,6-dihydro-pyridine-3-carboxylic acid amide 4-(2-Fluoro-4-methylsulfanyl-phenylamino)-1-methyl-6-oxo-1,6-dihydro-pyridine-3-carboxylic acid amide was synthesized according to the procedure described in Example 1, alternate Steps A-C employing 2-fluoro-3-thiomethyl aniline as starting material and Example 71 employing ammonia as starting material providing product 0.24 g (47%) as a colorless solid $^1$H NMR [(CD$_3$)$_2$SO, 400 MHz δ 10.16(s, 1H), 8.36(s,1H), 7.80(v br s, 1H), 7.40(v br s,1H), 7.37(t, 1H), 7.25(dd,1H), 7.10(dd,1H), 5.38(s,1H), 3.33(s,3H), 2.46 (s,3H); APCIMS calcd for C$_{14}$H$_{14}$N$_3$O$_2$S$_1$F$_1$ 307 (MH$^+$), Found 308.

EXAMPLE 87

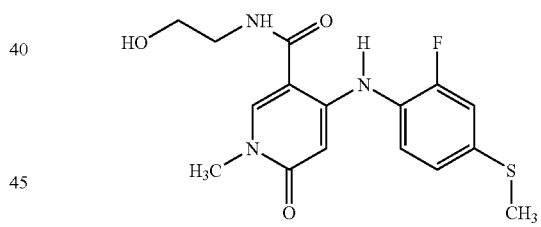

4-(2-Fluoro-4-methylsulfanyl-phenylamino)-1-methyl-6-oxo-1,6-dihydro-pyridine-3-carboxylic acid (2-hydroxyethyl)amide 4-(2-Fluoro-4-methylsulfanyl-phenylamino)-1-methyl-6-oxo-1,6-dihydro-pyridine-3-carboxylic acid (2-hydroxyethyl)amide was synthesized according to the procedure described in Example 1, alternate Steps A-C, employing 2-fluoro-3-thiomethyl aniline as starting material and Example 71 providing product 0.54 g (94%) as a colorless solid $^1$H NMR [(CD$_3$)$_2$SO, 400 MHz δ 9.88 (s,1H), 8.38(t, 1H), 8.24(s,1H), 7.7.35(t,1 h), 7.25(dd,1H), 7.10(dd,1H), 5.39(s,1H), 4.74(t,1H), 3.47(q,2H), 3.34(s,3H), 3.25(m,2H), 2.46(s,3H); APCIMS calcd for C$_{16}$H$_{18}$N$_3$O$_3$S$_1$F$_1$ 351 (MH$^+$), Found 352

EXAMPLE 88

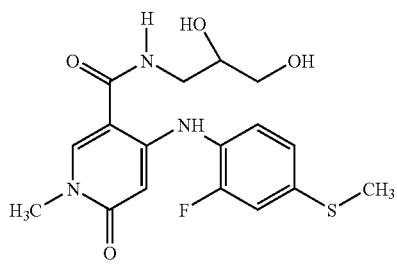

4-(2-Fluoro-4-methylsulfanyl-phenylamino)-1-methyl-6-oxo-1,6-dihydro-pyridine-3-carboxylic acid (2,3-dihydroxypropyl)-amide 4-(2-Fluoro-4-methylsulfanyl-phenylamino)-1-methyl-6-oxo-1,6-dihydro-pyridine-3-carboxylic acid (2,3-dihydroxypropyl)-amide was synthesized according to the procedure described in Example 1, alternate Step A-C employing 2-fluoro-3-thiomethyl aniline as starting material and Example 71 employing 2,3 dihydroxypropylamine providing product 0.43 g (70%) as a colorless solid $^1$H NMR [(CD$_3$)$_2$SO, 400 MHz δ 9.85(s,1H), 8.35(t,1H), 8.24(s,1H), 7.7.35(t,1H), 7.23(dd,1H), 7.08(dd,1H), 5.40(s,1H), 3.58(m, 2H), 3.37(m,2H), 3.35(s,3H), 3.05(m,1H), 2.45(s,3H); APCIMS calcd for C$_{17}$H$_{20}$N$_3$O$_4$S$_1$F$_1$ 381 (MH$^+$), Found 382

EXAMPLE 89

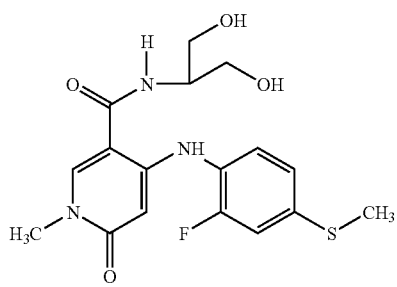

4-(2-Fluoro-4-methylsulfoanyl-phenylamino)-1-methyl-6-oxo-1,6, dihydro-pyridine-3-carboxylic acid (2-hydroxy-1-hydroxymethyl-ethyl)-amide 4-(2-Fluoro-4-methylsulfoanyl-phenylamino)-1-methyl-6-oxo-1,6, dihydro-pyridine-3-carboxylic acid (2-hydroxy-1-hydroxymethyl-ethyl)-amide was synthesized according to the procedure described in Example 1, alternate Steps A-C employing 2-fluoro-3-thiomethyl aniline as starting material and Example 71 employing 2-hydroxy-1-hydroxymethyl amine providing product 0.40 g (65%) as a colorless solid $^1$H NMR [(CD$_3$)$_2$SO, 400 MHz 9.50(s,1H), 8.24(s,1H), 7.97(d,1H), 7.35(t,1H), 7.25(dd,1H), 7.10(dd,1H), 5.41(s, 1H), 4.66(t,2H), 3.90(m,1H), 3.48(m,2H), 3.30(s,3H), 2.45 (s,3H); APCIMS calcd for C$_{17}$H$_{20}$N$_3$O$_4$S$_1$F$_1$ 381 (MH$^+$), Found 382.

EXAMPLE 90

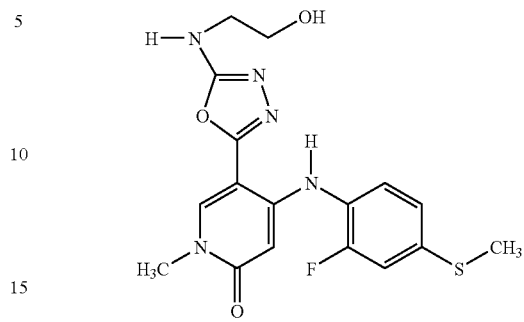

4-(2-Fluoro-4-methylsulfanyl-phenylamino)-5-[5-(2-hydroxy-ethylamino)[1,3,4]oxadiazol-2-yl]-1-methyl-1H-pyridin-2-one 4-(2-Fluoro-4-methylsulfanyl-phenylamino)-5-[5-(2-hydroxy-ethylamino)[1,3,4]oxadiazol-2-yl]-1-methyl-1H-pyridin-2-one was synthesized according to the procedure described in Examples 1, alternate Steps A-C, 71, 72 and 82 only employing 2-fluoro-3-thiomethyl aniline as starting material. The ethanolamine product of Example 82 was employed to provide the title product 0.20 g (80%) as a colorless solid $^1$H NMR [(CD$_3$)$_2$SO, 400 MHz 9.04(s,1H), 8.12(s,1H), 7.78(t,1H), 7.30(dd,1H), 7.13(dd,1H), 5.43(s, 1H), 4.76(t,1H), 3.55(q,2H), 3.30(s,3H), 3.27(q,2H), 2.50(s, 3H); APCIMS calcd for C$_{17}$H$_{18}$N$_5$O$_3$S$_1$F$_1$ 391 (MH$^+$), Found 392.

EXAMPLE 91

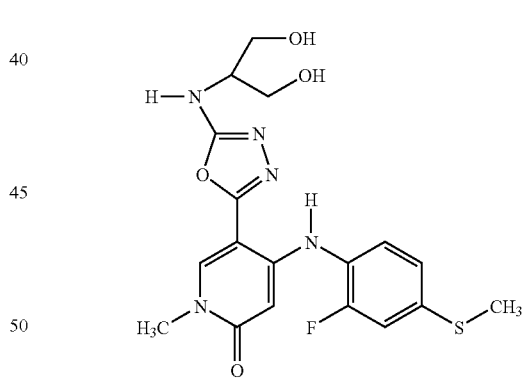

4-(2-Fluoro-4-methylsulfanyl-phenylamino)-5-[5-(2-hydroxy-1-hydroxymethyl-ethylamino)-[1,3,4]oxadiazol-2-yl]-1-methyl-1H-pyridin-2-one 4-(2-Fluoro-4-methylsulfanyl-phenylamino)-5-[5-(2-hydroxy-1-hydroxymethyl-ethylamino)-[1,3,4]oxadiazol-2-yl]-1-methyl-1H-pyridin-2-one was synthesized according to the procedure described in Examples 1, alternate steps A-C, 71, 72 and 82 only employing 2-fluoro-3-thiomethyl aniline as starting material. The 2-hydroxy-1-hydroxymethyl-ethyl amine product of Example 82 step B was employed to provide the title product 0.15 g (71%) as a colorless solid $^1$H NMR [(CD$_3$)$_2$SO, 400 MHz 9.03(s,1H), 8.07(s,1H),7.58(d,1H), 7.39(t,1H), 7.26(dd,1H), 7.10(dd, 1H), 5.40(s,1H), 4.70(t,2H), 3.50(m, 5H), 3.27(s,3H), 2.47 (s,3H); APCIMS calcd for $C_{18}H_{20}N_5O_4S_1F_1$ 421 (MH+), Found 422.

EXAMPLE 92

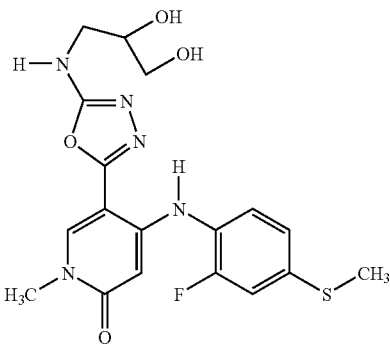

5-[5-(2,3-dihydroxy-propylamino)-[1,3,4]oxadiazol-2-yl]-4-(2-fluoro-4-methylsulfanyl-phenylamino)-1-methyl-1H-pyridine-2-one 5-[5-(2,3-dihydroxy-propylamino)-[1,3,4]oxadiazol-2-yl]-4-(2-fluoro-4-methylsulfanyl-phenylamino)-1-methyl-1H-pyridine-2-one was synthesized according to the procedure described in Examples 1, alternate steps A-C, 71, 72 and 82 only employing 2-fluoro-3-thiomethyl aniline as starting material. The 2,3-dihydroxy-propylamine of Example 82 was employed to provide the title product 0.415 g (56%) as a colorless solid $^1$H NMR [(CD$_3$)$_2$SO, 400 MHz 9.05(S,1H), 8.12(s,1H), 7.72(t,1H), 7.41(t,1H), 7.30(dd,1H), 7.15(dd,1H), 5.44(s,1H), 4.82(d,1H), 4.59(t,1H), 3.64(m, 1H), 3.41(s,3H), 3.35(m,2H), 3.15(m,1H), 2.50(s,3H); APCIMS calcd for $C_{18}H_{20}N_5O_4S_1F_1$ 421 (MH+), Found 422.

EXAMPLE 93

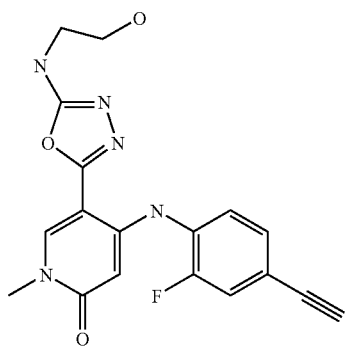

4-(4-Ethylnyl-2-fluoro-phenylamino)-5-[5-(2-hydroxy-ethylamino)-[1,3,4]oxadiazol-2-yl]-1-methyl-1H-pyridin-2-one 4-(4-Ethylnyl-2-fluoro-phenylamino)-5-[5-(2-hydroxy-ethylamino)-[1,3,4]oxadiazol-2-yl]-1-methyl-1H-pyridin-2-one was synthesized according to the procedure described in Examples 1, alternate steps A-C, 71, 72 and 82. The ethanolamine of Example 82 was employed to provide the title product 0.161 g (61%) as a colorless solid $^1$H NMR [(CD$_3$)$_2$SO, 400 MHz 9.36(s,1H), 8.15(s,1H), 7.80(t,1 h), 7.55(t, 1H), 7.50(dd,1H), 7.35(dd,1H), 5.72(s,1H), 4.26(2.1H), 3.55 (q,2H), 3.42(s,3H), 3.30(m,2H); APCIMS calcd for $C_{18}H_{16}N_5O_3F_1$ 369 (MH+), Found 370.

EXAMPLE 94

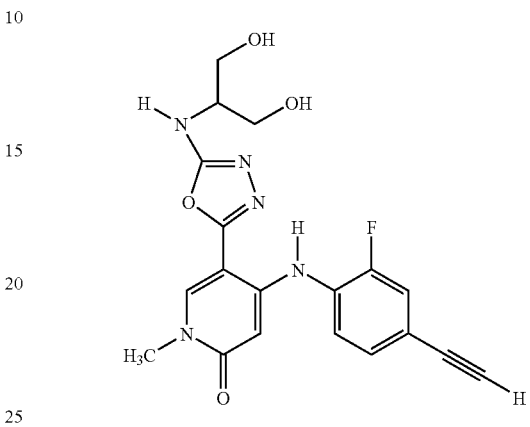

4-(4-Ethynyl-2-fluoro-phenylamino)-5-[5-(2-hydroxy-1-hydroxymethyl-ethylamino)-[1,3,4]oxadiazol-2-yl]-1-methyl-1H-pyridin2-one 4-(4-Ethynyl-2-fluoro-phenylamino)-5-[5-(2-hydroxy-1-hydroxymethyl-ethylamino)-[1,3,4]oxadiazol-2-yl]-1-methyl-1H-pyridin2-one was synthesized according to the procedure described in Examples 1, alternate steps A-C, 71, 72 and 82. The 2-hydroxy-1-hydroxymethyl-ethylamine of Example 82 was employed to provide the title product 0.102 g (64%) as a colorless solid $^1$H NMR [(CD$_3$)$_2$SO, 400 MHz 9.38(s,1H), 8.13(s,1H), 7.65(m,1H), 7.53(m,2H), 7.35(d, 1H), 5.73(s,1H), 4.75(brs, 2H), 4.30(s,1H), 3.50(m,4H), 3.42(s,3H), 3.12(s,1H); APCIMS calcd for $C_{19}H_{18}N_5O_4F_1$ 399 (MH+), Found 400.

EXAMPLE 95

Cellular Assay Measuring MEK Inhibition

MEK inhibitors were evaluated by determining their ability to inhibit phosphorylation of MAP kinase (ERK) in murine colon 26 (C26) carcinoma cells. Since ERK1 and ERK2 represent the only known substrates for MEK1and MEK2, the measurement of inhibition of ERK phosphorylation in cells provides direct read out of cellular MEK inhibition by the compounds of the invention. Detection of phosphorylation of ERK was carried out either by Western blot or ELISA format. Briefly, the assays involve treatment of exponentially growing C26 cells with varying concentrations of the test compound (or vehicle control) for one hour at 37° C. For Western blot assay, cells were rinsed free of compound/vehicle and lysed in a solution containing 70 mM NaCl, 50 mM glycerol phosphate, 10 mM HEPES, pH 7.4, 1% Triton X-100, 1 mM Na$_3$VO$_4$, 100 µM PMSF, 10 µM leupeptin and 10 µM pepstatin. Supernatants were then subjected to gel electrophoresis and hybridized to a primary antibody recognizing dually phosphorylated ERK1 and ERK2. To evaluate total MAPK levels, blots were subsequently 'stripped' and re-probed with a 1:1 mixture of polyclonal antibodies recognizing unphosphorylated ERK1 and ERK2. For pERK ELISA assay, pERK TiterZyme Enzyme immunometric Assay kits were acquired from Assay Designs, Inc (Ann Arbor, Mich.). Briefly, cells were harvested in lysis solution containing 50 mM β-glycerophosphate, 10 mM HEPES, ph7.4, 70 mM NaCl, 2 mM EDTA and 1% SDS and protein lysates were diluted 1:15 with supplied Assay buffer prior to the execution of the assay. The subsequent steps were carried out essentially as recommended by the manufacturer.

The inhibition data generated by the above protocols is disclosed in Table I. If several concentrations of inhibitor were tested, $IC_{50}$ values (the concentration which gives 50% inhibition) were determined graphically from the dose response curve for % inhibition. Otherwise, percent inhibitions at measured concentrations are reported.

TABLE I

Cellular Inhibition of ERK Phosphorylation by Compounds of the Invention

| Updated Example No(s) | C26CPA1 $IC_{50}$ (mM) | C26ELSA $IC_{50}$ (mM) |
| --- | --- | --- |
| 1 | 0.0438 | 0.0049 |
| 5 | 0.06 | 0.095 |
| 7 | | 5 |
| 9 | | 5 |
| 10 | | 0.0044 |
| 11 | | 5 |
| 14 | | 5 |
| 17 | | 0.021 |
| 19 | | 0.11 |
| 21 | | 0.63 |
| 24 | | 5 |
| 30 | | 0.43 |
| 31 | 1.41 | |
| 37 | | 5 |
| 40 | | 0.12 |
| 42 | | 0.093 |
| 47 | | 5 |
| 48 | | 5 |
| 51 | | 5 |
| 57 | | 5 |
| 58 | | 3.9 |
| 67 | 0.076 | |
| 85 | | 0.15 |
| 89 | 2.815 | |
| 90 | | >5 |
| 91 | | >1 |
| 92 | | 1.24 |

EXAMPLE 96

Carrageenan-induced Footpad Edema (CFE) Rat Model

Male outbred Wistar rats (135-150 g, Charles River Labs) are dosed orally with 10 mL/kg vehicle or test compound 1 hour prior to administration of a sonicated suspension of carrageenan (1 mg/0.1 mL saline). Carrageenan is injected into the subplantar region of the right hind paw. Paw volume is determined by mercury plethysmography immediately after injection and again five hours after carrageenan injection. Percent inhibition of edema is determined, and the ID40 calculated by linear regression. Differences in swelling compared to control animals are assessed by a 1-way ANOVA, followed by Dunnett's test.

EXAMPLE 97

Collagen-induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 μg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

EXAMPLE 98

SCW-induced Monoarticular Arthritis

Arthritis is induced as described by Schwab et al., *Infection and Immunity*, 1991;59:4436-4442 with minor modifications. Rats receive 6 μg sonicated SCW [in 10 μL Dulbecco's PBS (DPBS)] by an intraarticular injection into the right tibiotalar joint on Day 0. On Day 21, the DTH is initiated with 100 μg of SCW (250 μL) administered IV. For oral compound studies, compounds are suspended in vehicle (0.5% hydroxypropyl-methylcellulose/0.2% Tween 80), sonicated, and administered twice daily (10 mL/kg volume) beginning 1 hour prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on Day 21, and comparing them with volumes at subsequent time points such as Day 22, 23, 24, and 25. Paw volume is determined by mercury plethysmography.

EXAMPLE 99

Mouse Ear-heart Transplant Model

Fey, T. A., et al. describe methods for transplanting split-heart neonatal cardiac grafts into the ear pinna of mice and rats (*J. Pharm. and Toxic. Meth.*, 1998, 39:9-17). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (Day 0) through Day 13 or until grafts have been rejected. Rats are dosed once, twice, or three times daily from Day 0 through Day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10- to 20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1 to 4 times a day for 10, 20, 30 or more days. The ability of a test compound to ameliorate symptoms of transplant rejection can be compared with a control compound such as cyclosporine, tacrolimus, or orally-administered lefluonomide.

EXAMPLE 100

The analgesic activity of the compounds of the present invention is assessed by a test with rats. Rats weighing from 175 to 200 g are injected with carrageenan (2% in 0.9% sodium chloride aqueous solution, 100 μL injection volume) into the footpad of one hind limb. The rats are placed on a glass plate with illumination from a halogen lamp placed directly under the injected paw. The time (in seconds) from beginning illumination until the hindlimb was withdrawn from the glass was measured and scored as Paw Withdrawal Latency (PWL). Drug substances were given by oral gavage injection 2½ hours after carrageenan injection to the footpad. PWL was measured prior to carrageenan injection, just prior to drug injection, and 1, 2 (and sometimes 3) hours after drug injection.

Carrageenan (a polysaccharide extracted from seaweed) causes a sterile inflammation when injected under the skin. Injection into the rat footpad causes little or no spontaneous pain-related behavior but induces hyperalgesia (pain-related behavioral responses of greater intensity than expected) to peripheral thermal or mechanical stimuli. This hyperalgesia is maximal 2 to 3 hours after injection. Treatment of rats with various analgesic drugs reduces hyperalgesia measured in this way and is a conventional test for detection of analgesic activity in rats. (Hargreaves K, Dubner R, Brown F, Flores C, Joris J. A new and sensitive method for measuring thermal nociception in cutaneous hyperalgesia. *Pain*, 1988;32:77-88 and Kayser V, Guilbaud G. Local and remote modifications of nociceptive sensitivity during carrageenan-induced inflammation in the rat. *Pain*, 1987;28: 99-108). Untreated rats have a PWL of approximately 10 seconds. Carrageenan injection reduces PWL to approximately 3 seconds for at least 4 hours, indicating thermal hyperalgesia. Inhibition of the carrageenan thermal hyperalgesia response is determined by the difference between reduced PWL prior to drug and subsequent to drug treatment, and was expressed as percent inhibition of the response. Administration of MEK inhibitors dose-dependently reduced thermal hyperalgesia.

What is claimed is:
1. A compound of Formula I

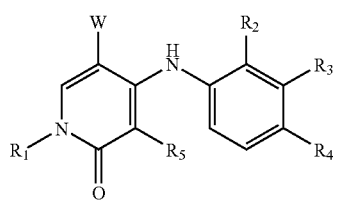

I wherein
W is

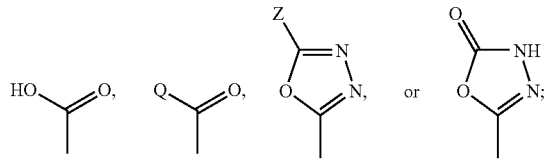

Q is —O—$(CH_2)_k CH_3$, —$NH_2$, —$NH[(CH_2)_k CH_3]$, or —$NH[O(CH_2)_k CH_3]$, wherein the —$NH_2$ is optionally substituted with between 1 and 2 substituents independently selected from methyl and amino, and the —$(CH_2)_k CH_3$ moieties of the —O—$(CH_2)_k CH_3$, —NH$[(CH_2)_k CH_3]$, and —$NH[O(CH_2)_k CH_3]$ groups are optionally substituted with between 1 and 3 substituents independently selected from hydroxy, amino, alkyl and cycloalkyl;

Z is —$NH_2$, —$NH[(CH_2)_k CH_3]$, or —$NH[O(CH_2)_k CH_3]$, wherein the —$NH_2$ is optionally substituted with between 1 and 2 substituents independently selected from methyl and amino, and the —$(CH_2)_k CH_3$ moieties of the —$NH[(CH_2)_k CH_3]$, and —$NH[O(CH_2)_k CH_3]$ groups are optionally substituted with between 1 and 3 substituents independently selected from hydroxy and amino;

$R_1$ is hydrogen, $C_{1-6}$ alkyl, $C_{2-4}$ alkenyl or —$(CH_2)_k O(CH_2)_k OCH_3$, wherein the $C_{1-6}$ alkyl is optionally substituted with between 1 and 2 substituents independently selected from hydroxy, —COOH, and cyano;

$R_2$ is hydrogen, chlorine, fluorine or methyl;

$R_3$ is hydrogen, chlorine, fluorine, methyl, or $CF_3$;

$R_4$ is bromine, chlorine, fluorine, iodine, $C_{1-6}$ alkyl, $C_{2-4}$ alkenyl, $C_{2-6}$ alkynyl, $C_{3-6}$ cycloalkyl, —$(CH_2)$—$C_{3-6}$ cycloalkyl, cyano, —O—$(C_{1-4}$ alkyl), —S—$(C_{1-2}$ alkyl), —$SOCH_3$, —$SO_2 CH_3$, —$SO_2 NR_6 R_7$, —C≡C—$(CH_2)_n NH_2$, —C≡C—$(CH_2)_n NHCH_3$, —C≡C—$(CH_2)_n N(CH_3)_2$, —C≡C—$CH_2 OCH_3$, —C=C$(CH_2)_n OH$, —C=C—$(CH_2)_n NH_2$, —$CHCHCH_2 OCH_3$, —CHCH—$(CH_2)_n NHCH_3$, —CHCH—$(CH_2)_n N(CH_3)_2$, —$(CH_2)_p CO_2 R_6$, C(O)$C_{1-3}$ alkyl, C(O)$NHCH_3$, —$(CH_2)_m NH_2$, —$(CH_2)_m NHCH_3$, —$(CH_2)_m N(CH_3)_2$, —$(CH_2)_m OR_8$, —$CH_2 S(CH_2)_t (CH_3)$, —$(CH_2)_p CF_3$, —C≡CCF$_3$, —CH=CHCF$_3$, —$CH_2 CHCF_2$, —CH=CF$_2$, —(CF$_2)_v CF_3$, —$CH_2 (CF_2)_n CF_3$, —$(CH_2)_t CF(CF_3)_2$, —CH(CF$_3)_2$, —CF$_2 CF(CF_3)_2$, or —C(CF$_3)_3$, wherein the $C_{1-6}$ alkyl and $C_{2-6}$ alkynyl are optionally substituted with between 1 and 3 substituents independently selected from hydroxy and alkyl; or $R_3$ and $R_4$ can be joined together to form a six-membered aryl ring, five-membered cycloalkyl ring or a five or six-membered heteroaryl ring;

$R_5$ is hydrogen, chlorine, fluorine, or methyl;

$R_6$ and $R_7$ are each independently hydrogen, methyl, or ethyl;

k is 0 to 3;
m is 1 to 4;
n is 1 to 2;
p is 0 to 2;
t is 0 to 1;
v is 1 to 5;

or pharmaceutically acceptable salts, $C_{1-6}$ amides or $C_{1-6}$ esters thereof.

2. A compound of claim 1 having the structure

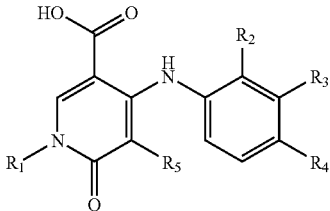

wherein $R_1$, $R_2$, $R_3$, $R_4$, and $R_5$ are defined as above.

3. A compound of claim 1 having the structure

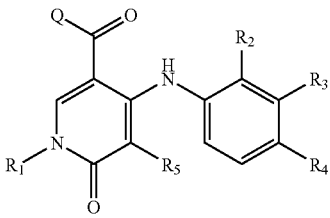

wherein Q, $R_1$, $R_2$, $R_3$, $R_4$, and $R_5$ are defined as above.

4. A compound of claim 3, wherein Q is —OCH$_2$CH$_3$, —NH$_2$, —NHCH$_3$, —N(CH$_3$)$_2$, —NHNH$_2$, —N(H)(CH$_2$)$_3$NH$_2$, —N(H)(CH$_2$)$_k$OH, —N(H)O(CH$_2$)$_2$OH, —N(H)CH$_2$CH(OH)CH$_2$OH, —N(H)CH(CH$_2$OH)$_2$, —N(H)C(CH$_2$OH)$_3$, —OCH$_2$C(NH$_2$)(CH$_2$OH)$_2$, —N(H)CH(CH$_2$OH)(CH$_3$), or —N(H)CH$_2$CH(CH$_3$)(OH).

5. A compound of claim 3, wherein Q is —NH$_2$ or —NH[O(CH$_2$)$_k$CH$_3$], wherein the —NH[O(CH$_2$)$_k$CH$_3$] is optionally substituted with between 1 and 3 hydroxy substituents.

6. A compound of claim 1 having the structure

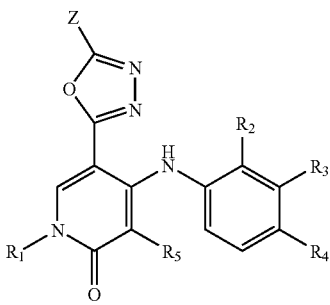

wherein Z, $R_1$, $R_2$, $R_3$, $R_4$, and $R_5$ are defined as above.

7. The compound of claim 6 wherein

Z is —N(H)(CH$_2$)$_2$OH, —N(H)CH(CH$_2$OH)$_2$, or —N(H)CH$_2$CH(OH)CH$_2$OH.

8. A compound of claim 1 having Formula

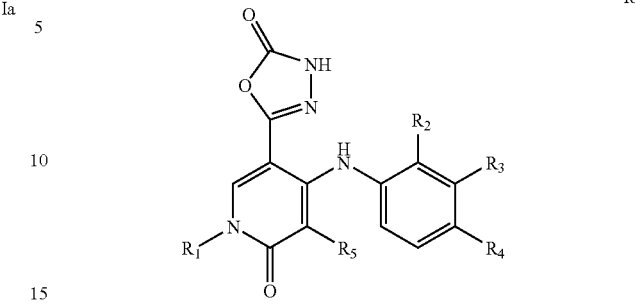

wherein $R_1$, $R_2$, $R_3$, $R_4$, and $R_5$ are defined as above.

9. The compound of claim 1 wherein $R_1$ is hydrogen, $C_{1-3}$ alkyl, —(CH$_2$)$_2$OH, —CH$_2$COOH, —(CH$_2$)$_3$CN, —(CH$_2$)$_2$O(CH$_2$)$_2$OCH$_3$, CH$_2$—CH=CH, CH$_2$CH(OH)CH$_2$OH, (CH$_2$)$_3$OH.

10. The compound of claim 1 wherein $R_2$ is hydrogen, chlorine, or fluorine.

11. The compound of claim 1 wherein $R_3$ is hydrogen, chlorine, methyl, or CF$_3$.

12. The compound of claim 1 wherein $R_4$ is bromine, chlorine, fluorine, iodine, $C_{1-3}$ alkyl, $C_{2-3}$ alkynyl, cyano, —S—CH$_3$, —SOCH$_3$, —(CF$_2$)$_3$CF$_3$, wherein the $C_{1-3}$ alkyl and $C_{2-3}$ alkynyl are optionally substituted with hydroxy; or $R_3$ and $R_4$ can be joined together to form a five-membered cycloalkyl ring, five-membered heteroaromatic ring, or six-membered aromatic ring.

13. The compound of claim 1 wherein $R_4$ is iodine, $C_{1-3}$ alkyl, $C_{2-3}$ alkynyl or S—CH$_3$.

14. The compound of claim 1 wherein $R_4$ is iodine, ethyl, allyl or S—CH$_3$.

15. The compound of claim 1 wherein $R_5$ is hydrogen.

16. A pharmaceutical composition comprising a compound of claim 1 and a pharmaceutically acceptable carrier.

17. A compound of claim 1 which is 4-(2-Fluoro-4-iodoanilino)-N-(2-hydroxyethoxy)-1-methyl-6-oxo-1,6-dihydro-3-pyridinecarboxamide;

4-[2-Fluoro-4-(3-hydroxy-1-propynyl)anilino]-N-(2-hydroxyethoxy)-1-methyl-6-oxo-1,6-dihydro-3-pyridinecarboxamide;

4-[2-Fluoro-4-(3-hydroxypropyl)anilino]-N-(2-hydroxyethoxy)-1-methyl-6-oxo-1,6-dihydro-3-pyridinecarboxamide;

4-(2-Fluoro-4-iodoanilino)-N-(2-hydroxyethyl)-1-methyl-6-oxo-1,6-dihydro-3-pyridinecarboxamide;

4-(2-Fluoro-4-iodoanilino)-N-(3-hydroxypropyl)-1-methyl-6-oxo-1,6-dihydro-3-pyridinecarboxamide;

4-[2-Fluoro-4-(3-hydroxy-1-propynyl)anilino]-N-(2-hydroxyethyl)-1-methyl-6-oxo-1,6-dihydro-3-pyridinecarboxamide;

4-[2-Fluoro-4-(3-hydroxypropyl)anilino]-N-(2-hydroxyethyl)-1-methyl-6-oxo-1,6-dihydro-3-pyridinecarboxamide;

4-[2-Fluoro-4-(3-hydroxy-1-propynyl)anilino]-N-(3-hydroxypropyl)-1-methyl-6-oxo-1,6-dihydro-3-pyridinecarboxamide;

4-[2-Fluoro-4-(3-hydroxypropyl)anilino]-N-(3-hydroxypropyl)-1-methyl-6-oxo-1,6-dihydro-3-pyridinecarboxamide;

4-(2-Fluoro-4-iodoanilino)-1-methyl-6-oxo-1,6-dihydro-3-pyridinecarboxamide;

4-(2-Fluoro-4-iodoanilino)-N-(2-hydroxyethyl)-6-oxo-1,6-dihydro-3-pyridinecarboxamide;
4-(4-Ethynyl-2-fluoroanilino)-N-(2-hydroxyethyl)-6-oxo-1,6-dihydro-3-pyridinecarboxamide;
4-(4-Ethyl-2-fluoroanilino)-N-(2-hydroxyethyl)-6-oxo-1,6-dihydro-3-pyridinecarboxamide;
4-(2-Fluoro-4-iodoanilino)-N-(3-hydroxypropyl)-6-oxo-1,6-dihydro-3-pyridinecarboxamide;
4-(4-Ethynyl-2-fluoroanilino)-N-(3-hydroxypropyl)-6-oxo-1,6-dihydro-3-pyridinecarboxamide;
4-(4-Ethyl-2-fluoroanilino)-N-(3-hydroxypropyl)-6-oxo-1,6-dihydro-3-pyridinecarboxamide;
4-(4-Ethynyl-2-fluoroanilino)-1-methyl-6-oxo-1,6-dihydro-3-pyridinecarboxamide;
4-(4-Ethyl-2-fluoroanilino)-1-methyl-6-oxo-1,6-dihydro-3-pyridinecarboxamide;
4-(2-Fluoro-4-iodoanilino)-6-oxo-1,6-dihydro-3-pyridinecarboxamide;
4-[2-Fluoro-4-(3-hydroxy-1-propynyl)anilino]-1-methyl-6-oxo-1,6-dihydro-3-pyridinecarboxamide;
4-[2-Fluoro-4-(3-hydroxypropyl)anilino]-1-methyl-6-oxo-1,6-dihydro-3-pyridinecarboxamide;
4-(2-Fluoro-4-iodoanilino)-1-(2-hydroxyethyl)-6-oxo-1,6-dihydro-3-pyridinecarboxamide;
4-(2-Fluoro-4-iodoanilino)-1-(2-hydroxyethyl)-N-(3-hydroxypropyl)-6-oxo-1,6-dihydro-3-pyridinecarboxamide;
(4-(2-Fluoro-4-iodoanilino)-5-{[(3-hydroxypropyl)amino]carbonyl}-2-oxo-1(2H)-pyridinyl)acetic acid;
5-(Aminocarbonyl)-4-(2-fluoro-4-iodoanilino)-2-oxo-1(2H)-pyridinyl)acetic acid;
1-(3-Cyanopropyl)-4-(2-fluoro-4-iodoanilino)-6-oxo-1,6-dihydro-3-pyridinecarboxamide;
1-Ethyl-4-(2-fluoro-4-iodoanilino)-6-oxo-1,6-dihydro-3-pyridinecarboxamide;
4-(2-Fluoro-4-iodoanilino)-6-oxo-1-propyl-1,6-dihydro-3-pyridinecarboxamide;
4-(2-Fluoro-4-iodoanilino)-1-[2-(2-methoxyethoxy)ethyl]-6-oxo-1,6-dihydro-3-pyridinecarboxamide;
1-Allyl-4-(2-fluoro-4-iodoanilino)-6-oxo-1,6-dihydro-3-pyridinecarboxamide;
1-(2,3-Dihydroxypropyl)-4-(2-fluoro-4-iodoanilino)-6-oxo-1,6-dihydro-3-pyridinecarboxamide;
4-(2-Fluoro-4-iodoanilino)-1-(3-hydroxypropyl)-6-oxo-1,6-dihydro-3-pyridinecarboxamide;
4-(2,4-Difluoroanilino)-N-(2-hydroxyethoxy)-1-methyl-6-oxo-1,6-dihydro-3-pyridinecarboxamide;
4-(2,4-Difluoroanilino)-N-(3-hydroxypropyl)-1-methyl-6-oxo-1,6-dihydro-3-pyridinecarboxamide;
4-(2-Fluoro-4-methylanilino)-N-(2-hydroxyethoxy)-1-methyl-6-oxo-1,6-dihydro-3-pyridinecarboxamide;
4-(2-Fluoro-4-methylanilino)-N-(3-hydroxypropyl)-1-methyl-6-oxo-1,6-dihydro-3-pyridinecarboxamide;
4-(2-Fluoro-4-methylanilino)-1-methyl-6-oxo-1,6-dihydro-3-pyridinecarboxamide;
4-(4-Bromo-2-fluoroanilino)-N-(2-hydroxyethoxy)-1-methyl-6-oxo-1,6-dihydro-3-pyridinecarboxamide;
4-(4-Bromo-2-fluoroanilino)-N-(3-hydroxypropyl)-1-methyl-6-oxo-1,6-dihydro-3-pyridinecarboxamide;
4-(4-Bromo-2-fluoroanilino)-1-methyl-6-oxo-1,6-dihydro-3-pyridinecarboxamide;
4-[2-Fluoro-4-(1,1,2,2,3,3,4,4,4-nonafluorobutyl)anilino]-1-methyl-6-oxo-1,6-dihydro-3-pyridinecarboxamide;
N-(3-Hydroxypropyl)-1-methyl-4-(2-naphthylamino)-6-oxo-1,6-dihydro-3-pyridinecarboxamide;
1-Methyl-4-(2-naphthylamino)-6-oxo-1,6-dihydro-3-pyridinecarboxamide;
4-[(1-Chloro-2-naphthyl)amino]-N-(2-hydroxyethoxy)-1-methyl-6-oxo-1,6-dihydro-3-pyridinecarboxamide;
N-(2,3-Dihydroxypropyl)-4-(2-fluoro-4-iodoanilino)-1-methyl-6-oxo-1,6-dihydro-3-pyridinecarboxamide;
4-(2-Fluoro-4-iodoanilino)-N-[2-hydroxy-1-(hydroxymethyl)ethyl]-1-methyl-6-oxo-1,6-dihydro-3-pyridinecarboxamide;
4-(2-Fluoro-4-iodoanilino)-N-[2-hydroxy-1,1-bis(hydroxymethyl)ethyl]-1-methyl-6-oxo-1,6-dihydro-3-pyridinecarboxamide;
2-Amino-3-hydroxy-2-(hydroxymethyl)propyl-4-(2-fluoro-4-iodoanilino)-1-methyl-6-oxo-1,6-dihydro-3-pyridinecarboxylate;
4-(2-Fluoro-4-iodoanilino)-N-(2-hydroxy-1-methylethyl)-1-methyl-6-oxo-1,6-dihydro-3-pyridinecarboxamide;
4-(2-Fluoro-4-iodoanilino)-N-(2-hydroxypropyl)-1-methyl-6-oxo-1,6-dihydro-3-pyridinecarboxamide;
4-(2-Fluoro-4-iodoanilino)-N,1-dimethyl-6-oxo-1,6-dihydro-3-pyridinecarboxamide;
4-(2-Fluoro-4-iodoanilino)-N,N,1-trimethyl-6-oxo-1,6-dihydro-3-pyridinecarboxamide;
N-(3-Aminopropyl)-4-(2-fluoro-4-iodoanilino)-1-methyl-6-oxo-1,6-dihydro-3-pyridinecarboxamide;
4-(4-Cyano-2-fluoroanilino)-1-methyl-6-oxo-1,6-dihydro-3-pyridinecarboxamide;
4-(2-fluoro-4-iodoanilino)-1-methyl-6-oxo-1,6-dihydro-3-pyridinecarboxylic acid;
4-(3,4-Dichloro-phenylamino)-1-methyl-6-oxo-1,6-dihydro-pyridine-3-carboxylic acid amide;
4-(3,4-Dimethyl-phenylamino)-1-methyl-6-oxo-1,6-dihydro-pyridine-3-carboxylic acid ethyl ester;
4-(Indan-5-ylamino)-1-methyl-6-oxo-1,6-dihydro-pyridine-3-carboxylic acid ethyl ester;
1-Methyl-6-oxo-4-(2,3,4-trichloro-phenylamino)-1,6-dihydro-pyridine-3-carboxylic acid ethyl ester;
4-(4-Chloro-3-trifluoromethyl-phenylamino)-1-methyl-6-oxo-1,6-dihydro-pyridine-3-carboxylic acid ethyl ester;
4-(1H-Indol-5-ylamino)-1-methyl-6-oxo-1,6-dihydro-pyridine-3-carboxylic acid ethyl ester;
4-(1H-Indazol-5-ylamino)-1-methyl-6-oxo-1,6-dihydro-pyridine-3-carboxylic acid ethyl ester;
4-(3,4-Dimethyl-phenylamino)-1-methyl-6-oxo-1,6-dihydro-pyridine-3-carboxylic acid;
4-(Indan-5-ylamino)-1-methyl-6-oxo-1,6-dihydro-pyridine-3-carboxylic acid;
1-Methyl-6-oxo-4-(2,3,4-trichloro-phenylamino)-1,6-dihydro-pyridine-3-carboxylic acid;
4-(4-Chloro-3-trifluoromethyl-phenylamino)-1-methyl-6-oxo-1,6-dihydro-pyridine-3-carboxylic acid;
4-(3,4-Dimethyl-phenylamino)-1-methyl-6-oxo-1,6-dihydro-pyridine-3-carboxylic acid amide;
4-(Indan-5-ylamino)-1-methyl-6-oxo-1,6-dihydro-pyridine-3-carboxylic acid amide;
4-(4-Chloro-3-trifluoromethyl-phenylamino)-1-methyl-6-oxo-1,6-dihydro-pyridine-3-carboxylic acid amide;
1-Methyl-6-oxo-4-(2,3,4-trichloro-phenylamino)-1,6-dihydro-pyridine-3-carboxylic acid amide;
4-(2-Fluoro-4-iodo-phenylamino)-1-methyl-6-oxo-1,6-dihydro-pyridine-3-carboxylic acid;
4-(2-Fluoro-4-iodo-phenylamino)-1-methyl-6-oxo-1,6-dihydro-pyridine-3-carboxylic acid amide;
4-(2-Fluoro-4-methyl-phenylamino)-1-methyl-6-oxo-1,6-dihydro-pyridine-3-carboxylic acid ethyl ester;

4-(2-Fluoro-4-iodo-phenylamino)-1-methyl-6-oxo-1,6-dihydro-pyridine-3-carboxylic acid ethyl ester;

4-(2-Fluoro-4-iodo-phenylamino)-1-methyl-6-oxo-1,6-dihydro-pyridine-3-carboxylic acid ethyl ester;

4-(4-Ethynyl-2-fluoro-phenylamino)-1-methyl-6-oxo-1,6-dihydro-pyridine-3-carboxylic acid ethyl ester;

4-(4-Ethynyl-2-fluoro-phenylamino)-1-methyl-6-oxo-1,6-dihydro-pyridine-3-carboxylic acid (2-hydroxy-ethyl)-amide;

4-(4-Ethynyl-2-fluoro-phenylamino)-1-methyl-6-oxo-1,6-dihydro-pyridine-3-carboxylic acid (2-hydroxy-1-hydroxymethyl-ethyl)-amide;

4-(4-Ethynyl-2-fluoro-phenylamino)-1-methyl-6-oxo-1,6-dihydro-pyridine-3-carboxylic acid (2,3-dihydroxy-propyl)-amide;

4-(4-Ethyl-2-fluoro-phenylamino)-1-methyl-6-oxo-1,6-dihydro-pyridine-3-carboxylic acid (2-hydroxy-ethyl)-amide;

4-(4-Ethyl-2-fluoro-phenylamino)-1-methyl-6-oxo-1,6-dihydro-pyridine-3-carboxylic acid (2-hydroxy-1-hydroxymethyl-ethyl)-amide;

4-(4-Ethyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(4-Ethyl-2-fluoro-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-1-methyl-6-oxo-1,6-dihydro-pyridine-3-carboxylic acid;

4-(2-Fluoro-4-methylsulfanyl-phenylamino)-1-methyl-6-oxo-1,6-dihydro-pyridine-3-carboxylic acid (3-hydroxy-propyl)-amide;

4-(2-Fluoro-4-methylsulfanyl-phenylamino)-1-methyl-6-oxo-1,6-dihydro-pyridine-3-carboxylic acid amide;

4-(2-Fluoro-4-methylsulfanyl-phenylamino)-1-methyl-6-oxo-1,6-dihydro-pyridine-3-carboxylic acid (2-hydroxy-ethyl)-amide;

4-(2-Fluoro-4-methylsulfanyl-phenylamino)-1-methyl-6-oxo-1,6-dihydro-pyridine-3-carboxylic acid (2,3-dihydroxy-propyl)-amide;

4-(2-Fluoro-4-methylsulfanyl-phenylamino)-1-methyl-6-oxo-1,6-dihydro-pyridine-3-carboxylic acid (2-hydroxy-1-hydroxymethyl-ethyl)-amide;

4-(2-Fluoro-4-methylsulfanyl-phenylamino)-5-[5-(2-hydroxy-ethylamino)-[1,3,4]oxadiazol-2-yl]-1-methyl-1H-pyridin-2-one;

4-(2-Fluoro-4-methylsulfanyl-phenylamino)-5-[5-(2-hydroxy-1-hydroxymethyl-ethylamino)-[1,3,4]oxadiazol-2-yl]-1-methyl-1H-pyridin-2-one;

5-[5-(2,3-Dihydroxy-propylamino)-[1,3,4]oxadiazol-2-yl]-4-(2-fluoro-4-methylsulfanyl-phenylamino)-1-methyl-1H-pyridin-2-one;

4-(4-Ethynyl-2-fluoro-phenylamino)-5-[5-(2-hydroxy-ethylamino)-[1,3,4]oxadiazol-2-yl]-1-methyl-1H-pyridin-2-one;

4-(4-Ethynyl-2-fluoro-phenylamino)-5-[5-(2-hydroxy-1-hydroxymethyl-ethylamino)-[1,3,4]oxadiazol-2-yl]-1-methyl-1H-pyridin-2-one;

4-(2-Fluoro-4-methanesulfinyl-phenylamino)-1-methyl-6-oxo-1,6-dihydro-pyridine-3-carboxylic acid (2-hydroxy-1-hydroxymethyl-ethyl)-amide;

4-(2-Fluoro-4-iodo-phenylamino)-1-methyl-6-oxo-1,6-dihydro-pyridine-3-carboxylic acid hydrazide;

4-(4-Ethynyl-2-fluoro-phenylamino)-1-methyl-6-oxo-1,6-dihydro-pyridine-3-carboxylic acid;

4-(4-Ethyl-2-fluoro-phenylamino)-1-methyl-6-oxo-1,6-dihydro-pyridine-3-carboxylic acid ethyl ester;

4-(4-Ethyl-2-fluoro-phenylamino)-1-methyl-6-oxo-1,6-dihydro-pyridine-3-carboxylic acid;

4-(2-Fluoro-4-iodo-phenylamino)-1-methyl-5-(5-oxo-4,5-dihydro-[1,3,4]oxadiazol-2-yl)-1H-pyridin-2-one; or 4-(4-Ethyl-2-fluoro-phenylamino)-1-methyl-6-oxo-1,6-dihydro-pyridine-3-carboxylic acid amide.

* * * * *